United States Patent
Hester, Jr. et al.

(10) Patent No.: US 6,911,549 B1
(45) Date of Patent: Jun. 28, 2005

(54) METHOD OF PREPARING A TAXOL DERIVATIVE

(76) Inventors: Jackson B. Hester, Jr., 9219 E. ML Ave., Galesburg, MI (US) 49053; Roy A. Johnson, 2122 Frederick Ave., Kalamazoo, MI (US) 49008; Robert C. Kelly, 936 E. Gull Lake Dr., Augusta, MI (US) 49012; Eldon G. Nidy, 3103 Morgan St., Kalamazoo, MI (US) 49001; Harvey I. Skulnick, 1745 Old Deer Run, Kalamazoo, MI (US) 49009

(*) Notice: Subject to any disclaimer, the term of this patent is extended or adjusted under 35 U.S.C. 154(b) by 0 days.

(21) Appl. No.: 08/454,210
(22) PCT Filed: Dec. 13, 1993
(86) PCT No.: PCT/US93/11827

§ 371 (c)(1),
(2), (4) Date: Jun. 9, 1995

(87) PCT Pub. No.: WO94/13655

PCT Pub. Date: Jun. 23, 1994

Related U.S. Application Data

(63) Continuation-in-part of application No. 08/122,974, filed on Sep. 17, 1993, now abandoned, which is a continuation-in-part of application No. 08/076,337, filed on Jun. 11, 1993, now abandoned, which is a continuation-in-part of application No. 08/013,826, filed on Feb. 2, 1993, now abandoned, which is a continuation-in-part of application No. 07/990,579, filed on Dec. 15, 1992, now abandoned.

(51) Int. Cl.$^7$ .......................................... C07D 305/14
(52) U.S. Cl. ...................................... 549/510; 514/449
(58) Field of Search .......................... 514/449; 549/510

(56) References Cited

U.S. PATENT DOCUMENTS

| | | | |
|---|---|---|---|
| 4,814,470 A | 3/1989 | Colin et al. ................ | 514/449 |
| 4,857,653 A | 8/1989 | Colin et al. ................ | 549/511 |
| 4,876,399 A | 10/1989 | Holton et al. ............... | 568/817 |
| 4,924,011 A | 5/1990 | Denis et al. ................ | 549/510 |
| 4,924,012 A | 5/1990 | Colin et al. ................ | 549/510 |
| 4,942,184 A | 7/1990 | Haugwitz et al. ........... | 514/449 |
| 4,960,790 A | 10/1990 | Stella et al. ................ | 514/449 |
| 5,015,744 A | 5/1991 | Holton ........................ | 549/510 |
| 5,059,699 A | 10/1991 | Kingston et al. ........... | 549/511 |
| 5,136,060 A | 8/1992 | Holton ........................ | 549/510 |
| 5,157,049 A | 10/1992 | Haugwitz et al. ........... | 514/449 |
| 5,200,534 A * | 4/1993 | Rao ............................ | 549/510 |
| 5,227,400 A | 7/1993 | Holton et al. ............... | 514/444 |
| 5,248,796 A | 9/1993 | Chen et al. .................. | 549/510 |
| 5,254,580 A | 10/1993 | Chen et al. .................. | 514/449 |
| 5,294,637 A | 3/1994 | Chen et al. .................. | 514/449 |
| 5,380,751 A | 1/1995 | Chen et al. .................. | 514/449 |
| 5,476,954 A * | 12/1995 | Bourzat et al. ............... | 549/510 |
| 5,532,388 A | 7/1996 | Bouchard et al. ........... | 549/510 |
| 5,550,261 A | 8/1996 | Bouchard et al. ........... | 549/510 |
| 5,571,917 A | 11/1996 | Bouchard et al. ........... | 544/369 |
| 5,576,450 A | 11/1996 | Bouchard et al. ........... | 549/510 |
| 5,580,997 A | 12/1996 | Bouchard et al. ........... | 549/510 |
| 5,580,998 A | 12/1996 | Bouchard et al. ........... | 549/510 |
| 5,587,493 A | 12/1996 | Bouchard et al. ........... | 549/510 |
| 5,599,942 A | 2/1997 | Bouchard et al. ........... | 548/215 |
| 5,616,739 A | 4/1997 | Mas et al. ................... | 549/510 |
| 5,621,121 A | 4/1997 | Commercon et al. ....... | 549/510 |
| 5,637,723 A | 6/1997 | Commercon et al. ....... | 548/215 |

FOREIGN PATENT DOCUMENTS

| | | | |
|---|---|---|---|
| EP | 0 253 739 A1 | 1/1988 | ......... C07D/305/14 |
| EP | 0 400 971 | 12/1990 | ......... C07D/205/08 |
| EP | 414 610 A1 | 2/1991 | ......... C07C/233/83 |
| EP | 0 428 708 A1 | 5/1991 | ......... C07D/265/04 |
| EP | 0 534 708 A1 | 3/1993 | ......... C07D/405/12 |
| EP | 0 534 709 A1 | 3/1993 | ......... C07D/305/14 |
| EP | A1 577 082 | 1/1994 | ......... A61K/31/335 |
| EP | A1 577 083 | 1/1994 | ......... C07D/305/14 |
| EP | 0 600 517 A1 | 6/1994 | ......... C07D/305/14 |
| EP | 0 663 905 | 1/1997 | ......... C07D/305/14 |
| WO | WO 91/13053 | 9/1991 | ......... C07C/229/34 |
| WO | WO 91/13066 | 9/1991 | ......... C07D/303/48 |
| WO | WO 91/17976 | 11/1991 | ......... C07C/235/84 |
| WO | WO 91/17977 | 11/1991 | ......... C07C/235/84 |
| WO | WO 92/09589 | 6/1992 | ......... C07D/305/14 |
| WO | WO 93/16060 | 8/1993 | ......... C07D/305/14 |
| WO | WO 94/07876 | 4/1994 | ......... C07D/305/14 |
| WO | WO 94/07877 | 4/1994 | ......... C07D/305/14 |
| WO | WO 94/07878 | 4/1994 | ......... C07D/305/14 |
| WO | WO 94/07879 | 4/1994 | ......... C07D/305/14 |
| WO | WO 94/10169 | 5/1994 | ......... C07D/413/12 |
| WO | WO 94/13654 | 6/1994 | ......... C07D/305/14 |

OTHER PUBLICATIONS

Roger Grant and Claire Grant, Grank and Hackh's Chemical Dictionary, 5$^{th}$ Ed., M$^c$Graw–Hill Book Company NY(1987) pp. 289–290.*

Gueritte–Voegelein, Francoise; Guenard, Daniel; Lavelle, Francois; Le Goff, Marie–Therese; Mangatal, Lydie; Potier, Pierre; Relationships between the Structure of Taxol Analogues and Their Antimitotic Activity, J. Med. Chem., 1991, 34, 992–998.

(Continued)

Primary Examiner—Laura L. Stockton
(74) Attorney, Agent, or Firm—Marshall, Gerstein & Borun LLP

(57) ABSTRACT

This invention provides 7-deoxy-taxol analogs of Formula I:

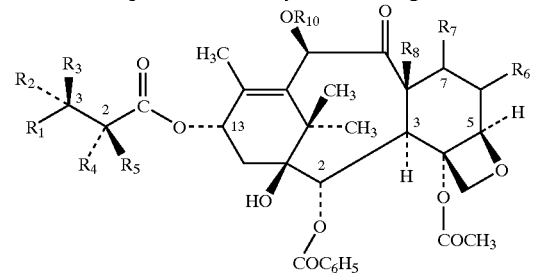

The compounds of Formula I (including II and III) are useful for the same cancers for which taxol has been shown active, including human ovarian cancer, breast cancer, and malignant melanoma as well as lung cancer, gastric cancer, colon cancer, head and neck cancer, and leukemia.

1 Claim, No Drawings

OTHER PUBLICATIONS

IUPAC Commission on the Nomenclature of Organic Chemistry, Eur. J. Biochem. 86, 1–8 (1978).

Bouchard et al, CA 121:258019, Jun. 9, 1994 (WO94/1245).

Castro, Bertrand R., Replacement of Alcoholic Hydroxyl Groups By Halogens and Other Nucleophiles Via Oxyphosphonium Intermediates, 29, pp 1–162 (1983).

Chaudhary, Ashok G, Rimoldi, John M., Kingston, David G.I., Modified Taxols. 10. Preparation of 7–Deoxytaxol, a Highly Bioactive Taxol Derivative, and Interconversion of Taxol and 7–epi–Taxol[1], J. Org. Chem., 58, 3798–3799 (1993).

Chaudhary, Ashok G., Gharpure, Milind M., Rimoldi, John M., Chordia, Mahendra D., Gunatilaka, A.A. Leslie, Kingston, David G.I., Unexpectedly Facile Hydrolysis of the 2–Benzoate Group of Taxol and Syntheses of Analogs with Increased Activities, J.Am. Chem. Soc. 116, 4097–4098 (1994).

Chen, Shu–Hui, Huang, Stella and Farina, Vittorio, On The Reaction of Taxol With Dast, Tetrahedron Letters, vol. 35, No. 1, pp 41–44, (1994).

Chen, Shu–Hui, Huang, Stella, Wei, Jianmei, Farina, Vittorio, Serendipitous Synthesis of a Cyclopropane–Containing Taxol Analog via Anchimeric Participation of an Unactivated Angular Methyl Group, J. Org. Chem., 58, 4520–4521 (1993).

Commercon, A., Bezard, D., Bernard, F., Bourzat, J.D., Improved Protection and Esterification of a Precursor of the Taxotere and Taxol Side Chains, Tetrahedron Letters, No. 36, 5185–5188 (1992).

Denis, Jean–Joel, Greene, Andrew E., A Highly Efficient, Practical Approach to Natural Taxol, J. Am. Chem. Soc., 110, 5917–5919 (1988).

Denis, J–N., Correa, A., Greene, A.E., An Improved Synthesis of the Taxol Side Chain and of RP 56976, J. Org. Chem., 1990, 55, 1957–1957.

Didier, Eric, Fouque, Elie, Taillepied, Isabelle and Commercon, Alain, 2–Monosubstituted–1,3–Oxazolidines as Improved Protective Groups of N–Boc–Phenylisoserine in Docetaxel Preparation, Tetrahedron Letters 35(15):2349–252 (1994).

Gaskin, Felicia, Cantor, Charles R., Turbidimetric Studies of the in Vitro Assembly and Disassembly of Porcine Neurotubules, J. Mol. Biol. 89, 737–758 (1974).

Georg, G.I., Cheruvallath, Z. S., Himes, R.H., Mejillano, M.R., BioMed..Chem. Lett., 1992, 2, 295.

Li, Li H., Kuentzel, Sandra L., Murch, Lana L., Pschigoda, Loraine M., Krueger, William C., Comparative Biological and Biochemical Effects of Nogalamycin and Its Analogs on L1210 Leukemia, Cancer Research 39, 4816–4822 (Dec. 1979).

Kingston, David G.I., The Chemistry of Taxol, Pharmac. Ther., vol. 52, pp. 1–34, (1991).

Klein, Larry L., Maring Clarence J., Li, Leping, Yeung, Clinton M., Thomas, Sheela A., Grampovink, David J., Plattner, Jacob J., Henry Rodger F., Synthesis of Ring B–Rearranged Taxane Analogs, J. Org. Chem. 59, 2370–2373 (1994).

Magri, Neal F., Kingston, David G.I., Modified Taxols. 2.[1] Oxidation Products of Taxol, J. Org. Chem. 51, 797–802 (1986).

Magri, Neal F., Kingston, David G.I., Modified Taxols, 4. [1]Synthesis and Biological Activity of Taxols Modified in the Side Chain, Journal of Natural Products, vol. 51, No. 2, pp 298–306,Mar.–Apr. 1988.

Mangatal, L., Adeline, M.–T., Guenard, D., Gueritte–Vogelein, F., Potier, P., Application of the Vicinal Oxyamination Reaction With Asymmetric Induction To The Hemisynthesis of Taxol and Analogues, Tetrahedron, 1989, vol. 45, No. 13, 4177–4190.

Monsarrat, Bernard, Mariel, Eric, Cros, Suzie, Gares, Michele, Guenard, Daniel, Gueritte–Voegelein, Francoise, Wright, Michel, Taxol Metabolism Isolation and Identification of Three Major Metabolities of Taxol in Rat Bile, Drug Metabolism and Disposition, vol. 18, No. 6, pp. 895–901, 1990.

Mathew, Abraham, E., Mejiliano, Magdalena R., Nath, Jyoti P., Himes, Richard H., Stella, Valentino J., Synthesis and Evaluation of Some Water–soluble Products and Derivatives of Taxol with Antitumor Activity, J. Med. Chem. 35, 145–151 (1992).

Ojima, Iwao, Habus, Ivan, Zhao, Mangzhu, Efficient and Practical Asymmmetric Synthesis of the Taxol C–13 Side Chain, N–Benzoyl–(2R, 3S)–3–phenylisoserine, and Its Analogues via Chiral 3–Hydroxy–4–aryl–βlactams through Chiral Ester Enolate–Imine Cyclocondensation, J. Org. Chem., 56, 1681–1683 (1991).

Ojima, Iwano, Zucco, Martine, Duclos, Olivier, Kuduk, Scott D., Sun, Chung Ming, Park, Young Hoon, N–Acyl–3–Hydroxy–βLactams as Key Intermediates for Taxotere and its Analogs, Biooragnic & Medicinal Chemistry Letters, vol. 3, No. 11 2479–2482 (1993).

Ringel, Isreal and Horwitz, Susan Band, Taxol is Converted to 7–Epitaxol, a Biologically Active Isomer, in Cell Culture Medium, The Journal of Pharmacology and Experimental Therapeutics, vol. 242, 692–698 (1987).

Rowinsky, Eric K., Donehower, Ross C., The Clinical Pharmacology and Use of Antimicrotubule Agents in Cancer Chemotherapeutics, Pharmac Ther. Vol. 52, pp 35–84 (1991).

Samaranayake, Gamini, Magri, Neal F., Jitrangsri, Chote, Kingston, David G.I., Modified Taxol. 5.[1] Reaction of Taxol with Electrophilic Reagents and preparation of a Rearranged Taxol Derivative with Tubulin Assembly Activity[2], J. Org. Chem., 56, 5114–5119 (1991).

Slichenmyer, William J., VonHoff, Daniel D., Taxol: a new and effective anti–cancer drug, Anti–Cancer Drugs, 2, pp 519–530(1991).

* cited by examiner

METHOD OF PREPARING A TAXOL DERIVATIVE

This is the U.S. national phase of international application No. PCT/US93/11827, which is a continuation-in-part of U.S. patent application Ser. No. 08/122,974 filed Sep. 17, 1993, abandoned, which is a continuation-in-part of each of: (a) U.S. patent application Ser. No. 08/076,337 filed Jun. 11, 1993, abandoned; (b) U.S. patent application Ser. No. 08/013,826 filed Feb. 2, 1993, abandoned; and (c) U.S. patent application Ser. No. 07/990,579 filed Dec. 15, 1992, now abandoned, the disclosures of each of which are hereby incorporated by reference.

BACKGROUND OF THE INVENTION

Taxol is a member of the taxane family of diterpenes, having the structure shown below:

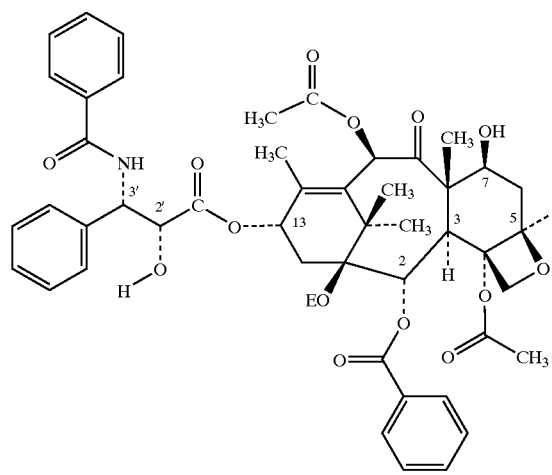

The numbering system shown for taxol is that recommended by IUPAC (IUPAC, Commission on the Nomenclature of Organic Chemistry, 1978).

The chemistry of the potent anticancer diterpenoid taxol and analogs thereof is reviewed, with an emphasis on isolation and analysis, structural modifications, partial synthesis, and structure-activity relationships by David G. I. Kingston, The Chemistry of Taxol, Pharmac. Ther., Vol 52, pp 1–34, 1991.

The clinical pharmacology of taxol is reviewed by Eric K. Rowinsky and Ross C. Donehower, The Clinical Pharmacology and Use of Antimicrotubule Agents in Cancer Chemotherapeutics, Pharmac. Ther., Vol 52, pp 35–84, 1991. Clinical and preclinical studies with taxol are reviewed by William J. Slichenmyer and Daniel D. Von Hoff, Taxol: A New and Effective Anti-cancer Drug, Anti-Cancer Drugs, Vol. 2, pp 519–530, 1991.

Taxol and analogs thereof are the subject of various patents including, for example, U.S. Pat. Nos. 4,814,470; 4,857,653; 4,942,184; 4,924,011; 4,924,012; 4,960,790; 5,015,744; 5,157,049; 5,059,699; 5,136,060; 4,876,399; 5,227,400 as well as PCT Publication No. WO 92/09589, European Patent Application 90305845.1 (Publication No. A2 0 400 971), 90312366.9 (Publication No. A1 0 428 376), 89400935.6 (Publication No. A1 0 366 841) and 90402333.0 (Publication No. 0 414 610 A1), 87401669.4 (A1 0 253 739), 92308608.6 (A1 0 534 708), 92308609.4 (A1 534 709) and PCT Publication Nos. WO 91/17977, WO 91/17976. WO 91/13066. WO 91/13053.

Various processes for the preparation of taxol (and intermediates and analogs thereof) are described in Tetrahedron Letters. 1992, 33, 5185; J. Org. Chem., 1991, 56, 1681 and J. Org. Chem., 1991, 56, 5114.

Chen et al., Serendipitous Synthesis of a Cyclopropane-Containing Taxol Analog via Anchimeric Participation of an Unactivated Angular Methyl Group, Advance ACS Abstracts, Vol 1, No. 2., Jul. 15, 1993 reported the treatment of a 7-epi taxol derivative with DAST in dichloromethane led to an unexpected reaction involving participation of the C-19 methyl group and clean formation of a cyclopropane ring. See also J. Org. Chem., 1993, 58, 4520 (Aug. 13, 1993).

U.S. Pat. No. 5,248,796 (granted 28 Sep. 1993) relates to 10-desacetoxy-11,12-dihydrotaxol-10,12(18)-diene derivatives and the preparation of 10-desacetoxytaxol.

SUMMARY OF THE INVENTION

This invention provides 7-deoxy-taxol analogs of Formula I:

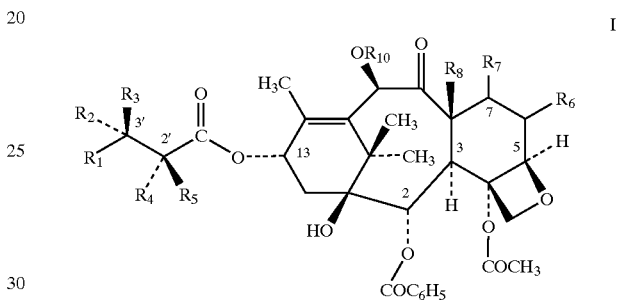

The compounds of Formula I are useful for the same cancers for which taxol has been shown active, including human ovarian cancer, breast cancer, and malignant melanoma as well as lung cancer, gastric cancer, colon cancer, head and neck cancer, and leukemia.

Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C($=Z_1$) H. Groups $R_i$ and $R_j$ would represent monovalent variable substituents if attached to the formula $CH_3$—$CH_2$—C($R_i$)($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as taxol, these carbon atoms are designated as $C_i$, where "i" is the integer corresponding to the carbon atom number. For example, $C_6$ represents the 6 position or carbon atom number in the nucleus as traditionally designated by those skilled in the art.

Chemical formulas or portions thereof drawn in a linear fashion represent atoms in a linear chain. The symbol "—" in general represents a bond between two atoms in the chain. Thus $CH_3$—O—$CH_2$—CH($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$—C*$H_2$. Similarly, 2-furyl can be represented by —C*—O—CH=CH—C*H= and 2-thienyl represented by —C*—S—CH=CH—C*H=.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents α-$R_{i-j}$ and β-$R_{i-k}$. When a bivalent variable, $R_i$, is defined to consist of two monovalent variable substituents, the convention used to define the bivalent variable is of the form "α-$R_{i-j}$:β-$R_{i-k}$" or some variant thereof. In such a case both α-$R_{i-j}$ and β-$R_{i-k}$ are attached to the carbon atom to give —C(α-$R_{i-j}$)(β-$R_{i-k}$)—. For example, when the bivalent variable $R_6$, —C(=$R_6$)— is defined to consist of two monovalent variable substituents, the two monovalent variable substituents are α-$R_{6-1}$:β-$R_{6-2}$, . . . α-$R_{6-9}$:β-$R_{6-10}$, etc, giving —C(α-$R_{6-1}$)(β-$R_{6-2}$)—, . . . —C(α-$R_{6-9}$)(β-$R_{6-10}$)—, etc. Likewise, for the bivalent variable $R_{11}$, —C(=$R_{11}$)—, two monovalent variable substituents are α-$R_{11-1}$:β-$R_{11-2}$. For a ring substituent for which separate α and β orientations do not exist (e.g. due to the presence of a carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1$($R_i$)H—$C_2$($R_j$)H— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO— . . ." means a lactone in which the carbonyl is bonded to $C_2$. However, when designated ". . . $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—($CH_2$)$_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$) alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

DETAILED DESCRIPTION OF THE INVENTION

More specifically, this invention provides 7-deoxy-taxol analogs of general Formula I

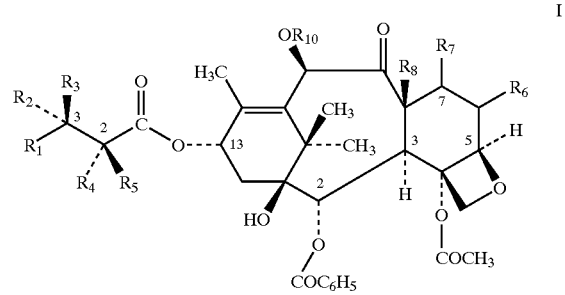

wherein:
$R_1$ is selected from the group consisting of
—$CH_3$,

—$C_6H_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, -2-furyl, 2-thienyl, 1-naphthyl, 2-naphthyl or 3,4-methylenedioxyphenyl;

$R_2$ is selected from the group consisting of —H, —NHC(O)H, —NHC(O)$C_1$–$C_{10}$alkyl (preferably —NHC(O)$C_4$–$C_6$alkyl), —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C(CH_3)=CHCH_3, —NHC(O)OC(CH_3)_3, —NHC(O)OCH_2phenyl, —NH_2, —NHSO_2-4-methylphenyl, —NHC(O)(CH_2)_3COOH, —NHC(O)-4-(SO_3H)phenyl, —OH, —NHC(O)-1-adamantyl, —NHC(O)O-3-tetrahydrofuranyl, —NHC(O)O-4-tetrahydropyranyl, —NHC(O)CH_2C(CH_3)_3, —NHC(O)C(CH_3)_3, —NHC(O)OC_1–C_{10}alkyl, —NHC(O)NHC_1–C_{10}alkyl, —NHC(O)NHPh, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —NHC(O)C_3–C_8cycloalkyl, —NHC(O)C(CH_2CH_3)_2CH_3, —NHC(O)C(CH_3)_2CH_2Cl, —NHC(O)C(CH_3)_2CH_2CH_3, phthalimido, —NHC(O)-1-phenyl-1-cyclopentyl, —NHC(O)-1-methyl-1-cyclohexyl, —NHC(S)NHC(CH_3)_3, —NHC(O)NHCC(CH_3)_3 or —NHC(O)NHPh;

$R_3$ is selected from the group consisting of —H, —NHC(O)phenyl or —NHC(O)OC(CH_3)_3, with the overall proviso that one of $R_2$ and $R_3$ is —H but $R_2$ and $R_3$ are not both —H;

$R_4$ is —H or selected from the group consisting of —OH, —OAc (—OC(O)CH_3), —OC(O)OCH_2C(Cl)_3, —OCOCH_2CH_2NH_3^+HCOO^-, —NHC(O)phenyl, —NHC(O)OC(CH_3)_3, —OCOCH_2CH_2COOH and pharmaceutically acceptable salts thereof, —OCO(CH_2)_3COOH and pharmaceutically acceptable salts thereof, and —OC(O)—Z—C(O)—R' [where Z is ethylene (—CH_2CH_2—), propylene (—CH_2CH_2CH_2—), —CH=CH—, 1,2-cyclohexane or 1,2-phenylene, R' is —OH, —OH base, —NR'_2R'_3, —OR'_3, —SR'_3, —OCH_2C(O)NR'_4R'_5 where R'_2 is —H or —CH_3, R'_3 is —(CH_2)_nNR'_6R'_7 or (CH_2)_nN^+R'_6R'_7R'_8X^- where n is 1–3, R'_4 is —H or —C_1–C_4alkyl, R'_5 is —H. —C_1–C_4alkyl, benzyl, hydroxyethyl, —CH_2CO_2H or dimethylaminoethyl, R'_6 and R'_7 are —CH_3, —CH_2CH_3, benzyl or R'_6 and R'_7 together with the nitrogen of NR'_6R'_7 form a pyrrolidino, piperidino, morpholino, or N-methylpiperizino group; R'_8 is —CH_3, —CH_2CH_3 or benzyl, X^- is halide, and base is NH_3, (HOC_2H_4)_3N, N(CH_3)_3, CH_3N(C_2H_4)_2NH, NH_2(CH_2)_6NH_2, N-methylglucamine, NaOH or KOH], —OC(O)(CH_2)_nNR^2R^3 [where n is 1–3, $R^2$ is —H or —C_1–C_3alkyl and $R^3$ is —H or —C_1–C_3alkyl], —OC(O)CH(R")NH_2 [where R" is selected from the group consisting of —H, —CH_3, —CH_2CH(CH_3)_2, —CH(CH_3)CH_2CH_3, —CH(CH_3)_2, —CH_2phenyl, —(CH_2)_4NH_2, —CH_2CH_2COOH, —(CH_2)_3NHC(=NH)NH_2], the residue of the amino acid proline, —OC(O)CH=CH_2, —C(O)CH_2CH_2C(O)NHCH_2CH_2SO_3^-Y^+, —OC(O)CH_2CH_2C(O)NHCH_2CH_2CH_2SO_3^-Y^+ wherein Y^+ is Na^+ or N^+(Bu)_4, —OC(O)CH_2CH_2C(O)OCH_2CH_2OH;

$R_5$ is —H or —OH, with the overall proviso that when $R_5$ is —OH, $R_4$ is —H and with the further proviso that when $R_5$ is —H, $R_4$ is other than —H;

$R_6$ is —H:—H when $R_7$ is α-$R_{71}$:β-$R_{72}$ where one of $R_{71}$ and $R_{72}$ is —H and the other of $R_{71}$ and $R_{72}$ is —X where X is halo and $R_8$ is —CH_3;

$R_6$ is —H:—H when $R_7$ is α-H:β-$R_{74}$ where $R_{74}$ and $R_8$ are taken together to form a cyclopropyl ring;

$R_{10}$ is —H or —C(O)CH_3; and pharmaceutically acceptable salts thereof when the compound contains either an acidic or basic functional group.

A preferred embodiment of the subject invention is compounds of Formula I where $R_1$ is phenyl or phenyl substituted with halo, $R_2$ is —NHC(O)$C_6H_5$, $R_3$ and $R_5$ are —H, $R_4$ is —OH, and $R_{10}$ is —H or —C(O)CH_3. Another preferred embodiment of the subject invention is compounds of Formula I where $R_1$ is preferably phenyl or phenyl substituted with halo, $R_2$ is —NHC(O)OC(CH_3)_3, $R_3$ and $R_5$ are —H, $R_4$ is —OH, and $R_{10}$ is —H or —COCH_3. A further preferred embodiment of the subject invention is compounds of Formula I where $R_1$ is preferably phenyl or phenyl substituted with halo, $R_2$ is —NHC(O)NHC(CH_3)_3, $R_3$ and $R_5$ are —H, $R_4$ is —OH, and $R_{10}$ is —H or —COCH_3.

An embodiment of the subject invention are compounds of Formula I where $R_1$ is selected from the group consisting of —CH_3, —C_6H_5 or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro and $R_2$ is selected from the group consisting of —H, —NHC(O)H, —NHC(O)$C_1$–$C_{10}$alkyl (preferably —NHC(O)$C_4$–$C_6$alkyl), —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C(CH_3)=CHCH_3, —NHC(O)OC(CH_3)_3, —NHC(O)OCH_2phenyl, —NH_2, —NHSO_2-4-methylphenyl, —NHC(O)(CH_2)_3COOH, —NHC(O)-4-(SO_3H)phenyl, —OH, —NHC(O)-1-adamantyl, —NHC(O)O-3-tetrahydrofuranyl, —NHC(O)O-4-tetrahydropyranyl, —NHC(O)CH_2C(CH_3)_3, —NHC(O)C(CH_3)_3, —NHC(O)OC_1–C_{10}alkyl, —NHC(O)NHC_1–C_{10}alkyl, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro.

This invention also provides taxol analogs of general Formula II

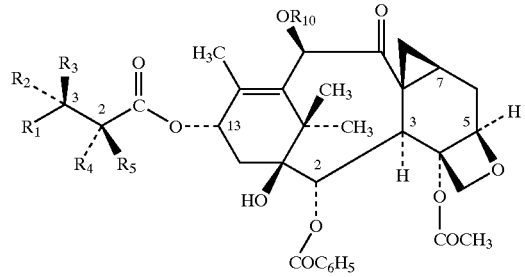

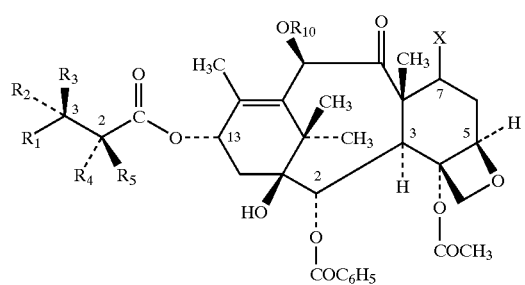

wherein

X is a halogen atom selected from the group consisting of —F, —Br, —Cl and —I; and wherein $R_1$, $R_2$, $R_3$, $R_4$, $R_5$ and $R_{10}$ are as defined above.

An embodiment of the present invention are 7-deoxy-7β, 8β-methano-taxol analogs of general Formula II wherein:

7

$R_1$ is selected from the group consisting of —$CH_3$, —$C_6H_5$ or phenyl substituted with one, 2 or 3 $C_1$–$C_4$ alkyl, $C_1$–$C_3$ alkoxy, halo, $C_1$–$C_3$ alkylthio, trifluoromethyl. $C_2$–$C_6$ dialkylamino, hydroxy or nitro;

$R_2$ is selected from the group consisting of —H, —NHC(O)$C_1$–$C_{10}$alkyl (preferably —NHC(O)$C_4$–$C_6$alkyl), —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C($CH_3$)=$CHCH_3$, —NHC(O)OC($CH_3$)$_3$, —$NH_2$, —$NHSO_2$-4-methylphenyl, —NHC(O)($CH_2$)$_3$COOH, —NHC(O)-4-($SO_3$H)phenyl, or —OH;

$R_3$ is selected from the group consisting of —H, —NHC(O)phenyl or —NHC(O)OC($CH_3$)$_3$, with the overall proviso that one of $R_2$ and $R_3$ is —H but $R_2$ and $R_3$ are not both —H;

$R_4$ is —H or selected from the group consisting of —OH, —OAc (—OC(O)$CH_3$), —OC(O)O$CH_2$C(Cl)$_3$, —OCOC$H_2$C$H_2$N$H_3^+$HCOO$^-$, —NHC(O)phenyl, —NHC(O)OC($CH_3$)$_3$, —OCOC$H_2$C$H_2$COOH and pharmaceutically acceptable salts thereof, —OCO($CH_2$)$_3$COOH and pharmaceutically acceptable salts thereof, and —OC(O)—Z—C(O)—R' [where Z is ethylene (—$CH_2CH_2$—), propylene (—$CH_2CH_2CH_2$—), —CH=CH—, 1,2-cyclohexane or 1,2-phenylene, R' is —OH, —OH base, —NR'$_2$R'$_3$, —OR'$_3$, —SR'$_3$, —OC$H_2$C(O)NR'$_4$R'$_5$ where R'$_2$ is —H or —$CH_3$, R'$_3$ is —($CH_2$)$_n$NR'$_6$R'$_7$ or ($CH_2$)$_n$N$^+$R'$_6$R'$_7$R'$_8$X$^-$ where n is 1–3, R'$_4$ is —H or —$C_1$–$C_4$alkyl, R'$_5$ is —H, —$C_1$–$C_4$alkyl, benzyl, hydroxyethyl, —$CH_2CO_2$H or dimethylaminoethyl, R'$_6$ and R'$_7$ are —$CH_3$, —$CH_2CH_3$, benzyl or R'$_6$ and R'$_7$ together with the nitrogen of NR'$_6$R'$_7$ form a pyrrolidino, piperidino, morpholino, or N-methylpiperizino group; R'$_8$ is —$CH_3$, —$CH_2CH_3$ or benzyl, X$^-$ is halide, and base is $NH_3$, (HO$C_2H_4$)$_3$N, N($CH_3$)$_3$, $CH_3$N($C_2H_4$)$_2$NH, $NH_2$($CH_2$)$_6$$NH_2$, N-methylglucamine, NaOH or KOH], —OC(O)($CH_2$)$_n$NR$^2$R$^3$ [where n is 1–3, R$^2$ is —H or —$C_1$–$C_3$alkyl and R$^3$ is —H or —$C_1$–$C_3$alkyl], —OC(O)CH(R")NH$_2$ [where R" is selected from the group consisting of —H, —$CH_3$, —$CH_2CH(CH_3)_2$, —CH($CH_3$)$CH_2CH_3$, —CH($CH_3$)$_2$, —$CH_2$phenyl, —($CH_2$)$_4$NH$_2$, —$CH_2CH_2$COOH, —($CH_2$)$_3$ NHC(=NH)$NH_2$], the residue of the amino acid proline, —OC(O)CH=$CH_2$, —C(O)$CH_2CH_2$C(O)NHC$H_2C H_2SO_3^-$Y$^+$, —OC(O)$CH_2CH_2$C(O)NHC$H_2C H_2CH_2SO_3^-$Y$^+$ wherein Y$^+$ is Na$^+$ or N$^+$(Bu)$_4$, —OC(O)$CH_2CH_2$C(O)OC$H_2CH_2$OH;

$R_5$ is —H or —OH, with the overall proviso that when $R_5$ is —OH, $R_4$ is —H and with the further proviso that when $R_5$ is —H, $R_4$ is other than —H;

$R_{10}$ is —H or —C(O)$CH_3$; and pharmaceutically acceptable salts thereof when the compound contains either an acidic or basic functional group.

Another embodiment of the present invention are 7-deoxy-7β,8β-methano-taxol analogs of general Formula II wherein:

$R_1$ is selected from the group consisting of —$CH_3$, —$C_6H_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro;

$R_2$ is selected from the group consisting of —NHC(O)-1-adamantyl, —NHC(O)O-3-tetrahydrofuranyl, —NHC(O)O-4-tetrahydropyranyl, —NHC(O)$CH_2$C($CH_3$)$_3$, —NHC(O)C($CH_3$)$_3$, —NHC(O)OC$_1$–$C_{10}$alkyl, —NHC(O)NHC$_1$–$C_{10}$alkyl, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —NHC(O)$C_3$–$C_8$cycloalkyl; and

8

$R_3$, $R_4$, $R_5$ and $R_{10}$ are as defined above.

A preferred embodiment of the subject invention is compounds of Formula II where $R_1$ is phenyl or phenyl substituted with halo, $R_2$ is —NHC(O)$C_6H_5$, $R_3$ and $R_5$ are —H, and $R_{10}$ is —C(O)$CH_3$. Another preferred embodiment of the subject invention is compounds of Formula II where $R_1$ is preferably phenyl or phenyl substituted with halo, $R_2$ is —NHC(O)OC($CH_3$)$_3$, and $R_3$, $R_5$ and $R_{10}$ are —H. A further preferred embodiment of the subject invention is compounds of Formula II where $R_1$ is preferably phenyl or phenyl substituted with halo, $R_2$ is —NHC(O)OC($CH_3$)$_3$, and $R_3$ and $R_5$ are —H, and $R_{10}$ is —C(O)$CH_3$. Another preferred embodiment of the subject invention is compounds of Formula II where $R_1$ is preferably phenyl or phenyl substituted with halo, $R_2$ is —NHC(O)NHC($CH_3$)$_3$, $R_3$ and $R_5$ are —H, $R_4$ is —OH, and $R_{10}$ is —H or —COC$H_3$.

Additional preferred embodiments of Formula II include:

The compound according to Formula II, namely 7-deoxy-7β,8β-methano-taxol;

The compound according to Formula II, namely 2'-[[(2,2,2-trichloroethyl)oxy]carbonyl]-7-deoxy-7β,8β-methano-taxol; and The compound according to Formula II, namely 10-acetyl-7-deoxy-7β,8β-methano-taxotere; and The compound according to Formula II, namely N-Debenzoyl-n-(t-butyl)aminocarbonyl-7-deoxy-7β,8β-methano-taxol.

Another embodiment of the present invention are 7-halotaxol analogs of general Formula III wherein:

X is a halogen atom selected from the group consisting of —F, —Br, —Cl and —I;

$R_1$ is selected from the group consisting of —$CH_3$, —$C_6H_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro;

$R_2$ is selected from the group consisting of —H, —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro,— NHC(O)C($CH_3$)=$CHCH_3$, —NHC(O)OC($CH_3$)$_3$, —$NH_2$, —$NHSO_2$-4-methylphenyl, —NHC(O)($CH_2$)$_3$COOH, —NHC(O)-4-($SO_3$H)phenyl, or —OH;

$R_3$ is selected from the group consisting of —H, —NHC(O)phenyl or —NHC(O)OC($CH_3$)$_3$, with the overall proviso that one of $R_2$ and $R_3$ is —H but $R_2$ and $R_3$ are not both —H;

$R_4$ is —H or selected from the group consisting of —OH, —OAc(—OC(O)$CH_3$), —OC(O)O$CH_2$C(Cl)$_3$, —OCOC$H_2CH_2NH_3^+$HCOO$^-$, —NHC(O)phenyl, —NHC(O)OC($CH_3$)$_3$, —OCOC$H_2CH_2$COOH and pharmaceutically acceptable salts thereof, —CO($CH_2$)$_3$COOH and pharmaceutically acceptable salts thereof, and —OC(O)—Z—C(O)—R' [where Z is ethylene (—$CH_2CH_2$—), propylene (—$CH_2CH_2CH_2$—), —CH=CH—, 1,2-cyclohexane or 1,2-phenylene, R' is —OH, —OH base, —NR'$_2$R'$_3$, —OR'$_3$, —SR'$_3$, —OC$H_2$C(O)NR'$_4$R'$_5$ where R'$_2$ is —H or —$CH_3$, R'$_3$ is —($CH_2$)$_n$NR'$_6$R'$_7$ or ($CH_2$)$_n$N$^+$R'$_6$R'$_7$R'$_8$X$^-$ where n is 1–3, R'$_4$ is —H or —$C_1$–$C_4$alkyl, R'$_5$ is —H, —$C_1$–$C_4$alkyl, benzyl, hydroxyethyl, —$CH_2CO_2$H or dimethylaminoethyl, R'$_6$ and R'$_7$ are —$CH_3$, —$CH_2CH_3$, benzyl or R'$_6$ and R'$_7$ together with the nitrogen of NR'$_6$R'$_7$ form a pyrrolidino, piperidino, morpholino, or N-methylpiperizino group; R'$_8$ is —$CH_3$—$CH_2CH_3$ or benzyl , X$^-$ is halide, and base is $NH_3$, (HO$C_2H_4$)$_3$N, N($CH_3$)$_3$, $CH_3$N($C_2H_4$)$_2$NH, $NH_2$($CH_2$)$_6$$NH_2$, N-methylglucamine, NaOH or KOH], —OC(O)($CH_2$)$_n$NR$^2$R$^3$ [where n is 1–3, R$^2$ is —H or —$C_1$–$C_3$alkyl and R$^3$ is —H or —$C_1$–$C_3$alkyl], —OC(O)CH(R")NH$_2$ [where R" is selected from the group consisting of —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_4$NH$_2$, —CH$_2$CH$_2$COOH, —(CH$_2$)$_3$NHC(=NH)NH$_2$], the residue of the amino acid proline, —OC(O)CH=CH$_2$, —C(O)CH$_2$CH$_2$C(O)NHCH$_2$CH$_2$SO$_3$⁻Y⁺, —OC(O)CH$_2$CH$_2$C(O)NHCH$_2$CH$_2$CH$_2$SO$_3$⁻Y⁺ wherein Y⁺ is Na⁺ or N⁺(Bu)$_4$, —OC(O)CH$_2$CH$_2$C(O)OCH$_2$ CH$_2$OH;

R$_5$ is —H or —OH, with the overall proviso that when R$_5$ is —OH, R$_4$ is —H and with the further proviso that when R$_5$ is —H, R$_4$ is other than —H;

R$_{10}$ is —H or —C(O)CH$_3$; and pharmaceutically acceptable salts thereof when the compound contains either an acidic or basic functional group.

A further embodiment of the present invention are 7-halotaxol analogs of general Formula III wherein:

X is a halogen atom selected from the group consisting of —F, —Br, —Cl and —I;

R$_1$ is selected from the group consisting of —CH$_3$, —C$_6$H$_5$ or phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro;

R$_2$ is selected from the group consisting of —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —NHC(O)C$_3$–C$_8$cycloalkyl; and R$_3$, R$_4$, R$_5$ and R$_{10}$ are as defined above.

The compounds of Formula III include both the 7-α and 7-β configuration of the 7-halo substitution. Halo refers to —F, —Br, —Cl or —I.

In compounds of Formula III: X is preferably —F, and R$_3$ and R$_5$ are preferably —H, and R$_1$ is preferably phenyl or phenyl substituted with halo.

Additional preferred embodiments of Formula III include:
A compound according to Formula III wherein R$_4$ is —H and R$_5$ is —OH;
A compound according to Formula III wherein R$_4$ is other than —H and R$_5$ is —H;
A compound according to Formula III wherein R$_3$ is —H, and R$_1$ is Ph or substituted phenyl;
A compound according to Formula III wherein X is —F;
A compound according to Formula III wherein X is -α-F;
A compound according to Formula III wherein X is —F and R$_4$ is other than —H and R$_5$ is —H;
A compound according to Formula III wherein X is —F, R$_3$ is —H, and R$_1$ is Ph or substituted phenyl; and
A compound according to Formula III selected from the group consisting of 7-deoxy-7-fluorotaxol and 2'-[{(2,2,2-trichloroethyl)oxy}carbonyl]-7-deoxy-7-fluorotaxol; and
A compound according to Formula III, namely N-Debenzoyl-N-(t-butyl)aminocarbonyl-7-deoxy-7-fluoro-taxol.

An additional preferred embodiment of Formula III are compounds selected from the group consisting of 7-deoxy-7α-fluorotaxol, 7-deoxy-7β-fluorotaxol, 2'-[{(2,2,2-trichloroethyl)-oxy}carbonyl]-7-deoxy-7α-fluorotaxol and 2'-[{(2,2,2-trichloroethyl)oxy}carbonyl]-7-deoxy-7β-fluorotaxol.

A preferred embodiment of the subject invention is compounds of Formula III where R$_1$ is preferably phenyl or phenyl substituted with halo, R$_2$ is —NHC(O)NHC(CH$_3$)$_3$, R$_3$ and R$_5$ are —H, R$_4$ is —OH, and R$_{10}$ is —H or —COCH$_3$.

Examples of —NHC(O)C$_1$–C$_{10}$alkyl include —NHC(O)-n-pentyl and —NHC(O)CH(CH$_3$)CH$_2$CH$_3$.

Examples of C$_1$–C$_6$ alkyl include straight and branched alkyl chains, including for example methyl, ethyl, isopropyl, t-butyl, isobutyl and 2-methyl-pentyl.

Examples of C$_1$–C$_3$ alkoxy are methoxy, ethoxy, propoxy and isomeric forms thereof Halo refers to —F, —Br, —Cl or —I.

Examples of Formula II compounds of this invention include:
2'-[{(2,2,2-trichloroethyl)oxy}carbonyl]-7-deoxy-7β,8β-methano-taxol (Compound 14AA, Compound IIa);
7-deoxy-7β,8β-methano-taxol (Compound IIb);
2'-succinyl-7-deoxy-7β,8β-methano-taxol;
2'-(β-alanyl)-7-deoxy-7β,8β-methano-taxol formate;
2'-glutaryl-7-deoxy-7β,8β-methano-taxol;
2-[—C(O)(CH$_2$)$_3$C(O)NH(CH$_2$)$_3$N(CH$_3$)$_2$]-7-deoxy-7β,8β-methano-taxol;
2'-(β-sulfopropionyl)-7-deoxy-7β,8β-methano-taxol;
2'-(2-sulfoethylamido)succinyl-7-deoxy-7β,8β-methano-taxol;
2'-(3-sulfopropylamido)succinyl-7-deoxy-7β,8β-methano-taxol;
2'-(triethylsilyl)-7-deoxy-7β,8β-methano-taxol;
2'-(t-butyldimethylsilyl)-7-deoxy-7β,8β-methano-taxol;
2'-(N,N-diethylaminopropionyl)-7-deoxy-7β,8β-methano-taxol,
2'-(N,N-dimethylglycyl)-7-deoxy-7β,8β-methano-taxol;
2'-(glycyl)-7-deoxy-7β,8β-methano-taxol;
2'-(L-alanyl)-7-deoxy-7β,8β-methano-taxol;
2'-(L-leucyl)-7-deoxy-7β,8β-methano-taxol;
2'-(L-isoleucyl)-7-deoxy-7β,8β-methano-taxol;
2'-(L-valyl)-7-deoxy-7β,8β-methano-taxol;
2'-(L-phenylalanyl)-7-deoxy-7β,8β-methano-taxol;
2'-(L-prolyl)-7-deoxy-7β,8β-methano-taxol;
2'-(L-lysyl)-7-deoxy-7β,8β-methano-taxol;
2'-(L-glutamyl)-7-deoxy-7β,8β-methano-taxol;
2'-(L-arginyl)-7-deoxy-7β,8β-methano-taxol;
7-deoxy-7β,8β-methano-taxotere;
10-acetyl-7β,8β-methano-taxotere (Compound 23);
N-Debenzoyl-N-tetrahydrofuran-3-yloxycarbonyl-7-deoxy-7β,8β-methanotaxol;
N-Debenzoyl-N-(1-adamantoyl)-7-deoxy-7β,8β-methanotaxol;
N-Debenzoyl-N-phenylaminocarbonyl-7-deoxy-7β,8β-methanotaxol;
N-Debenzoyl-N-t-butylaminocarbonyl-7-deoxy-7β,8β-methanotaxol;
N-Debenzoyl-N-(1-methyl-1-cyclohexylanoyl)-7-deoxy-7β,8β-methanotaxol;
N-Debenzoyl-N-(1-phenyl-1-cyclopentanoyl)-7-deoxy-7β,8β-methanotaxol;
N-Debenzoyl-N-phthalimido-7-deoxy-7β,8β-methanotaxol;
N-Debenzoyl-N-t-butylaminothiocarbonyl-7-deoxy-7β,8β-methanotaxol;
N-Debenzoyl-N-t-amyloxycarbonyl-7-deoxy-7β,8β-methanotaxol;
N-Debenzoyl-N-neopentyloxycarbonyl-7-deoxy-7β,8β-methanotaxol;
N-Debenzoyl-N-(2-chloro-1,1-dimethylethyl)oxycarbonyl-7-deoxy-7β,8β-methanotaxol;
N-Debenzoyl-N-(3-methyl-3-pentyl)oxycarbonyl-7-deoxy-7β,8β-methanotaxol;
3'-desphenyl-3'-(2-furyl)-7-deoxy-7β,8β-methanotaxol;
3'-desphenyl-3'-(2-thienyl)-7-deoxy-7β,8β-methanotaxol;

3'-desphenyl-3'-(1-naphthyl)-7-deoxy-7β,8β-methanotaxol;
3'-desphenyl-3'-(2-naphthyl)-7-deoxy-7β,8β-methanotaxol;
3'-desphenyl-3'-(4-methoxyphenyl)-7-deoxy-7β,8β-methanotaxol;
3'-desphenyl-3'-(4-chlorophenyl)-7-deoxy-7β,8β-methanotaxol;
3'-desphenyl-3'-(4-bromophenyl)-7-deoxy-7β,8β-methanotaxol;
3'-desphenyl-3'-(3,4-methylenedioxyphenyl)-7-deoxy-7β,8β-methanotaxol;
3'-desphenyl-3'-(3,4-dimethoxyphenyl)-7-deoxy-7β,8β-methanotaxol;
3'-desphenyl-3'-(4-nitrophenyl)-7-deoxy-7β,8β-methanotaxol;
3'-desphenyl-3'-(4-fluorophenyl)-7-deoxy-7β,8β-methanotaxol;
N-debenzoyl-N-(4-bromobenzoyl)-7-deoxy-7β,8β-methanotaxol;
N-debenzoyl-N-(4-methylbenzoyl)-7-deoxy-7β,8β-methanotaxol;
N-debenzoyl-N-(4-t-butylbenzoyl)-7-deoxy-7β,8β-methanotaxol;
N-debenzoyl-N-(4-methoxybenzoyl)-7-deoxy-7β,8β-methanotaxol;
N-debenzoyl-N-(4-fluorobenzoyl)-3'-desphenyl-3'-(4-fluorophenyl)-7-deoxy-7β,8β-methanotaxol;
N-debenzoyl-N-(4-fluorobenzoyl)-7-deoxy-7β,8β-methanotaxol;
N-debenzoyl-N-(4-methylbenzoyl)-3'-desphenyl-3'-(4-chlorophenyl)-7-deoxy-7β,8β-methanotaxol;
N-debenzoyl-N-(4-chlorobenzoyl)-3'-desphenyl-3'-(4-fluorophenyl)-7-deoxy-7β,8β-methanotaxol;
N-debenzoyl-N-(4-bromobenzoyl)-3'-desphenyl-3'-(4-fluorophenyl)-7-deoxy-7β,8β-methanotaxol;
N-debenzoyl-N-(4-methylbenzoyl)-3'-desphenyl-3'-(fluorophenyl)-7-deoxy-7β,8β-methanotaxol;
N-debenzoyl-N-(4-fluorobenzoyl)-3'-desphenyl-3'-(4-methoxyphenyl)-7-deoxy-7β,8β-methanotaxol;
N-debenzoyl-N-(4-methylbenzoyl)-3'-desphenyl-3'-(4-methoxyphenyl)-7-deoxy-7β,8β-methanotaxol;
N-debenzoyl-N-(4-fluorobenzoyl)-3'-desphenyl-3'-(4-chlorophenyl)-7-deoxy-7β,8β-methanotaxol;
N-debenzoyl-N-(4-chlorobenzoyl)-3'-desphenyl-3'-(4-chlorophenyl)-7-deoxy-7β,8β-methanotaxol;
N-debenzoyl-N-(4-bromobenzoyl)-3'-desphenyl-3'-(4-chlorophenyl)-7-deoxy-7β,8β-methanotaxol;
N-debenzoyl-N-(4-t-butylbenzoyl)-3'-desphenyl-3'-(4-chlorophenyl)-7-deoxy-7β,8β-methanotaxol;
N-debenzoyl-N-(4-t-butylbenzoyl)-3'-desphenyl-3'-(4-fluorophenyl)-7-deoxy-7β,8β-methanotaxol;
N-debenzoyl-N-(chlorobenzoyl)-3'-desphenyl-3'-(4-methoxyphenyl)-7-deoxy-7β,8β-methanotaxol;
N-debenzoyl-N-(4-bromobenzoyl)-3'-desphenyl-3'-(4-methoxyphenyl)-7-deoxy-7β,8β-methanotaxol;
N-debenzoyl-N-(4-t-butylbenzoyl)-3'-desphenyl-3'-(4-methoxyphenyl)-7-deoxy-7β,8β-methanotaxol;
N-debenzoyl-N-(4-methoxybenzoyl)-3'-desphenyl-3'-(4-methoxyphenyl)-7-deoxy-7β,8β-methanotaxol;
N-debenzoyl-N-(t-butyl)aminocarbonyl-7-deoxy-7β,8β-methano-taxol (Compound 29); and
pharmaceutically acceptable salts thereof when the compound contains either an acidic or basic functional group.

Examples of Formula III compounds of this invention include:
2'-[{(2,2,2-trichloroethyl)oxy}carbonyl]-7-deoxy-7-fluorotaxol (Compound 13AA, IIIc);
7-deoxy-7-fluorotaxol (Compound IIIb);
2'-succinyl-7-deoxy-7-fluorotaxol;
2'-(β-alanyl)-7-deoxy-7-fluorotaxol formate;
2'-glutaryl-7-deoxy-7-fluorotaxol;
2'-[—C(O)(CH$_2$)$_3$C(O)NH(CH$_2$)$_3$N(CH$_3$)$_2$]-7-deoxy-7-fluorotaxol;
2'-(β-sulfopropionyl)-7-deoxy-7-fluorotaxol;
2'-(2-sulfoethylamido)succinyl-7-deoxy-7-fluorotaxol;
2'-(3-sulfopropylamido)succinyl-7-deoxy-7-fluorotaxol;
2'-(triethylsilyl)-7-deoxy-7-fluorotaxol;
2'-(t-butyldimethylsilyl)-7-deoxy-7-fluorotaxol;
2'-(N,N-diethylaminopropionyl)-7-deoxy-7-fluorotaxol;
2'-(N,N-dimethylglycyl)-7-deoxy-7-fluorotaxol;
2'-(glycyl)-7-deoxy-7-fluorotaxol;
2'-(L-alanyl)-7-deoxy-7-fluorotaxol;
2'-(L-leucyl)-7-deoxy-7-fluorotaxol;
2'-(L-isoleucyl)-7-deoxy-7-fluorotaxol;
2'-(L-valyl)-7-deoxy-7-fluorotaxol;
2'-(L-phenylalanyl)-7-deoxy-7-fluorotaxol:
2'-(L-prolyl)-7-deoxy-7-fluorotaxol;
2'-(L-lysyl)-7-deoxy-7-fluorotaxol;
2'-(L-glutamyl)-7-deoxy-7-fluorotaxol;
2'-(L-arginyl)-7-deoxy-7-fluorotaxol;
7-deoxy-7-fluorotaxotere;
10-acetyl-7-deoxy-7-fluorotaxotere (Compound 20);
N-Debenzoyl-N-tetrahydropyran-4-yloxycarbonyl-7-deoxy-7-fluorotaxol;
N-Debenzoyl-N-pivaloyl-7-deoxy-7-fluorotaxol;
N-Debenzoyl-N-n-hexylaminocarbonyl-7-deoxy-7-fluorotaxol;
N-Debenzoyl-N-t-butylaminocarbonyl-7-deoxy-7-fluorotaxol;
N-Debenzoyl-N-(1-methyl-1-cyclohexylanoyl)-7-deoxy-7-fluorotaxol;
N-Debenzoyl-N-(1-phenyl-1-cyclopentanoyl)-7-deoxy-7-fluorotaxol;
N-Debenzoyl-N-phthalimido-7-deoxy-7-fluorotaxol;
N-Debenzoyl-N-t-butylaminothiocarbonyl-7-deoxy-7-fluorotaxol;
N-Debenzoyl-N-t-amyloxycarbonyl-7-deoxy-7-fluorotaxol;
N-Debenzoyl-N-neopentyloxycarbonyl-7-deoxy-7-fluorotaxol;
N-Debenzoyl-N-(2-chloro-1,1-dimethylethyl)oxycarbonyl-7-deoxy-7-fluorotaxol;
N-Debenzoyl-N-(3-methyl-3-pentyl)oxycarbonyl-7-deoxy-7-fluorotaxol;
3'-desphenyl-3'-(2-furyl)-7-deoxy-7-fluorotaxol;
3'-desphenyl-3'-(2-thienyl)-7-deoxy-7-fluorotaxol;
3'-desphenyl-3'-(1-naphthyl)-7-deoxy-7-fluorotaxol;
3'-desphenyl-3'-(2-naphthyl)-7-deoxy-7-fluorotaxol;
3'-desphenyl-3'-(4-methoxyphenyl)-7-deoxy-7-fluorotaxol;
3'-desphenyl-3'-(4-chlorophenyl)-7-deoxy-7-fluorotaxol;
3'-desphenyl-3'-(4-bromophenyl)-7-deoxy-7-fluorotaxol;
3'-desphenyl-3'-(3,4-methylenedioxyphenyl)-7-deoxy-7-fluorotaxol;
3'-desphenyl-3'-(3,4-dimethoxyphenyl)-7-deoxy-7-fluorotaxol;
3'-desphenyl-3'-(4-nitrophenyl)-7-deoxy-7-fluorotaxol;
3'-desphenyl-3'-(4-fluorophenyl)-7-deoxy-7-fluorotaxol;
N-debenzoyl-N-(4-bromobenzoyl)-7-deoxy-7-fluorotaxol;
N-debenzoyl-N-(4-methylbenzoyl)-7-deoxy-7-fluorotaxol:
N-debenzoyl-N-(4-t-butylbenzoyl)-7-deoxy-7-fluorotaxol;

N-debenzoyl-N-(4-methoxybenzoyl)-7-deoxy-7-fluorotaxol;

N-debenzoyl-N-(4-fluorobenzoyl)-3'-desphenyl-3'-(4-fluorophenyl)-7-deoxy-7-fluorotaxol;

N-debenzoyl-N-(4-fluorobenzoyl)-7-deoxy-7-fluorotaxol;

N-debenzoyl-N-(4-methylbenzoyl)-3'-desphenyl-3'-(4-chlorophenyl)-7-deoxy-7-fluorotaxol;

N-debenzoyl-N-(4-chlorobenzoyl)-3'-desphenyl-3'-(4-fluorophenyl)-7-deoxy-7-fluorotaxol;

N-debenzoyl-N-(4-bromobenzoyl)-3'-desphenyl-3'-(4-fluorophenyl)-7-deoxy-7-fluorotaxol;

N-debenzoyl-N-(4-methylbenzoyl)-3'-desphenyl-3'-(4-fluorophenyl)-7-deoxy-7-fluorotaxol;

N-debenzoyl-N-(4-fluorobenzoyl)-3'-desphenyl-3'-(4-methoxyphenyl)-7-deoxy-7-fluorotaxol;

N-debenzoyl-N-(4-methylbenzoyl)-3'-desphenyl-3'-(4-methoxyphenyl)-7-deoxy-7-fluorotaxol;

N-debenzoyl-N-(4-fluorobenzoyl)-3'-desphenyl-3'-(4-chlorophenyl)-7-deoxy-7-fluorotaxol;

N-debenzoyl-N-(4-chlorobenzoyl)-3'-desphenyl-3'-(4-chlorophenyl)-7-deoxy-7-fluorotaxol;

N-debenzoyl-N-(4-bromobenzoyl)-3'-desphenyl-3'-(4-chlorophenyl)-7-deoxy-7-fluorotaxol;

N-debenzoyl-N-(4-t-butylbenzoyl)-3'-desphenyl-3'-(4-chlorophenyl )-7-deoxy-7-fluorotaxol;

N-debenzoyl-N-(4-t-butylbenzoyl)-3'-desphenyl-3'-(4-fluorophenyl)-7-deoxy-7-fluorotaxol;

N-debenzoyl-N-(4-chlorobenzoyl)-3'-desphenyl-3'-(4-methoxyphenyl)-7-deoxy-7-fluorotaxol;

N-debenzoyl-N-(4-bromobenzoyl)-3'-desphenyl-3'-(4-methoxyphenyl)-7-deoxy-7-fluorotaxol;

N-debenzoyl-N-(4-t-butylbenzoyl)-3'-desphenyl-3'-(4-methoxyphenyl)-7-deoxy-7-fluorotaxol;

N-debenzoyl-N-(4-methoxybenzoyl)-3'-desphenyl-3'-(4-methoxyphenyl)-7-deoxy-7-fluorotaxol;

N-debenzoyl-N-(t-butyl)aminocarbonyl-7-deoxy-7-fluoro-taxol (Compound 28); and pharmaceutically acceptable salts thereof when the compound contains either an acidic or basic functional group.

The present invention also provides a process for preparing oxazolidines of Formula 5

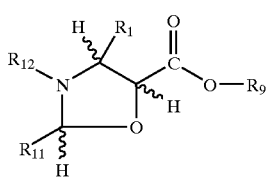

in which $R_1$ is as defined above;

$R_9$ is selected from $C_1$–$C_6$alkyl; $R_{11}$ is phenyl substituted with —$(OC_1$–$C_2alkyl)_n$ where n is 1 to 3;

$R_{12}$ is selected from the group consisting of —C(O)H, —C(O)$C_1$–$C_{10}$alkyl (preferably —C(O)$C_4$–$C_6$alkyl), —C(O)phenyl, —C(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —C(O)C($CH_3$)=CH$CH_3$, —C(O)OC($CH_3$)$_3$, —C(O)OCH$_2$phenyl, —SO$_2$-4-methylphenyl, —C(O)(CH$_2$)$_3$COOH, —C(O)-4-(SO$_3$H)phenyl, —C(O)-1-adamantyl, —C(O)O-3-tetrahydrofuranyl, —C(O)O-4-tetrahydropyranyl, —C(O)CH$_2$C(CH$_3$)$_3$, —C(O)C(CH$_3$)$_3$, —C(O)OC$_1$–C$_{10}$alkyl, —C(O)NHC$_1$–C$_{10}$alkyl, —C(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, or —C(O)$C_3$–$C_8$cycloalkyl, —C(O)C(CH$_2$CH$_3$)$_2$CH$_3$, —C(O)C(CH$_3$)$_2$CH$_2$Cl, —C(O)C(CH$_3$)$_2$CH$_2$CH$_3$, —C(O)-1-phenyl-1-cyclopentyl, —C(O)-1-methyl-1-cyclohexyl, —C(S)NHC(CH$_3$)$_3$, —C(O)NHCC(CH$_3$)$_3$ or —C(O)NHPh;

which comprises reacting a hydroxy-amine of Formula 3

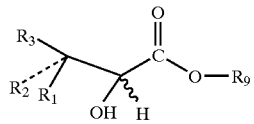

in which $R_1$ and $R_3$ are as defined above and $R_2$ is selected from the group consisting of —NHC(O)H, —NHC(O)$C_1$–$C_{10}$alkyl (preferably —NHC(O)$C_4$–$C_6$alkyl), —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C(CH$_3$)=CHCH$_3$, —NHC(O)OC(CH$_3$)$_3$, —NHC(O)OCH$_2$phenyl, —NHSO$_2$-4-methylphenyl, —NHC(O)(CH$_2$)$_3$COOH, —NHC(O)-4-(SO$_3$H)phenyl, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, or —NHC(O)$C_3$–$C_8$cycloalkyl, —NHC(O)C(CH$_2$CH$_3$)$_2$CH$_3$, —NHC(O)C(CH$_3$)$_2$CH$_2$Cl, —NHC(O)C(CH$_3$)$_2$CH$_2$CH$_3$, —NHC(O)-1-phenyl-1-cyclo-pentyl, —NHC(O)-1-methyl-1-cyclohexyl, —NHC(S)NHC(CH$_3$)$_3$, —NHC(O)NHCC(CH$_3$)$_3$ or —NHC(O)NHPh;

with (1) an electron rich benzaldehyde of Formula 4A

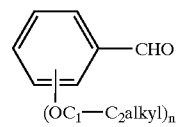

or (2) an electron rich acetal of Formula 4

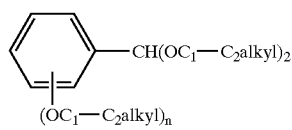

where n is 1–3.

In addition, the present invention provides a process of preparing

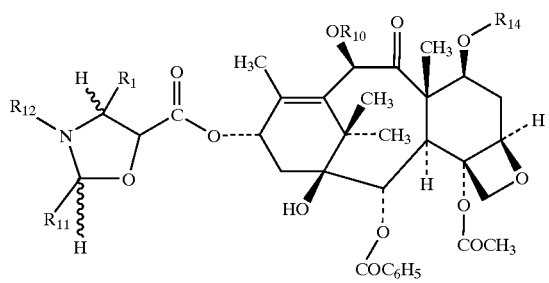

which comprises reacting an oxazolidine free acid of Formula 7

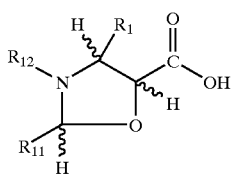

with a baccatin compound of Formula 8

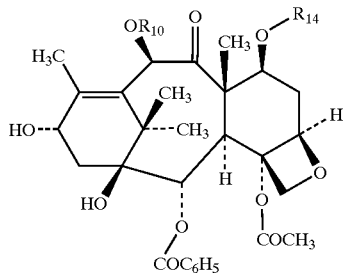

in the presence of a dehydrating agent Wherein $R_{10}$ and $R_{14}$, being the same or different, are selected from the group consisting of —C(O)$C_1$-$C_6$alkyl (preferably —C(O)$CH_3$), —C(O)O$C_1$-$C_6$alkyl, —C(O)OCH$_2$CX$_3$ where X is Halo, —C(O)OCH$_2$CH$_2$SiR$_{20}$ (where $R_{20}$ is $C_1$-$C_6$alkyl), or —Si(R$_{20}$)$_3$; $R_{11}$ and $R_{12}$ are as defined above.

The compounds of the present invention are prepared by the method(s) as shown in Charts A, A', B and C.

The starting point for the method shown in Chart A is a taxol or taxol analog derivative A-1. Reaction of the A-1 compound with a reagent such as diethylaminosulfur trifluoride (DAST), dimethylaminosulfur trifluoride (methylDAST), bis(dimethylamino)sulfur difluoride. bis (diethylamino)sulfur difluoride, or (diethylamino)(dimethylamino)sulfur difluoride, gives the 7-deoxy-7β,8β-methano analog A'-2 (CHART A-II) as well as 7-deoxy-7-fluoro analog A"-2 (CHART A-III). The preferred method for this conversion is with DAST or methylDAST. The reaction with DAST or methylDAST is carried out in an aprotic solvent such as methylene chloride (CH$_2$Cl$_2$), chloroform (CHCl$_3$), fluorotrichloromethane (Freon 11®), ethylene glycol dimethyl ether (glyme), 2-methoxyethyl ether (diglyme), pyridine, hydrocarbons such as pentane. hexane, or isooctane, tetrahydrofuran (THF), benzene, toluene, xylene. The preferred solvent is methylene chloride. The reaction may be performed in a range of temperature from −100° C. to 100° C. or above. Generally, the reaction is begun under conditions of low temperature, e.g., −78° C., and then is allowed to proceed at a higher temperature, e.g., 25° C. The reaction is quenched with water, the crude product is isolated by standard extraction methods, and is purified by standard chromatographic methods and/or by crystallization. [When $R_4$ is —OC(O)OCH$_2$C(Cl)$_3$, treatment of A'-2 (CHART A-II) with activated zinc in methanol-acetic acid solution will serve to remove the protecting group and produce the desired 7-deoxy-7β,8β-methano-taxol or 7-deoxy-7β,8β-methano-taxol analog A'-3 (CHART A-II). When $R_4$ is —OC(O)OCH$_2$C(Cl)$_3$, treatment of A"-2 (CHART A-III) with activated zinc in methanol-acetic acid solution will serve to remove the protecting group and produce the desired 7-deoxy-7-fluorotaxol or 7-deoxy-7-fluorotaxol analog A"-3 (CHART A-III).] Methodologies for the addition of various protecting groups to taxol or to taxol analogs and for the removal of such groups are found in: Greene, T. W. and P. G. M. Wuts, "Protective Groups in Organic Synthesis," 2nd Ed., pages 10–142, Wiley, N.Y. 1991.

Alternatively, the compounds (Formula II) of this invention may be prepared treatment of a 7-epi taxol derivative with DAST in dichloromethane as disclosed in Chen et al., Serendipitous Synthesis of a Cyclopropane-Containing Taxol Analog via Anchimeric Participation of an Unactivated Angular Methyl Group. Advance ACS Abstracts, Vol 1, No. 2., Jul. 15, 1993 and J. Org. Chem., 1993, 56, 4520, (Aug. 13, 1993).

The compounds (Formula II) of this invention may also be prepared by the method shown in Chart B-II. In this method, when Z'=H in Formula II (when Z'=H; $R_{10}$=—C(O)CH$_3$, this Formula II structure is also known as baccatin III), treatment of baccatin III or a suitably protected (Z'=troc) baccatin III molecule B-1 by the method described above will produce 7-deoxy-7β,8β-methano-baccatin III (B-2) after removal of the protecting group. Reaction of B-2 with an activated side chain precursor B-3 by one of several methods described in the literature (see: Kingston, D. G. I. Pharmac. Ther., 1991, 52, 1–34; Commerçon, A.; Bézard, D.; Bernard, F.; Bourzat, J. D. Tetrahedron Lett., 1992, 33, 5185; Georg, G. I.; Cheruvallath, Z. S.; Himes, R. H.; Mejillano, M. R. BioMed. Chem. Lett. 1992, 2, 295) gives B-4. For example. coupling of 7-deoxy-7β,8β-methano-baccatin III with (4S,5R)-N-BOC-2,2-dimethyl-4-phenyl-5-oxazolidinecarboxylic acid followed by subsequent transformation according to the procedures of Commerçon, et. al., gives an intermediate that is useful for further transformations into 7-deoxy-7β,8β-methano-taxol, 7-deoxy-7β,8β-methano-taxotere [compound of formula II, wherein $R_1$=Ph; $R_2$=NHC(O)O-t-Bu; $R_3$=$R_5$=H; $R_4$=$R_6$=OH;], and other 7-deoxy-7β,8β-methano-taxol analogs.

The compounds (Formula II) of this invention may also be prepared from taxol or taxol analogs having a substituent at C-7 with the properties of a good leaving group, e.g., (a) a diazonium ion precursor such as —NH$_2$, (b) a sulfonate ester, —OSO$_2$R (where R is a group such as, for example, —CH$_3$, —CF$_3$, $C_6H_4$-(p)-CH$_3$, —$C_6H_4$-(p)-Br, —$C_6H_4$-(p)-NO$_2$, or (c) one of the halogens, iodine or bromine (—I or —Br). A C-7 amine substituent upon reaction with nitrous acid (HNO$_2$) is converted to a diazonium ion. The diazonium ion undergoes spontaneous loss of nitrogen resulting in formation of the 7β,8β-methano functional group. A C-7 sulfonate ester when dissolved in a polar solvent (such as methanol-water, ethanol-water, trifluoroacetic acid) undergoes ionization resulting in formation of the 7β,8β-methano functional group. The ionization of the C-7 sulfonate ester may be enhanced by the addition of a non-nucleophilic base [such as potassium carbonate, potassium bicarbonate, 1,4-diazabicyclo [2.2.2] octane (DABCO)] to the reaction medium. A C-7 iodide or bromide undergoes ionization and formation of the 7β,8β-methano functional group in a polar solvent in the presence of metal salts, particularly silver salts such as silver acetate, silver trifluoroacetate, silver tetrafluoro-borate.

The compounds (Formula III) of this invention may also be prepared by the method shown in Chart B-III. In this method, when Z'=H in Formula II (when Z'=H; $R_{10}$=—COCH$_3$, this Formula II structure is also known as baccatin III), fluorination of baccatin III or a suitably protected (Z'=troc) baccatin III molecule B-1 by the method described above will produce 7-fluorobaccatin III (B-2) after removal of the protecting group. Reaction of B-2 with an activated side chain precursor B-3 by one of several methods described in the literature (see: Kingston, D. G. I. Pharmac. Ther., 1991, 52, 1–34; Commerçon, A.; Bézard, D.; Bernard, F.; Bourzat, J. D. Tetrahedron Lett., 1992, 33, 5185; Georg, G. I.; Cheruvallath, Z. S.; Himes, R. H.; Mejillano, M. R.

*BioMed. Chem. Lett.* 1992, 2, 295) gives B-4. For example, coupling of 7-fluorobaccatin III with (4S,5R)-N-BOC-2,2-dimethyl-4-phenyl-5-oxazolidinecarboxylic acid followed by subsequent transformation according to the procedures of Commerçon, et.al., gives an intermediate that is useful for further transformations into 7-deoxy-7-fluorotaxol, 7-deoxy-7-fluorotaxotere [compound of formula III, wherein $R_1$=Ph; $R_2$=NHC(O)O-t-Bu; $R_3$=$R_5$=H; $R_4$=OH; $R_{10}$=—C(O)CH$_3$], and other 7-deoxy-7-fluorotaxol analogs.

The compounds (Formula I including Formula II and III) of this invention may be prepared by a new, improved procedure as shown in Charts A', B and C. The preparation of 3-azido-2-hydroxy-carboxylic acid esters 1 may be prepared as described in the literature (see Denis, J-N.; Correa, A.; Greene, A. E. *J. Org. Chem.,* 1990, 55, 1957). These materials are readily hydrogenated to the free amines 2, even though the literature intentionally avoids this intermediate by preparing the hydroxy-acylated intermediate prior to the reduction of the azide. The amine 2 is sufficiently stable that no problem is encountered in isolating it and directly using it to prepare the N-acylated free hydroxy compounds 3. Compounds 3 have been utilized by protection of the hydroxy group, hydrolysis of the ester to the acid, and condensation directly with a baccatin III derivative or after conversion to the oxazinone (European Patent 0 428 376 A1, U.S. Pat. No. 4,362,35). These procedures are distinctly inferior because they require large excesses of the acylating agent and generally do not proceed beyond about 60% completion. Procedures have also been described using a beta-lactam intermediate but these also require large excesses of reagent or the introduction of very strong bases such as LDA which makes them more difficult to perform and unsuitable for certain analogs (Ojima, I.; Habus, I.; Zhao, M.; George, G. I.; Jayasinghe, L. R. *J. Org. Chem.,* 1991, 56, 1681, EP 0 400 971 A2). A very effective condensation procedure involving the conversion of the hydroxy-amine derivative 3 to an oxazolidine with 2 non hydrogen substituents at the 2 position was described by Commerçon, A.; Bézard, D.; Bernard, F.; Bourzat, J. D. in *Tetrahedron Lett.,* 1992, 33, 5185 and Patent WO 92/09589. The condensation proceeds in very high yield but the removal of the protecting group requires sufficiently strong acid that sensitive taxol analogs are destroyed under the deprotection conditions. We have modified and improved this procedure by formation of the oxazolidines 5 not with a ketone, as the above workers have used but, with an electron rich benzaldehyde 4. The oxazolidines derived from the benzaldehyde 4 are produced as a mixture of diastereomers but these have been separated in some cases and the diastereomers have been shown to be equally useful when carried on in the synthesis. The oxazolidines 5 are readily hydrolyzed to the salts 6 and the acids 7. The acid is labile and needs to be used shortly after preparation. Both oxazolidine isomers are equally effective in the condensation reaction with the protected baccatins 8 giving an excellent yield of the oxazolidine protected taxol analogs 9. More importantly, both oxazolidine isomers from these electron rich benzaldehydes are readily hydrolyzed under very mild acid conditions allowing deprotection without causing undesired transformations of highly acid sensitive taxol derivatives such as 10 which are the subject of this invention. There are references to the use of electron rich aldehydes for the protection of 1,2-diols as dioxolanes but no previous reference to the use of such aldehydes for the protection of 2-hydroxy protected amines. The deprotection may be carried out such that both the oxazolidine and the 7 protected hydroxyl of 9 are removed at the same time or each may be removed independently. Additionally described is the deprotection of selected urethane analogs 10 to the free amine 11 (Chart B). These are then reconverted to a variety of amine acylated analogs 10.

The conversion of azide 1 to the amine 2 is effected by reduction as is known in the art. Thus, the reaction may be carried out by hydrogenation in the presence of a variety of hydrogenation catalysts such as palladium, platinum, rhodium, or ruthenium. Alternatively, the azide may be reduced by treatment with a phosphine such as triphenyl or tributyl phosphine or by an acid such as hydrochloric, sulfuric, trifluoroacetic or hydrobromic in the presence of a metal such as zinc, iron, or tin. These reactions may be effected in a solvent such as ethanol, methanol, ethyl acetate, methyl t-butyl ether or tetrahydrofuran and the like. The conversion of amine 2 to its acylated derivative 3 is effected by treatment of the amine in pyridine or a non-basic solvent such as methylene chloride or tetrahydrofuran containing a tertiary amine such as triethyl amine or ethyl diisopropyl amine with an acylation agent. If 3 is a urethane, 2 is treated with an agent such as benzylchloroformate, 2,2,2-trichloroethoxycarbonyl chloride, di-tert-butyldicarbonate, or other urethane forming agent as is known in the art. If 3 is an amide, 2 is treated with an acylating agent such as an acyl halide, and acyl anhydride, or other acylating agent as is known in the art. If 3 is a urea or a thiourea, 2 is treated with an agent such as alkyl or aryl isocyanate, alkyl or aryl isothiocyanate, or other urea or thiourea forming agent as is known in the art.

The hydroxy amide or urethane 3 is converted to the oxazolidine 5 by treatment with an electron rich benzaldehyde or its acetal such as dimethyl or diethyl acetal 4 and an acid catalyst such as p-toluene sulfonic acid, pyridinium p-toluene sulfonate or other acid catalysts known in the art in a solvent such as tetrahydrofuran, toluene, methylene chloride, or other aprotic solvent. Examples of electron rich benzaldehydes include but are not limited to 2-, 3-, 4-methoxybenzaldehyde; 2,4-, 3,5-, 2,5-dimethoxybenzaldehyde; 2,4,6-trimethoxybenzaldehyde; and 4-ethoxybenzaldehyde. The preferred benzaldehyde is 2,4-dimethoxybenzaldehyde. The oxazolidine formation is generally carried out by heating to reflux to distill both the solvent and to carry off the evolved water or alcohol. The ester of 5 is hydrolyzed to the salt 6 by treatment with an alkali or quaternerary amine hydroxide or by an alkali carbonate or other base as known in the art in a solvent such as water, methanol, ethanol, or other protic solvent. The reaction may by carried out from −78° C. to 100° C. The product 6 is stable and may be isolated by evaporation of the solvents and stored as a solid or the reaction may be used directly to convert 6 to the acid 7 by treatment with acid. Generally, 7 is obtained by treating an aqueous solution of 6 in a separatory funnel with sufficient acid such as hydrochloric, sulfuric, potassium hydrogen sulfate, or the like, and partitioning the desired acid into an organic solvent such as ethyl acetate, methylene chloride, ether, or the like and evaporation of the solvent. The resultant acid 7 is sufficiently pure and stable for use in the next reaction but in general is not sufficiently stable for long term storage. The acid 7 is condensed with the baccatin derivative 8 to form the ester 9 with a dehydrating agent. Most preferred for this procedure is a carbodiimide such as dicyclohexyl carbodiimide, diisopropyl carbodiimide, di-p-tolyl carbodiimide, ethyl dimethylaminopropyl carbodiimide hydrochloride salt, or the like, and a basic catalyst, preferably 4-dimethylaminopyridine. The reaction is generally carried out in an aprotic solvent such as toluene, benzene, tetrahydrofuran, dioxane, or the like at 25° C. to 100° C. Other dehydration procedures for the formation of 9 may be used such as conversion of 7 to its mixed ester with a sulfonic acid such as with toluenesulfonyl chloride or benzenesulfonyl chloride, or formation of the acid halide from the dried 6 in the presence of oxalyl chloride as is known in the art for acid sensitive carboxylic acids. The oxazolidines 9 may be deprotected so that the protecting oxazolidine and the groups blocking the hydroxyl at the baccatin 7 position are individually removed in either order or both removed together depending on the protecting group at the 7 position and on the reaction conditions. If $R_{14}$ is an acid labile group such as a silyl ether, then hydrolysis of the oxazolidine may be run under mild acid conditions and leads to the 7 position deprotection as well, giving 10MZ directly. Conditions for such conversions include hydrolysis in aqueous acetic acid, aqueous alcoholic acid of 0.01 to 0.1 N at 0° C. to 50° C., or alcoholic acid of 0.01 to 0.1 N at 0° C. to 50° C. Alternatively, the protection at the 7 position could be removed at a second step if it is not acid labile. For example, the trichloroethoxycarbonyl group at position 7 could be removed from 10MY (Chart B) by reduction as is known in the art to give 10MZ. Depending on the nature of the protecting group on the nitrogen (i.e. $R_2$ or $R_3$) of 10MZ (Chart B) the protecting group can be removed to give 11Z. For example, when $R_2$ is $PhCH_2OC(O)NH$, it may be removed by mild hydrogenolysis. Conditions for such conversions include reduction with hydrogen over a metal catalyst such as palladium in a solvent such as ethanol or ethyl acetate at room temperature and from one to three atmospheres of pressure. Other methods are known in the art. The resultant amine 11Z may be reconverted to a amide or urethane 10MZ (Chart B) by acylation procedures as described for the conversion of 2 to 3 above. The product 10MZ may be protected on the 2' hydroxyl to give 12MZ (Chart B). For example, the 2' hydroxyl may be acylated with trichloroethoxycarbonyl chloride in pyridine or other aromatic amine solvents, or in a non basic solvent such as toluene, methylene chloride, or tetrahydrofuran containing a tertiary amine base. The reaction may be run at −50° C. to 100° C. Other methods for such acylations are well known in the art.

The reaction of taxol, taxol analogs 10MZ ($R_{15}$ is acetate or other suitable acyl moiety), baccatin III, or baccatin III analogs 8 ($R_6$ is acetate or other suitable acyl moiety) with hydrazine comprises a particularly advantageous method for preparation of 10-deacetyl taxol, 10-deacyl taxol analogs (10MZ, $R_{15}$ =H), 10-deacetyl baccatin III, and 10-deacyl baccatin II analogs (8, $R_6$ =H). Whereas the reported method (Samaranayake. G.; et. al., *J. Org. Chem.*, 1991, 56, 5114) for removal of the acyl group from this position of taxol and baccatin structures, i.e., zinc bromide in methanol, gives a number of other products in addition to the desired deacylation NO. 2product, the reaction with hydrazine gives almost exclusively the desired deacylation product. The reaction may be performed at room temperature in an organic solvent and usually requires as little time as 15 min or as much as 24 hr, depending on the substrate. The preferred solvent for the reaction is 95% ethanol and 98% hydrazine is the preferred form of the reagent.

Preparation No. 1: Preparation of (2R,3S)-β-phenyl isoserine methyl ester (2)

The (2R,3S)-3-azido-2-hydroxy-3-phenylpropionic acid methyl ester (1, 0.5 g) is hydrogenated over 10% palladium on carbon (0.1 g) in ethanol at atmospheric pressure for 1 hour. The reaction is filtered and evaporated to yield the desired amine. Mp 106–108° C.

NMR(CDCl$_3$, TMS): δ 2.1 (bs); 3.80 (s, 3H); 4.31 (m, 2H); 7.28–7.45 (m, 5H).

Preparation No. 2: Preparation of (4S,5R)-N-Benzoyl-2-(2,4-dimethoxyphenyl)-4-phenyl-5-oxazolidinecarboxylic acid methyl ester (5Aa & 5Ab)

N-Benzoyl-βphenyl isoserine methyl ester (3A, 0.5 g, 1.67 mM) is dissolved in dry THF (10 mL) and benzene (10 mL) and the solution treated with 2,4-dimethoxy benzaldehyde dimethyl acetal (4, 0.420 g, 1.98 mM) and pyridinium p-toluenesulfonate (12 mg) and the solution warmed to reflux. After 30 minutes the reaction is cooled to RT and allowed to stand overnight. It is then again warmed to slowly distill off ½ of the solvent over 1 hr. TLC shows the reaction to be finished at this point. The reaction is concentrated in vacuo and the residue chromatographed over 50 g silica gel packed in (5-95) methanol-toluene. The column is eluted with methanol-toluene (5-95). Fractions of 12 mL are collected. The product elutes as a mixture. Thus, fractions containing both 5Aa & 5Ab are recombined and evaporated. The residue (0.90 g) is rechromatographed over silica gel (100 g) The column is eluted with ethyl acetate-toluene (500 mL of 15-85 and 500 mL of 20-80). Fractions of 20 mL are collected and analyzed by TLC. The fractions containing each 5Aa & 5Ab are combined and evaporated under vacuum.

less polar isomer 5Aa mixture of less polar and more polar isomers 5Aa and 5Ab more polar 5Ab Isomer 5Ab is crystallized from EtOAc to give white crystals (142 mg, mp 138–141° C.).

Data for 5Aa:

TLC: silica gel; 20% EtOAc-80% toluene; $R_f$: 0.50 $^1$H NMR (CDCl$_3$; TMS): δ; 3.69 (s, 3H); 3.77 (s, 3H); 3.86 (s, 3H); 4.93 (d, 1H); 5.6 (brs, 1H); 6.28–6.37 (m, 2H); 6.90 (s, 1H); 7.03 (d, 1H); 7.15–7.55 (m, 9);.

Data for 5Ab:

TLC: silica gel; 20% EtOAc-80% toluene; $R_f$: 0.41. $^1$H NMR (CDCl$_3$; TMS): δ 3.62 (bs, 3H); 3.75 (brs, 6H); 4.65 (d, 1H); 5.68 (bs, 1H); 6.2–6.5 (m, 2H); 6.8–7.55 (m, 11H). UV: EtOH; 229 (16,000), 277 (3,240), 281sh (3,170). Elemental analysis: Calculated: C, 69.79; H, 5.63; N, 3.13. Found: C, 69.61; H, 5.61; N, 2.93.

Preparation No. 3: Preparation of (4S,5R)-N-benzyl-2-(2,4 dimethoxyphenyl)-4-phenyl-5-oxazolidine carboxylic acid potassium salt. 6Ab (4S,5R)-N-benzyl-2-(2,4 dimethoxyphenyl)-4-phenyl-5-oxazolidine carboxylic acid methyl ester (Preparation No. 2, 5Ab, 355 mg, 0.79 mM) is dissolved in 9 mL methanol. To the solution is added water (350 μl) and potassium carbonate (155 mg, 1.12 mM). After stirring 5 hours no solids remain and TLC indicates very little methyl ester remaining. The solvent is concentrated in vacuo and water (10 ml) added to the oil. The solution is freeze dried leaving 500 mg fluffy white powder which contains 374 mg of the potassium salt.

TLC: silica gel 60; 1:2 EtOAc:Hexane; $R_f$: origin.

Preparation No. 4: Preparation of 7-TES-baccatin III-13-(4S,5R)-N-Benzoyl-2-(2,4-dimethoxyphenyl)-4-phenyl-5-oxazolidinecarboxylic acid ester (9AbA)

A solution of (4S,5R)-N-benzoyl-2-(2,4 dimethoxyphenyl)-4-phenyl-5-oxazolidine carboxylic acid potassium salt (6Ab, Preparation No. 3, 91.4 mg, approximately 0.15 mM) in ethyl acetate is washed with 5% aqueous NaHSO$_4$. The ethyl acetate solution is dried and evaporated leaving the corresponding acid 7Ab. The residue is dissolved in methylene chloride (0.8 ml) and toluene (1.75 ml), and combined with 7-triethylsilyl-baccatin III (68 mg). The mixture is treated with 4-dimethylaminopyridine (6.3 mg) and 1,3-dicyclohexylcarbodiimide (34 mg). The reaction is heated to 80° C. for 90 minutes, cooled, filtered, and chromatographed on silica gel in ethyl acetate-hexane mixtures. An 86% yield of the coupled product 9AbA was obtained.

NMR (CDCl$_3$, TMS): δ 0.58 (m, 6H); 0.90 (m); 1.73 (s, 3H); 1.87 (m,1H); 2.03 (m,3H); 2.17 (bs,3H); 2.20 (s,3H); 2.23 (m,2H); 2.50 (m, 1H); 3.78 (bs, 3H); 3.80 (s, 3H); 3.85 (d, 1H); 4.13 (d, 1H); 4.27 (d, 1H); 4.50 (m, 1H); 4.90 (m, 2H); 5.63 (bs, 1H); 5.68 (d, 1H); 6.25–6.48 (m, 3H); 6.50 (s, 1H); 6.86 (s, 1H); 7.09 (m, 1H); 7.15–7.65 (m, 13H); 8.05 (d, 2H).

Preparation No. 5: Preparation of Taxol (Compound 10AA)

7-TES-baccatin III-13-(4S,5R)-N-Benzoyl-2-(2,4-dimethoxyphenyl)-4-phenyl-5-oxazolidinecarboxylic acid ester (9AbA) is deprotected by stirring in 0.1 M HCl in methanol for 10 minutes. After diluting with ethyl acetate, the solution is washed with 5% NaHCO$_3$, dried and evaporated. The product is purified by column chromatography on silica gel in acetone-hexane mixtures. The proton and carbon NMR data are identical with natural taxol.

Preparation No. 6: Preparation of (4S,5R)-N-Boc-2-(2,4-dimethoxyphenyl)-4-phenyl-5-oxazolidinecarboxylic acid methyl ester (5Ba, & 5Bb)

N-Boc-β-phenyl isoserine methyl ester (3B) (0.5 g, 1.69 mM) is dissolved in dry THF (10 mL) and toluene (10 mL) and concentrated to dryness to remove any water of crystallization. The residue is then dissolved in dry THF (10 mL) and the solution treated with 2,4-dimethoxy benzaldehyde dimethyl acetal (4) (0.425 g, 2.0 mM) and pyridinium p-toluenesulfonate (12 mg) and the solution warmed to reflux. After 30 minutes the reaction is cooled to RT and allowed to stand overnight. It is then again warmed to reflux for 3 hours. The reaction is checked by TLC and is found to be incomplete. The reaction is then heated to 85° C. to distill off about ⅔ of the THF. Then fresh THF (10 mL) and acetal (200 mg) is added and the reaction refluxed another 2 hours. TLC shows the reaction to be finished at this point. The reaction is concentrated in vacuo and the residue chromatographed over 100 g silica gel packed in (15-85) acetone-hexane. The column is eluted with acetone-hexane (500 mL of 15-85 and 500 mL of 20-80). Fractions of 20 mL are collected. The desired product isomers elute as a mixture. The fractions containing the mixture of 5Ba & 5Bb and are combined and concentrated in vacuo leaving a white foam. The foam is rechromatographed over 100 g silica gel packed and eluted with (10-90) EtOAc-toluene. Fractions of 20 mL are collected and analyzed by TLC. There is thus isolated 34 mg of the less polar isomer 5Ba, 187 mg of a mixture of less polar and more polar isomers 5Ba and 5Bb, and 500 mg of the more polar isomer 5Bb.

Isomer 5Bb is crystallized from EtOAc-hexane to give white crystals (378 mg).

The mixture of isomers is also crystallized from EtOAc-hexane to give crystalline 5Bb (113 mg) of similar purity by TLC as the mother liquors from the isomer 5Bb crystallization. These crystals and the mother liquors are therefore combined and recrystallized from EtOAc-hexane to give more pure 5Bb (160 mg).

Data for 5Ba:

TLC: silica gel 60; 10% EtOAc-90% toluene; R$_f$: 0.44. $^1$H NMR (CDCl$_3$; TMS): δ 1.26 (s, 9H); 3.80 (s, 3H); 3.84 (s, 3H); 3.85 (s, 3H); 4.86 (d, 1H); 5.24 (s, 1H); 6.40 (dd, 1H); 6.47 (d, 1H); 6.72 (s, 1H); 7.12 (d, 1H); 7.30–7.43 (m, 3H); 7.53 (d, 2H).

Data for 5Bb:

TLC: silica gel 60; 10% EtOAc-90% toluene; R$_f$: 0.38. $^1$H NMR (CDCl$_3$; TMS): δ 1.10 (s, 9H); 3.52 (bd, 3H); 3.81 (s, 3H); 3.87 (s, 3H); a4.54 (d, 1H); 5.43 (bs, 1H); 6.48 (s, 2H); 6.81 (bs, 1H); 7.13 (bs, 1H); 7.30–7.48 (m, 5H). UV: EtOH; 233 (10,600), 260sh (1010), 277 (2840), 281sh (2680).

Elemental analysis: Calculated: C, 65.00; H, 6.59; N, 3.16. Found: C, 64.86; H, 6.42; N, 3.24.

Preparation No. 7: Preparation of (4S,5R)-N-Boc-2-(2,4-dimethoxyphenyl)-4-phenyl-5-oxazolidinecarboxylic acid potassium salt (6Ba) and its free acid 7Ba A 100 mg (0.23 mM) quantity (4S,5R)-N-Boc-2-(2,4-dimethoxyphenyl)-4-phenyl-5-oxazolidinecarboxylic acid methyl ester (Preparation No. 6, 5Ba) is stirred at room temperature under nitrogen in 3 mL MeOH. Added 0.1 mL water and 43 mg (0.31 mM) potassium carbonate. After 1 hour, TLC shows no starting material left. Store in freezer overnight. The next morning the solvent is evaporated to give (4S,5R)-N-Boc-2-(2,4-dimethoxyphenyl)-4-phenyl-5-oxazolidinecarboxylic acid potassium salt (6Ba). The residue is partitioned between methylene chloride and water containing 0.9 mL 1N HCl. The layers are separated and the aqueous layer reextracted with methylene chloride. The organic layers are combined, dried over sodium sulfate and evaporated. This leaves (4S,5R)-N-Boc-2-(2,4-dimethoxyphenyl)-4-phenyl-5-oxazolidinecarboxylic acid (7Ba) as a white solid.

TLC (silica gel 60): 20% EtOAc-80% hexane-2% HOAc: Rf: 0.07

$^1$H NMR (CDCl$_3$; TMS): δ 1.26 (s, 9H); 3.76 (s, 6H): 4.77 (s, 1H); 5.34 (s, 1H); 6.33–6.45 (d, 2H); 6.60 (s, 1H); 7.07–7.16 (d, 1H); 7.24–7.40 (m, 3H); 7.42–7.54 (d, 2H).

Preparation No. 8: Preparation of 7-TES-baccatin III-13-(4S,5R)-N-Boc-2-(2,4-dimethoxyphenyl)-4-phenyl-5-oxazolidinecarboxylic acid ester (9BaA)

A 0.23 mM quantity (4S,5R)-N-Boc-2-(2,4-dimethoxyphenyl)-4-phenyl-5-oxazolidinecarboxylic acid (Preparation No. 7, 7Ba) is dissolved in 1.5 mL methylene chloride-3 mL toluene. To this is added 106 mg (0.15 mM) 7-TES-baccatin III (8A), 11 mg (0.09 mM) DMAP and 49 mg (0.24 mM) DCC. The reaction is stirred under nitrogen and heated to 75° C. for 90 minutes then cooled to RT. The resultant urea side product is removed by filtration and the filtrate is evaporated under vacuum. The residue is chromatographed over 20 g silica gel, eluting with 30-70 EtOAc-hexane. Fractions of 5 mL are collected, analyzing them by TLC. Fractions 17–34 contain the desired product and are combined and evaporated. 7-TES-baccatin III-13-(4S,5R)-N-Boc-2-(2,4-dimethoxyphenyl)-4-phenyl-5-oxazolidinecarboxylic acid ester (9BaA) is obtained as a white solid.

TLC: silica gel 60; 30% EtOAc-70% hexane; Rf: 0.56

Mass Spec (FAB, m/z) 1112, 1012, 874, 328, 284, 115, 105, 87. $^1$H NMR (CDCl$_3$; TMS): δ 0.52–0.66 (m, 6H); 0.85–1.00 (m, 9H); 1.80–1.93 (m, 1H); 2.15 (s, 3H); 2.20 (s, 3H); 2.21–2.30 (m, 1H); 2.40–2.54 (m, 1H); 3.82 (s, 3H); 3.87 (s, 3H); 3.81 (d, 1H); 4.10 (d, 1H); 4.26 (d, 1H); 4.49 (m, 1H); 4.83–4.93 (m, 2H); 5.31 (d, 1H); 5.67 (d, 1H); 6.29 (t, 1H); 6.38–6.53 (m, 3H); 6.69 (s, 1H); 7.13 (d, 1H); 7.29–7.65 (m, 8H): 8.05 (d, 2H).

Preparation No. 9: Preparation of 13-(N-Boc-β-phenyl isoserinyl)-baccatin III (10BA)

A 0.1 M HCl solution is prepared from 0.071 mL acetyl chloride and 9.929 mL of MeOH, leaving it sit for 30 minutes before using.

To 57 mg (0.051 mM) 7-TES-baccatin III-13-(4S,5R)-N-Boc-2-(2,4-dimethoxyphenyl)-4-phenyl-5-oxazolidinecarboxylic acid ester (Preparation No. 8, 9BaA) is added 0.5 mL of the above methanolic HCl solution with stirring under nitrogen. The reaction is complete after 75 minutes as shown by TLC. The reaction mixture is partitioned between ethyl acetate-5% sodium bicarbonate. The layers are separated and the aqueous layer reextracted with ethyl acetate. The organic layers are combined, dried over sodium sulfate and evaporated under vacuum.

The crude product is chromatographed over 10 g silica gel, eluting with 50-50 ethyl acetate-toluene. Fractions of 2 mL are collected, analyzing them by TLC. Pure product is found in fractions 19–42,which are combined and evaporated. 13-(N-Boc-β-phenyl isoserinyl)-baccatin III (10BA) is obtained as a white solid.

TLC: silica gel 60; 50-50 EtOAc-toluene; Rf: 0.38.

Mass Spec (FAB): (M+H) measured at 850.3680; theory for $C_{45}H_{56}N_1O_{15}$ is 850.3650; m/z 794, 569, 509, 105, 57.
$^1$H NMR (CDCl$_3$, TMS): δ 1.14 (s, 3H); 1.27 (s, 3H); 1.33 (s, 9H); 1.67 (s, 3H); 1.84 (s, 3H); 2.24 (s, 3H); 2.38 (s, 3H); 3.44 (d, 1H): 3.81 (d, 1H); 4.17 (d, 1H); 4.30 (d, 1H); 4.41 (m, 1H); 4.63 (bs, 1H); 4.95 (d, 1H); 5.26 (bd, 1H); 5.43 (bd, 1H); 5.67 (d, 1H); 6.23 (t, 1H); 6.28 (s, 1H); 7.27–7.45 (m, 5H); 7.50 (t, 2H); 7.62 (t, 1H); 8.11 (d, 2H).

Preparation No. 10: Preparation of (4S,5R)-N-Boc-2-(2,4-dimethoxyphenyl)-4-phenyl-5-oxazolidinecarboxylic acid Potassium Salt (6Bb)

A solution of (4S,5R)-N-Boc-2-(2,4-dimethoxyphenyl)-4-phenyl-5-oxazolidinecarboxylic acid methyl ester (Preparation No. 6; 5Bb, 374 mg, 0.84 mM) in MeOH (11 mL) is stirred at RT under nitrogen and treated with water (0.37 mL) and potassium carbonate (161 mg, 1.17 mM). After 2 hours, TLC indicates the reaction to be about 70% done. After stirring overnight, the reaction is found to be complete. The solvent is evaporated and the residue dissolved in 10 mL water and freeze dried. This leaves 507 mg fluffy white solid, which contains (4S,5R)-N-Boc-2-(2,4-dimethoxyphenyl)-4-phenyl-5-oxazolidinecarboxylic acid potassium salt (6Bb, 393 mg).

TLC: silica gel; 20% EtOAc-80% hexane; $R_f$: origin.

Preparation No. 11: Preparation of 7-TES-baccatin III-13-(4S,5R)-N-Boc-2-(2,4-dimethoxyphenyl)-4-phenyl-5-oxazolidinecarboxylic acid ester (9BbA)

A 0.12 mM quantity of crude (4S,5R)-N-Boc-2-(2,4-dimethoxyphenyl)-4-phenyl-5-oxazolidinecarboxylic acid potassium salt (Preparation No. 10, 6Bb) is partitioned between ethyl acetate-5% sodium bisulfate. The layers are separated and the aqueous layer reextracted with ethyl acetate. The organic layers are combined, dried over sodium sulfate and evaporated under vacuum.

The resulting acid 7Bb is dissolved in 0.8 mL methylene chloride-1.5 mL toluene along with 53 mg (0.076 mM) of 7-TES-baccatin III (8A; See Denis, J.-N.; Greene, A. E.; Guénard, D.; Guéritte-Vogelein, F.; Mangatal, L.; Poder. P. J. Am. Chem. Soc. 1988, 110, 5917.). 6 mg (0.049 mM) 4-dimethylaminopyridine (DMAP) and 25 mg (0.12 mM) dicyclohexylcarbodiimide (DCC). The reaction is stirred under nitrogen and heated to 75° C. for 90 minutes. The reaction is cooled to room temperature and the urea side product filtered off. The filtrate is evaporated under vacuum.

The residue is chromatographed over 15 g silica gel, eluting with 30-70 EtOAc-hexane. Fractions of 7 mL are collected, analyzing them by TLC. Fractions 16–38 contain the product and are combined and evaporated. 7-TES-baccatin III-13-(4S,5R)-N-Boc-2-(2,4-dimethoxyphenyl)-4-phenyl-5-oxazolidinecarboxylic acid ester (9BbA) is obtained as a white solid.

TLC: silica gel 60; 30% EtOAc-70% hexane; Rf: 0.33

Mass Spec (FAB, m/z) 1112, 1012, 384, 328, 284, 115, 105, 87, 57. $^1$H NMR (CDCl$_3$; TMS): δ 0.50–0.61 (m, 6H); 0.84–0.97 (m, 9H); 1.08 (s, 9H); 2.21 (s, 3H); 3.67 (d, 1H); 3.80 (s, 3H); 3.90 (s, 3H); 4.07 (d, 1H); 4.23(d, 1H); 4.40 (m, 1H); 4.53 (bd, 1H); 4.87 (d, 1H); 5.44 (bd, 1H); 5.60 (d, 1H); 6.34 (s, 1H); 6.44 (bs, 1H); 6.48 (s, 1H); 7.20 (bs, 1H); 7.30–7.50 (m, 7H); 7.60 (t, 1H); 8.01 (d, 2H).

Preparation No. 12: Preparation of 13-(N-Boc-β-phenyl isoserinyl)-baccatin III (10BA)

A 0.1 M HCl solution is prepared from 0.071 mL acetyl chloride and 9.929 mL of MeOH, leaving it sit for 30 minutes before using.

To 45 mg (0.040 mM) 7-TES-baccatin III-13-(4S,5R)-N-Boc-2-(2,4-dimethoxyphenyl)-4-phenyl-5-oxazolidinecarboxylic acid ester (Preparation No. 11, 9BbA) is added 0.395 mL of the above methanolic HCl solution with stirring under nitrogen. The reaction is complete after 20 minutes as shown by TLC.

After 30 minutes the reaction mixture is partitioned between ethyl acetate-5% sodium bicarbonate. The layers are separated and aqueous layer reextracted with ethyl acetate. The organic layers are combined, dried over sodium sulfate and evaporated under vacuum.

The crude product is chromatographed over 5 g silica gel, eluting with 50-50 ethyl acetate-toluene. Fractions of 5 mL are collected and analyzed by TLC. Pure product is found in fractions 5–12 which are combined and evaporated. 13-(N-Boc-β-phenyl isoserinyl)-baccatin III (10BA) is obtained as a white solid.

TLC: silica gel 60; 50-50 EtOAc-toluene; Rf: 0.42

$^1$H NMR (CDCl$_3$, TMS): δ 1.15 (s, 3H); 1.27 (s, 3H); 1.33 (s, 9H); 1.68 (s, 3H); 1.85 (s, 3H); 2.25 (s, 3H); 2.38 (s, 3H); 3.44 (d, 1H); 3.80 (d, 1H); 4.17 (d, 1H); 4.30 (d, 1H); 4.41 (m, 1H); 4.62 (bs, 1H); 4.95 (d, 1H); 5.26 (bd, 1H); 5.43 (bd, 1H); 5.67 (d, 1H); 6.23 (t, 1H); 6.29 (s, 1H); 7.13–7.45 (m, 5H); 7.49 (t, 2H); 7.62 (t, 1H); 8.11 (d, 2H).

Preparation No. 13: Preparation of 7-(2,2,2-trichloroethoxycarbonyl)-baccatin III-13-(4S,5R)-N-Boc-2-(2,4-dimethoxyphenyl)-4-phenyl-5-oxazolidinecarboxylic acid ester (9BaB, 9BbB)

A 0.39 mM quantity of (4S,5R)-N-Boc-2-(2,4-dimethoxyphenyl)-4-phenyl-5-oxazolidinecarboxylic acid potassium salt (6Ba, 6Bb) is partitioned between ethyl acetate-5% sodium bisulfate. The layers are separated and the aqueous layer reextracted with ethyl acetate. The organic layers are combined, dried over sodium sulfate and evaporated under vacuum.

The residual acid 7Ba,7Bb is dissolved with stirring under nitrogen in 2 mL methylene chloride-6 mL toluene. To this is added 187 mg (0.245 mM) 7-(2,2,2-trichloroethoxycarbonyl)-baccatin III (8B, See for example Mangatal, L.; Adeline, M.-T.; Guenard, D.; Gueritte-Vogelein, F.; Potier, P. Tetrahedron 1989, 45, 4177.), followed by 22 mg (0.18 mM) DMAP and 80 mg (0.39 mM) DCC. Soon after everything goes into solution, the urea side product starts to precipitate. The reaction is heated to 80° C. for 70 minutes, following the reaction by TLC. After cooling to room temperature, the solid is filtered off and the filtrate evaporated under vacuum. The crude product is chromatographed over 50 g silica gel, eluting with 400 mL 30-70, 200 mL 40-60, 100 mL 70-30 ethyl acetate-hexane. Fractions of 15 mL are collected, analyzing them by TLC. The following fractions are combined and evaporated under vacuum to give white solids.

Fr 14–20, less polar isomer 9BaB

Fr 21–26, mixed isomers 9BaB, 9BbB

Fr 27–32, more polar isomer 9BbB

Fr 37–44, recovery of starting alcohol 8B

Data for isomer 9BaB:

TLC: silica gel 60; 40-60 ethyl acetate-hexane; Rf: 0.67.

¹H NMR (CDCl₃, TMS) δ 1.26 (s); 1.82 (s, 3H); 2.12 (s, 3H); 2.19 (s, 3H); 2.58 (m, 1H); 3.81 (s, 3H); 3.91 (s, 3H); 3.97 (d, 1H); 4.13 (d, 1H); 4.28 (d, 1H); 4.66 (d, 1H); 4.92 (m, 2H); 5.03 (d, 1H); 5.36 (d, 1H); 5.63 (m, 1H); 5.67 (d, 1H); 6.32 (m, 1H); 6.40 (s, 1H); 6.51 (d, 1H); 6.69 (s, 1H); 7.16 (d, 1H); 7.37–7.62 (m, 8H); 8.02 (d, 2H).

Data for isomer 9BbB:

TLC: silica gel 60; 40-60 ethyl acetate-hexane; Rf: 0.55.

¹H NMR (CDCl₃, TMS) δ 2.17 (bs); 3.47 (m); 3.79–3.94 (m); 4.08 (d); 4.27 (d); 4.54 (m); 4.65 (m); 4.89 (d); 5.01 (m); 5.40 (m); 5.50 (m); 5.62 (d); 6.24 (bs); 6.49 (bs); 7.37–7.65 (m); 8.03 (d).

Preparation No. 14: Preparation of 7-(2,2,2-trichloroethoxycarbonyl)-13-(N-Boc-β-phenyl isoserinyl)-baccatin III 10BB A 0.1M HCl solution in MeOH is prepared from 0.071 mL acetyl chloride and 9.929 mL MeOH and left standing for 30 minutes before using.

A 252 mg (0.216 mM) quantity of 7-(2,2,2-trichloroethoxycarbonyl)-baccatin III-13-(4S,5R)-N-Boc-2-(2,4-dimethoxyphenyl)-4-phenyl-5-oxazolidinecarboxylic acid ester (Preparation No. 13; 9BaB,9BbB) is stirred at RT under nitrogen with 2.2 mL of the above 0.1 M HCl solution in MeOH. The reaction is followed by TLC and since it is incomplete after 20 minutes, another 0.5 mL HCl solution is added and the reaction continued for 15 minutes.

The reaction mixture is then diluted with ethyl acetate and washed with 5% sodium bicarbonate. The layers are separated and the aqueous layer reextracted with ethyl acetate. The organic layers are combined, dried over sodium sulfate and evaporated under vacuum. The crude product is chromatographed over 30 g silica gel, eluting with 200 mL 35-65 and 300 mL 40-60 ethyl acetate-hexane. Fractions of 5 mL are collected, analyzing them by TLC. Fractions 25–54 contain the pure product and are combined and evaporated under vacuum to give 7-(2,2,2-trichloroethoxycarbonyl)-13-(N-Boc-β-phenyl isoserinyl)-baccatin III 10BB, as a white solid.

TLC: silica gel 60; 40-60 ethyl acetate-hexane; Rf: 0.36

Mass Spec (FAB, m/z) (M+H) at 1024, 1026, 1028; (M+H) measured at 1024.2656; theory for $C_{48}H_{57}Cl_3N_1O_{17}$ is 1024.2692; 1024, 968, 924, 743, 683, 105, 57. ¹H NMR (CDCl₃, TMS) δ 1.17 (s, 3H); 1.24 (s, 3H); 1.34 (s, 9H); 1.83 (s, 3H); 1.91 (s, 3H); 2.17 (s, 3H); 2.39 (s, 3H); 2.62 (m, 1H); 3.60 (d, 1H); 3.94 (d, 1H); 4.16 (d, 1H); 4.30 (d, 1H); 4.63 and 5.04 (2d, 2H); 4.62 (bs, 1H); 4.95 (d, 1H); 5.26 (bd, 1H); 5.45–5.60 (m, 2H); 5.66 (d, 1H); 6.20 (t, 1H); 6.36 (s, 1H); 7.24–7.44 (m, 5H); 7.49 (t, 2H); 7.61 (t, 1H); 8.08 (d, 2H).

Preparation No. 15: Preparation of 13-(N-Boc-β-phenyl isoserinyl)-baccatin III (10BA) and 7-(2,2-dichloroethoxycarbonyl)-13-(N-Boc-β-phenyl isoserinyl)-baccatin III 10BG.

A 150 mg (0.146 mM) quantity of 7-(2,2,2-trichloroethoxycarbonyl)-13-(N-Boc-β-phenyl isoserinyl)-baccatin III (Preparation No. 14, 10BB) is stirred at RT under nitrogen in 13.5 mL MeOH and 1.5 mL HOAc. To this is added 150 mg activated zinc and the reaction heated to 50° C. for 60 minutes. The reaction is followed by TLC and adding 4 more 150 mg portions of zinc, heating for 45 minutes after each addition. The reaction mixture is filtered and the filtrate evaporated under vacuum. The residue is partitioned between methylene chloride-water. The layers are separated and the aqueous layer backextracted with methylene chloride. The organic layers are combined, dried over sodium sulfate and evaporated.

The crude product is chromatographed over 20 g silica gel. eluting with 200 mL 60-40 and 200 mL 70-30 ethyl acetate-hexane. Fractions of 5 mL are collected, analyzing them by TLC. The following fractions are combined and evaporated to give white solids.

Fr 9–13, 7-(2,2-dichloroethoxycarbonyl)-13-(N-Boc-β-phenyl isoserinyl)-baccatin III 10BG.

Fr 14–44, 13-(N-Boc-β-phenyl isoserinyl)-baccatin III (10BA) Data for 7-(2,2-dichloroethoxycarbonyl)-13-(N-Boc-β-phenyl isoserinyl)-baccatin III 10BG TLC: silica gel 60; 50-50 ethyl acetate-hexane; Rf: 0.81 (this product and starting material run together in this TLC system).

¹H NMR: (CDCl₃, TMS) δ 1.17 (s, 3H); 1.24 (s, 3H); 1.35 (s, 9H); 1.61 (s, 3H); 1.81 (s, 3H); 2.19 (s, 3H); 2.39 (s, 3H); 2.52–2.68 (m, 1H); 3.37 (d, 1H); 3.92 (d, 1H); 4.16 (d, 1H); 4.32 (d, 1H); 4.53 (m, 2H); 4.63 (bs, 1H); 4.95 (d, 1H); 5.26 (bd, 1H); 5.40 (bd, 1H); 4.48 (m, 1H); 5.67 (d, 1H); 5.96 (m, 1H); 6.20 (t, 1H); 6.45 (s, 1H); 7.28–7.44 (m, 5H); 7.50 (t, 2H); 7.62 (t, 1H); 8.10 (d, 2H).

Data for 10BA:

TLC: silica gel 60; 50-50 ethyl acetate-hexane; Rf: 0.32

¹H NMR: (CDCl₃, TMS) δ 1.14 (s, 3H); 1.24 (s, 3H); 1.32 (s, 9H); 1.67 (s, 3H); 1.84 (s, 3H); 2.23 (s, 3H); 2.37 (s, 3H); 2.44–2.59 (m, 1H); 2.64 (bd, 1H); 3.70 (bs, 1H); 3.78 (d, 1H); 4.15 (d, 1H); 4.28 (d, 1H); 4.40 (m, 1H); 4.61 (bs, 1H); 4.94 (d, 1H); 5.25 (bd, 1H); 5.57 (bd, 1H); 5.65 (d, 1H); 6.22 (t, 1H); 6.29 (s, 1H): 7.24–7.44 (m, 5H); 7.48 (t, 2H); 7.60 (t, 1H); 8.08 (d, 2H).

Preparation No. 16: Preparation of 7,10-bis-Troc-baccatin III-13-(4S,5R)-N-Boc-2-(2,4-dimethoxyphenyl)-4-phenyl-5-oxazolidinecarboxylic acid ester (9BbC)

Crude (4S,5R)-N-Boc-2-(2,4-dimethoxyphenyl)-4-phenyl-5-oxazolidinecarboxylic acid potassium salt (Preparation No. 10; 6Bb) (0.089 mM) is partitioned between EtOAc-5% NaHSO₄. The layers are separated and the aqueous layer reextracted with EtOAc. The organic layers are combined, dried over sodium sulfate and evaporated under vacuum leaving (4S,5R)-N-Boc-2-(2,4-dimethoxyphenyl)-4-phenyl-5-oxazolidinecarboxylic acid (7Bb). This residue is stirred at room temperature under nitrogen in methylene chloride (0.8 mL) and toluene (1.5 mL). To this is added 7,10-bis-Troc-10-deacetyl baccatin III (8C, see for example Senith, V.; Gueritte-Vogelein, F.; Guenard, D.; Colin, M.; Potier, P. C. R. Acad. Sci. Paris 1984, 299. 4177.), 50 mg, 0.056 mM. The resultant solution is treated with 4-dimethylaminopyridine (5 mg, 0.04 mM) and 1,3-dicyclohexyl carbodiimide (18 mg, 0.087 mM) and then heated to 75° C. (25 min). TLC analysis after 15 minutes heating shows the reaction to be complete.

The precipitated dicyclohexyl urea is filtered off. The filtrate is coated on silica gel (1 g) and chromatographed over silica gel (10 g), which is eluted with EtOAc-hexane (30-70). Fractions of 4 mL are collected, analyzing them by TLC. Fractions 16–42 contain the product and are combined and evaporated under vacuum. This produces 7,10-bis-Troc-baccatin III-13-(4S,5R)-N-Boc-2-(2,4-dimethoxyphenyl)-4-phenyl-5-oxazolidinecarboxylic acid ester (9BbC) as a white solid.

TLC (silica gel 60): 40% EtOAc-60% hexane; $R_f$: 0.56

Mass Spec (FAB, m/z) 1304, 1306, 1308 (M+H), 1204, 875, 683, 384, 328 284, 105 (base), 57. ¹H NMR (CDCl₃; TMS): δ 1.07 (s, 3H); 1.14 (s, 3H); 1.22 (s, 3H); 1.79 (s, 3H); 2.56 (m, 1H); 3.79 (d, 1H); 3.81 (s, 3H); 3.89 (s, 3H); 4.08 (d, 1H); 4.25 (d, 1H); 4.54 (d, 1H); 4.59 and 4.88 (2d, 2H); 4.78 (s, 2H); 4.89 (bt, 1H); 5.43(m, 1H); 5.50 (m, 1H); 5.62 (d, 1H); 6.05 (bs, 1H); 6.12 (s, 1H); 6.47 (d, 1H); 6.49 (s, 1H); 6.75 (bs, 1H); 7.21. (m, 1H); 7.35–7.53 (m, 7H); 7.62 (t, 1H); 8.01 (d, 2H).

Preparation No. 17: Preparation of 7,10-bis-Troc-13-(N-Boc-β-phenyl isoserinyl)-baccatin III (10BC).

Acetyl chloride (0.071 mL, 80 mg, 1.0 mM) is added to methanol (10 mL) and the solution allowed to stand for 30 minutes, giving a 0.1 N HCl solution. 7,10-Bis-Troc-baccatin III-13-(4S,5R)-N-Boc-2-(2,4-dimethoxyphenyl)-4-phenyl-5-oxazolidinecarboxylic acid ester (Preparation No. 16; 9BbC) (73 mg, 0.056 mM) is dissolved in the above methanolic HCl solution (0.553 mL) and allowed to stand (25 min). The reaction is then diluted with EtOAc and washed with 5% sodium bicarbonate. The layers are separated and the aqueous layer reextracted with EtOAc. The organic phases are combined, dried over sodium sulfate and evaporated under vacuum. The crude product is coated on silica gel (1 g) and chromatographed over silica gel (10 g). The column is eluted with 20% EtOAc-80% toluene. Fractions of 4 ml are collected, analyzing them by TLC. Pure product is found in fractions 10–20 which are combined and evaporated. Impure product in fractions 7–9, is rechromatographed as above. Fractions 11–26 contained the pure product and are combined with pure product from the first column. This gives 7,10-bis-Troc-13-(N-Boc-β-phenyl isoserinyl)-baccatin III (10BC) as a white solid.

TLC (silica gel 60): 30% EtOAc-70% toluene; $R_f$: 0.59; the side product 2,4-dimethoxy benzaldehyde runs just ahead of product and right where starting material comes.

Mass Spec (FAB, m/z) 1156, 1158, 1160 (M+H), 1100, 1056, 701, 685, 105 (base), 57. $^1$H NMR (CDCl$_3$; TMS): δ 1.20 (s, 3H); 1.27 (s, 3H); 1.35 (s, 9H); 1.85(s, 3H); 1.95 (s, 3H); 2.35 (s, 3H); 3.41 (d, 1H); 3.90 (d, 1H); 4.17 (d, 1H); 4.33 (d, 1H); 4.60 and 4.92 (2d, 2H); 4.62 (bs, 1H); 4.78 (s, 2H); 4.95 (d, 1H); 5.26 (bd, 1H); 5.42 (bd, 1H); 5.54 (dd, 1H); 5.69 (d, 1H); 6.21 (t, 1H); 6.24 (s, 1H); 7.12–7.42 (m, 6H); 7.49 (t, 2H); 7.62 (t, 1H); 8.09 (d, 2H).

Preparation No. 18: Preparation of 7-(2,2-dichloroethoxycarbonyl)-13-(N-Boc-β-phenyl isoserinyl)-baccatin III (10BD), 10-(2,2-dichloroethoxycarbonyl)-13-(N-Boc-β-phenyl isoserinyl)-baccatin III (10BE), and 13-(N-Boc-β-phenyl isoserinyl)-baccatin III (10BF, Taxotere)

7,10-Bis-Troc-13-(N-Boc-β-phenyl isoserinyl)-baccatin III (Preparation No. 17; 10BC) (48 mg. 0.041 mM) is stirred at room temperature under nitrogen in 90% MeOH-10% HOAc (3 mL) and the solution treated with activated zinc (85 mg). After 30 minutes reaction a cloudiness occurs. One mL more of the MeOH-HOAc solution is added and the reaction becomes clear. TLC after 30 and 60 minutes look very similar, namely no starting material and two minor and one major more polar products. After 70 minutes reaction, the solid zinc is filtered off. The filtrate is evaporated under vacuum. The residue is partitioned between methylene chloride and water. The layers are separated and the aqueous layer re-extracted with methylene chloride. The organic layers are again washed with water, dried over sodium sulfate, combined and evaporated under vacuum. The crude product mixture is coated on silica gel (1 g) and chromatographed over silica gel (5 g). The column is eluted with EtOAc-hexane (100 mL each of 40-60, 50-50, 60-40,and 70-30). Fractions of 4 mL are collected, analyzing them by TLC. The following fractions are combined and evaporated.

Fr. 12–24, 10BD
Fr. 29–42, 10BE
Fr. 48–84, 10BF

Data for 10BD:
TLC (silica gel 60): 60% EtOAc-40% hexane; $R_f$: 0.92
Mass Spec (FAB, m/z) 948, 950, 952 (M+H), 892, 848, 830, 667, 649, 105 (base), 57. $^1$H NMR (CDCl$_3$; TMS): δ 1.09 (s, 3H); 1.23 (s, 3H); 1.34 (s, 9H); 1.86(s, 3H); 1.89 (s, 3H); 2.04 (m, 1H); 2.29 (d, 2H); 2.39 (s, 3H); 3.4 (bs, 1H); 3.99 (d, 1H); 4.05 (s, 1H); 4.20 (d, 1H); 4.33 (d, 1H): 4.48 (m, 2H); 4.62 and 4.93 (2d, 2H); 5.30 (m, 1H); 5.37 (s, 1H); 5.46 (d, 1H); 5.68 (d, 1H); 5.83 (t, 1H): 6.21 (t, 1H); 7.3–7.45 (m, 6H); 7.50 (t, 2H); 7.62 (t, 1H); 8.10 (d, 2H).

Data for 10BE:
TLC (silica gel 60): 60% EtOAc40% hexane; $R_f$: 0.65.
Mass Spec (FAB, m/z) 948, 950, 952 (M+H), 892, 848, 667, 527, 509, 105 (base), 57. $^1$H NMR (CDCl$_3$; TMS): δ 1.16 (s, 3H); 1.27 (s, 3H); 1.33 (s, 9H); 1.70 (s, 3H); 1.89 (s, 3H); 2.39 (s, 3H); 2.57 (m, 1H); 3.40 (d, 1H); 3.75 (d, 1H); 4.17 (d, 1H); 4.33 (d, 1H); 4.35 (m, 1H); 4.56 (dd, 2H); 4.64 (m, 1H); 4.95 (d, 1H); 5.28 (m, 1H); 5.37 (d, 1H); 5.68 (d, 1H); 5.92 (d, 1H); 6.15 (s, 1H); 6.25 (t, 1H); 7.20–7.45 (m, 6H); 7.50 (t, 2H); 7.64 (t, 1H); 8.10 (d, 2H).

Data for 10BF:
TLC (silica gel 60): 60% EtOAc-40% hexane; $R_f$: 0.23.
Mass Spec (FAB, m/z) 808 (M+H), 790, 752, 708, 527, 509, 345, 327, 105 (base), 57. $^1$H NMR (CDCl$_3$; TMS): δ 1.12 (s, 3H); 1.23 (s, 3H); 1.33 (s, 9H); 1.74 (s, 3H); 1.84 (s, 3H); 2.37 (s, 3H); 2.56 (m, 1H); 3.60 (bs, 1H); 3.89 (d, 1H): 4.18 (d, 1H); 4.21 (m, 1H); 4.30 (d, 1H); 4.32 (s, 1H); 4.62 (bs, 1H); 4.94 (d, 1H); 5.23 (s, 1H); 5.28 (bs, 1H); 5.54 (d, 1H); 5.66 (d, 1H); 6.20 (t, 1H); 7.25–7.45 (m, 6H); 7.50 (t, 2H); 7.61 (t, 1H); 8.09 (d, 2H).

Preparation No. 19: Preparation of (2R,3S)-N-carbobenzyloxy-β-phenyl isoserine methyl ester (3C)

A solution of (2R,3S)-β-phenyl isoserine methyl ester (2) (Preparation No. 1, 2 mM) in pyridine containing a small amount of DMAP is cooled in an ice bath and treated with benzyl chloroformate (0.8 ml). After stirring at room temperature overnight, the reaction is diluted with ethyl acetate, washed with 5% aqueous sodium bisulfate, dried and evaporated. The product is obtained pure by silica gel chromatography in ethyl acetate-hexane mixtures. Mp 120–121° C. NMR(CDCl$_3$, TMS): δ 3.26 (m, 1H); 3.79 (s, 3H); 4.47 (m, 1H); 5.06 (m, 2H); 5.27 (d, 1H); 5.75 (m, 1H); 7.20–7.50 (m, 10 H).

Preparation No. 20: Preparation of (4S,5R)-N-Carbobenzyloxy-2-(2,4-dimethoxyphenyl)-4-phenyl-5-oxazolidinecarboxylic acid methyl ester 5Cb N-Carbobenzyloxy-β-phenyl isoserine methyl ester (Preparation No. 19, 3C, 0.375 g, 1.14 mM) is dissolved in dry THF (10 mL) and the solution treated with 2,4-dimethoxy benzaldehyde dimethyl acetal (4, 0.300 g, 1.42 mM) and pyridinium p-toluenesulfonate (10 mg) and the solution heated to distill off the THF and methanol. After ½ the THF is distilled off, THF (10 mL) is added and the reaction distilled to ½ volume again. The process is repeated three times. The reaction is then concentrated in vacuo and the residue chromatographed over 75 g silica gel packed and eluted in acetone-hexane (300 mL of 20-80 and 300 mL of 25-75). Fractions of 20 mL are collected and analyzed by TLC. The following fractions are combined and evaporated under vacuum.

Fr. 26–44, 543 mg, isomer 5Cb (other runs have shown this to he the more polar isomer).

Data for 5Cb:
TLC: silica gel; 20% acetone-80% hexane; $R_f$: 0.19.
$^1$H NMR (CDCl$_3$; TMS): δ 3.51 (bs, 3H); 3.81 (bs, 6H); 4.56 (d, 1H); 4.8 (bd, 1H); 4.94 (d, 1H); 5.54 (d, 1H); 6.4 (bs, 2H); 6.78 (d, 3H); 7.05–7.50 (m, 9H).

Preparation No. 21: Preparation of (4S,5R) N-CBZ-2-(2,4 dimethoxyphenyl)-4-phenyl-5-oxazolidine carboxylic acid potassium salt. 6Cb (4S ,5R)-N-CB Z-2-(2,4 dimethoxyphenyl)-4-phenyl-5-oxazolidine carboxylic acid methyl ester (Preparation No.

20, 5Cb, 444 mg, 0.93 mM) is dissolved in 10 mL methanol. To the solution is added water (400 μl) and potassium carbonate (200 mg, 1.45 mM). After stirring overnight no solids remain and TLC indicates very little methyl ester remaining. The solvent is concentrated in vacuo and water (20 ml) added to the oil. The solution is freeze dried leaving 638 mg fluffy white powder which contains 466 mg of the potassium salt 6Cb.

TLC: silica gel 60; 1:4 EtOAc:Toluene; $R_f$: origin.

Preparation No. 22: Preparation of 7-Triethylsilyl-Baccatin III-13-(4S,5R)-N-CBZ-2-(2,4 dimethoxyphenyl)-4-phenyl-5-oxazolidinecarboxylic acid ester. 9CbA Crude (4S,5R)-N-CBZ-2-(2,4 dimethoxyphenyl)-4-phenyl-5-oxazolidine carboxylic acid potassium salt (6Cb, Preparation No. 21; 75 mg, 0.11 mM) is partitioned between $CH_2Cl_2$ and 5% $NaHSO_4$ solution. The layers are separated and the aqueous layer extracted with EtOAc. The combined organic layers are filtered through anhydrous sodium sulfate and concentrated in vacuo leaving 51 mg of (4S,5R)-N-CBZ-2-(2,4 dimethoxyphenyl)-4-phenyl-5-oxazolidine-carboxylic acid (7Cb).

7-Triethylsilyl-baccatin III (8A, 50 mg, 0.07 mM) is dissolved in 700 μL toluene. All of the (4S,5R)-N-CBZ-2-(2,4 dimethoxyphenyl)-4-phenyl-5-oxazolidinecarboxylic acid is added in a solution of $CH_2Cl_2$. To the solution is added DCC (25 mg. 0.11 mM) and DMAP (4 mg. 0.04 mM) and the solution heated to 80° C. driving off the $CH_2Cl_2$. The reaction is checked by TLC and after 1.5 hours very little 7-triethylsilyl-baccatin III is seen. The reaction is allowed to cool and the slurry filtered. The filtrate is concentrated in vacuo and chromatographed over 7 gm of silica gel packed in 1:3 EtOAc:Hexane. The column is eluted with 40 mL 1:3 EtOAc:Hexane and 75 ml 1:2 EtOAc:Hexane collecting 3 ml fractions. The desired product is found in fractions 17–32.

Mass Spec (FAB-High Res.) Theory: 1146.4882 Found: 1146.4915 $^1$H NMR (CDCl$_3$; TMS): δ 0.51–0.59 (m,6H); 0.88–0.94 (m); 1.13 (s,3H); 1.18 (s, 3H); 1.79–1.89 (m,1H); 2.17 (s,3H); 2.40–2.50 (m1H); 3.67 (d,1H); 3.80 (br s,6H); 4.07 (d,1H); 4.22 (d,1H); 4.39 (m,1H); 4.54 (d,1H); 4.77 (d,1H); 4.86 (d,1H); 4.94 (d,1H); 5.54 (d,1H); 5.61 (d,1H); 5.90 (m,1H); 6.33 (s,1H); 6.43 (m,2H); 6.78 (m,3H); 7.12–7.21 (m,4H); 7.38–7.50 (m,7H); 7.59 (m,1H); 8.01 (d,2H)

Preparation No. 23: Preparation of 13-(N-CBZ-β-phenyl-isoserinyl)-baccatin III 10CA and 10-deacetyl-13-(N-CBZ-β-phenyl-isoserinyl)baccatin III 10CB 7-Triethylsilyl-Baccatin III-13-(4S,5R)-N-CBZ-2-(2,4 dimethoxyphenyl)-4-phenyl-5-oxazolidinecarboxylic acid ester (9CbA, Preparation No. 22; 630 mg, 0.55 mM) is dissolved in 10 mL 0.1N HCl in methanol. The 0.1N HCl solution is made by diluting 71 μL acetyl chloride to 10 mL with methanol and allowing to react for a minimum of 0.5 hours. The reaction is checked by TLC and after 0.5 hours no starting materials is seen. The reaction solution is partitioned between brine, 5% $NaHCO_3$ solution, and EtOAc. The layers are separated and the organic layer is extracted with 5% $NaHCO_3$ solution. The combined aqueous layers are extracted with EtOAc and the combined organic layers are filtered through anhydrous sodium sulfate. The solvent is concentrated in vacuo and the residue chromatographed over 60 gm silica gel packed in 1:1 EtOAc:Hexane. The column is eluted with 500 mL 1:1 EtOAc:Hexane, 250 mL 3:2 EtOAc:Hexane, 240 mL 2:1 EtOAc:Hexane collecting 25 mL fractions.

Fractions 16–36, 13-(N-CBZ-β-phenyl-isoserinyl) baccatin III, 10CA

Fractions 44–52, 10-deacetyl-13-(N-CBZ-β-phenyl-isoserinyl)-baccatin III 10CB

Data for 10CA:

Mass Spec (FAB-High Res.) Theory: 884.3493 Found: 884.3490 $^1$H NMR (CDCl$_3$; TMS): δ 1.13 (s,3H);1.80(s, 3H); 1.86 (m,1H); 2.24 (s,3H); 2.37 (s,3H); 2.54 (m,2H); 3.43 (m,1H); 3.76(d,1H); 4.19 (d,1H); 4.28 (d,1H); 4.39 (m,1H); 4.66 (br s,1H); 4.90–4.97 (m,1H); 4.94 (d,1H); 5.05 (d,1H); 5.34 (d,1H); 5.64 (d,1H); 5.75 (d,1H); 6.23 (m,1H); 6.25 (s,1H); 7.17 (br s,2H); 7.25 (br s,3H); 7.29–7.41 (m,5H); 7.50 (m,2H); 7.61 (m,1H); 8.12 (d,2H)

Data for 10CB:

Mass Spec (FAB-High Res.) Theory: 842.3388 Found: 842.3364 $^1$H NMR (CDCl$_3$; TMS): δ 2.37 (s,3H); 2.57 (m,1H); 3.40 (d,1H); 3.87 (d,1H); 4.18–4.32 (m); 4.65 (br s,1H); 4.92 (d,1H); 4.95 (d,1H); 5.06 (d,1H); 5.18 (s,1H); 5.35 (d,1 H); 5.65 (d,1H); 5.78 (d,1H); 6.20 (m,1H); 7.18 (m,1H); 7.22–7.46 (m); 7.50 (m,2H); 7.61 (m,1H); 8.11 (d,2H)

Preparation No. 24: Preparation of 13-(β-phenyl isoserinyl)-baccatin III (11A) from 13-(N-Cbz-β-phenyl isoserinyl)-baccatin III (10CA)

A 405 mg (0.46 mM) quantity 13-(N-Cbz-β-phenyl isoserinyl)-baccatin III (Preparation No. 23; 10CA) is stirred at room temperature and hydrogenated at atmospheric pressure with 40 mL absolute ethanol and 100 mg 10% Pd/C. The reaction is followed by TLC, being complete after 5 hours.

The reaction is filtered through Celite, washing with ethyl acetate. The combined filtrate and wash are evaporated under vacuum. The residue is treated with a small amount of ethyl acetate and a larger amount of hexane and reevaporated twice more. 13-(β-phenyl isoserinyl)-baccatin III (11A) is obtained as a white solid.

TLC: silica gel 60; 70-30 EtOAc-hexane; Rf: streak between origin and ⅓ up the plate.

$^1$H NMR (CDCl$_3$, TMS): δ 1.13 (s, 3H); 1.24 (s, 3H); 1.66 (s, 3H); 1.88 (s, 3H); 2.23 (s, 3H); 2.24 (s, 3H); 2.45–2.61 (m, 1H); 3.75 (d, 1H); 4.14 (d, 1H); 4.23–4.33 (m, 3 H); 4.40 (m, 1H); 4.93 (d, 1H); 5.63 (d, 1H); 6.13 (t, 1H); 6.27 (s, 1H); 7.26 (m, 1H); 7.39 (d, 4H); 7.52 (t, 2H); 7.65 (t, 1H); 8.06 (d, 2H).

Preparation No. 25: Preparation of (2R,3S)-N-(2,2,2-trichloroethoxycarbonyl)-β-phenyl isoserine methyl ester (3D)

Following the general procedure of Preparation No. 19 [(2R,3S)-N-Carbobenzyloxy-β-phenyl isoserine methyl ester (3C)], but starting with 2,2,2-trichloroethoxycarbonyl chloride to acylate the amine β-phenyl isoserine methyl ester (2) the product N-(2,2,trichloroethoxycarbonyl)-β-phenyl isoserine methyl ester (3D) is prepared.

Preparation No. 26: Preparation of (4S,5R)-N-(2,2,2-trichloroethoxycarbonyl)-2-(2,4-dimethoxyphenyl)-4-phenyl-5-oxazolidinecarboxylic acid methyl ester 5Da & 5Db Following the general procedure of Procedure 20 [Preparation of (4S,5R)-N-Carbobenzyloxy-2-(2,4-dimethoxyphenyl)-4-phenyl-5-oxazolidinecarboxylic acid methyl ester (5Cb)], but starting with (2,2,2-trichloroethoxycarbonyl)-β-phenyl isoserine methyl ester (3D) the product (4S,5R)-N-(2,2,2-trichloroethoxycarbonyl)-2-(2,4-dimethoxyphenyl)-4-phenyl-5-oxazolidinecarboxylic acid methyl ester (5Da, 5Db) is prepared.

Preparation No. 27: Preparation of (4S,5R)-N-(2,2,2-trichloroethoxycarbonyl)-2-(2,4-dimethoxyphenyl)-4-phenyl-5-oxazolidinecarboxylic acid potassium salt (6Da, 6Db)

Following the general procedure of Preparation 21 [(4S, 5R)-N-Carbobenzyloxy-2-(2,4-dimethoxyphenyl)-4-phenyl-5-oxazolidinecarboxylic acid potassium salt (6Cb)], but starting with (4S,5R)-N-(2,2,2-trichloroethoxycarbonyl)-2-(2,4-dimethoxyphenyl)-4-phenyl-5-oxazolidinecarboxylic acid methyl ester (5Da, 5Db) the product (4S,5R)-N-(2,2,2-trichloroethoxycarbonyl)-2-(2,4-dimethoxyphenyl)-4-phenyl-5-oxazolidinecarboxylic acid potassium salt (6Da, 6Db) is prepared.

Preparation No. 28: Preparation of 7-Triethylsilyl-Baccatin III-13-(4S,5R)-N-(2,2,2-trichloroethoxycarbonyl)-2-(2,4 dimethoxyphenyl)-4-phenyl-5-oxazolidinecarboxylic acid ester (9DaA, 9DbA)

Following the general procedure of Preparation No. 22 [preparation of 7-Triethylsilyl-Baccatin III-13-(4S,5R)-N-CBZ-2-(2,4 dimethoxyphenyl)-4-phenyl-5-oxazolidinecarboxylic acid ester, 9CbA], but starting with (4S,5R)-N-(2,2,2-chloroethoxycarbonyl)-2-(2,4 dimethoxyphenyl)-4-phenyl-5-oxazolidine carboxylic acid (6Da, 6Db) is prepared the desired 7-Triethylsilyl-Baccatin III-13-(4S,5R)-N-(2,2,2-trichloroethoxycarbonyl)-2-(2,4 dimethoxyphenyl)-4-phenyl-5-oxazolidinecarboxylic acid ester (9DaA, 9DbA).

Preparation No. 29: Preparation of 13-(N-(2,2,2-trichloro-ethoxycarbonyl)-β-phenyl-isoserinyl)-baccatin III (10DA)

Following the general procedure of Preparation No. 23 [preparation of 13-(N-CBZ-β-phenyl-isoserinyl)-baccatin III (10CA)], but starting instead with 7-triethylsilyl-baccatin III-13-(4S,5R)-N-(2,2,2-trichloroethoxycarbonyl)-2-(2,4 dimethoxyphenyl)-4-phenyl-5-oxazolidinecarboxylic acid ester (9Da, 9Db)] the product 3-(N-(2,2,2-trichloroethoxycarbonyl)-β-phenyl-isoserinyl)-baccatin III (10DA) is prepared.

Preparation No. 30: Preparation of 13-(β-phenyl-isoserinyl)-baccatin III (11A) from 13-(N-(2,2,2-trichloro-ethoxycarbonyl)-β-phenyl-isoserinyl)-baccatin III (10DA)

13-(N-(2,2,2-trichloro-ethoxycarbonyl)-β-phenyl-isoserinyl)-baccatin III (Preparation No. 29; 10DA, 1 g) is dissolved in methanol (50 mL) and the solution treated with zinc powder (2 g) and ammonium chloride (2 g) with stirring at room temperature. After stirring 3 hr, the reaction is filtered and the filtrate evaporated under vacuum (less than 20 torr). The residue is partitioned between ethyl acetate and 5% aqueous sodium bicarbonate. The organic layer is separated, dried (sodium sulfate) and concentrated under vacuum leaving the product 13-(β-phenyl-isoserinyl)-baccatin III (11A).

Preparation No. 31: Preparation of 13-(N-Boc-β-phenyl isoserinyl)-baccatin III (10BA)

A 68 mg (0.09 mM) quantity of 13-(β-phenyl-isoserinyl)-baccatin III (Preparation No. 24; 11A) is stirred at room temperature under nitrogen in 0.5 mL dry THF. To this is added 20 mg (0.092 mM) di-t-butyl-dicarbonate in 0.2 mL dry THF and 0.013 mL (0.093 mM) triethylamine. The reaction is allowed to react for 24 hours; TLC after 5 hours shows the reaction to be mostly done.

The reaction mixture is partitioned between ethyl acetate-brine. The layers are separated and the aqueous layer reextracted with ethyl acetate. The organic layers are combined, dried over sodium sulfate and evaporated under vacuum.

The crude product is chromatographed over 10 g silica gel, eluting with 60-40 ethyl acetate-hexane. Fractions of 2 mL are collected, analyzing them by TLC. Fractions 12–30 contain the product and are combined and evaporated under vacuum. This produces the title compound, 10BA, as a white solid.

TLC: silica gel 60; 60-40 EtOAc-hexane; Rf: 0.46.
$^1$H NMR (CDCl$_3$, TMS) δ 1.15 (s, 3H); 1.33 (s, 9H); 1.85 (s, 3H); 2.25 (s, 3H); 2.30 (m); 2.38 (s, 3H); 2.54 (m); 3.46 (d, 1H); 3.80 (d, 1H); 4.17 (d, 1H); 4.31 (d, 1H); 4.41 (m, 1H); 4.63 (bs, 1H); 4.95 (d, 1H); 5.28 (bd, 1H); 5.42 (bd, 1H); 5.67 (d, 1H); 6.24 (t, 1H); 6.29 (s, 1H); 7.18 (d, 1H); 7.38 (m, 5H); 7.50 (t, 2H); 7.62 (t, 1H); 8.10 (d, 2H).

Preparation No. 32: Preparation of 13-(N-(1-adamantoyl)-β-phenyl isoserinyl)-baccatin III (10EA)

A 44 mg (0.06 mM) quantity of 13-(β-phenyl-isoserinyl)-baccatin III (Preparation No. 24; 11A) is stirred at 0° C. under nitrogen in 1 mL dry pyridine. To this is added 0.2 ml methylene chloride containing 13 mg (0.06 mM) 1-adamantane-carbonyl chloride. After 30 minutes reaction, TLC shows the reaction to be complete.

The reaction is partitioned between 1N HCl-ethyl acetate. The organic layer is washed with brine, dried over sodium-sulfate and evaporated under vacuum.

The residue is chromatographed over 5 g silica gel, eluting with 65-35 EtOAc-hexane. Fractions of 2 mL are collected, analyzing them by TLC. The product is found in fractions 8–23, which upon combining and evaporating leave 33 mg (60% yield) white solid. Spectral data still showed the presence of 1-adamantane carboxylic acid.

The impure product is dissolved in 1 mL freshly distilled THF. Excess ethereal diazomethane is added and the reaction left to react for 30 minutes. The reaction is then evaporated under vacuum and chromatographed as before. Pure product is found in fractions 6–25, which upon evaporation leave 13-(N-(1-adamantoyl)-β-phenyl isoserinyl)-baccatin III 10EA, as a solid.

TLC: silica gel 60; 50-50 EtOAc-hexane; Rf: 0.48.
Mass Spec (FAB, m/z): (M+H) measured at 912.4168; theory for C$_{51}$H$_{62}$N$_1$O$_{14}$ is 912.4170; 912, 852, 834, 569, 551, 509, 344, 326, 298, 268, 180, 135, 105. $^1$H NMR (CDCl$_3$, TMS) δ 1.16 (s); 1.27 (s); 1.60–2.10 (m); 2.24 (s, 3H); 2.30 (m); 2.36 (s, 3H); 2.52 (m); 3.54 (d, 1H); 3.77 (d, 1H); 4.18 (d, 1H); 4.29 (d, 1H); 4.40 (m,1H); 4.68 (m, 1H); 4.94 (d, 1H); 5.56 (dd, 1H); 5.68 (d, 1H); 6.15 (t, 1H); 6.28 (s, 1H); 6.47 (d, 1H); 7.37 (m, 5H); 7.50 (t, 2H); 7.61 (t, 1H); 8.10 (d, 2H).

Preparation No. 33: Preparation of 13-(N-(3-tetrahydrofuranyloxycarbonyl)-β-phenyl isoserinyl)-baccatin III (10FA)

13-(β-phenyl-isoserinyl)-baccatin III (Preparation No. 24; 11A) 16.8 mg, 0.022 mM) is treated with racemic 3-tetrahydrofuranol succinimidyl carbonate (5.0 mg, 0.023 mM), pyridine (5 μL), and methylene chloride (180 μL). The reaction is stirred at room temperature 2 days. It is diluted with ethyl acetate and washed with 5% aqueous sodium bisulfate and 5% aqueous sodium bicarbonate. The organic solution was dried and evaporated to give a mixture of diastereomers, 13-(N-(3-tetrahydrofuranyloxycarbonyl)-β-phenyl isoserinyl)-baccatin III (10FA).

TLC: silica gel 60; 40-60 acetone hexane; Rf: 0.16.
$^1$H NMR (CDCl$_3$, TMS) δ 1.16 (s); 1.27 (s); 1.68 (s+m); 1.83 (s); 1.90 (m); 2.25 (s+m); 2.37 (s); 2.55 (m); 3.7–4.0 (m); 4.18 (d, 1H); 4.30 (d, 1H); 4.43 (m,1H); 4.64 (m, 1H); 4.95 (dd, 1H); 5.09 (m, 1H); 5.30 (m, 1H); 5.67 (m, 2H); 6.28 (s+m, 2H); 7.39 (m, 5H); 7.50 (m, 2H); 7.62 (m, 1H); 8.12 (d, 2H).

Preparation No. 34: Preparation of 13-(N-(4-tetrapyranyloxycarbonyl)-β-phenyl isoserinyl)-baccatin III (10GA)

13-(β-phenyl-isoserinyl)-baccatin III (Preparation No. 24; 11A, 10 mg, 0.013 mM) is treated with 4-tetrahydropyranol succinimidyl carbonate (3.3 mg, 0.014 mM), pyridine (5 μL)

and methylene chloride (100 μL). The mixture is stirred overnight at room temperature. The reaction is diluted with ethyl acetate and washed with 5% aqueous sodium bisulfate and 5% aqueous sodium bicarbonate. The ethyl acetate solution is dried and evaporated, giving 10.3 mg crude product. Purification by column chromatography on silica gel in (40-60) acetone-hexane yields pure 13-(N-(4-tetrapyranyl-oxycarbonyl)-β-phenyl isoserinyl)-baccatin III (10GA).

TLC: silica gel 60; 40-60 acetone hexane; Rf: 0.17.

$^1$H NMR (CDCl$_3$, TMS) δ 1.15 (s); 1.27 (s); 1.5–1.8 (m); 1.68 (s); 1.84 (s); 1.89 (m); 2.1–2.4 (m); 2.25 (s, 3H); 2.41 (s, 3H); 2.49 (d, 1H); 2.55 (m, 1H); 3.08 (m, 1H); 3.27 (m, 1H); 3.33 (d, 1H); 3.70 (m, 1H); 3.80 (d+m, 2H); 4.16 (d, 1H); 4.29 (d, 1H); 4.42 (m,1H); 4.66 (m, 2H); 4.94 (d, 1H); 5.33 (m, 1H); 5.57 (m, 1H); 5.65 (d, 1H); 6.28 (s+m, 2H); 7.37 (m, 5H); 7.51 (m, 2H); 7.61 (m, 1H); 8.14 (d, 2H).

Preparation No. 35 Preparation of 13-(N-(tert-butylacetyl)-β-phenyl isoserinyl)-baccatin III (10HA) and 2'-t-butylacetyl-13-(N-(tert-butylacetyl)-β-phenyl isoserinyl)-baccatin III (12CA)

A 51 mg (0.068 mM) quantity of 13-(β-phenyl-isoserinyl)-baccatin III (Preparation No. 24; 11A) is stirred under nitrogen at 0° C. in 1 mL dry pyridine. A 0.01 mL quantity (9.1 mg, 0.068 mM) of tert-butylacetyl chloride is dissolved in 0.1 mL methylene chloride. This solution is added dropwise to the starting amine. The reaction is allowed to react at 0° C. for 3 hours and in the freezer overnight.

The reaction is diluted with ethyl acetate and washed with 1N HCl and 5% sodium bicarbonate. The aqueous layers are backextracted with ethyl acetate. The organic layers are combined, dried over sodium sulfate and evaporated under vacuum.

The crude product is chromatographed over 7 g silica gel, eluting with 50-50 and 70-30 EtOAc-hexane. Fractions of 2 mL are collected, analyzing them by TLC. The following fractions are combined and evaporated under vacuum.

Fr. 11–21, impure 2'-t-butylacetyl-13-(N-(tert-butylacetyl)-β-phenyl isoserinyl)-baccatin III (12CA)

Fr. 22–45, 13-(N-(tert-butylacetyl)-β-phenyl isoserinyl)-baccatin III (10HA), white solid.

12CA is still impure and is rechromatographed over 3 g silica gel, eluting with 10-90 acetone-methylene chloride. Fractions of 1 mL are collected, analyzing them by TLC. Fractions 11–28 contained the product and are combined and evaporated under vacuum to give pure 2'-t-butylacetyl-13-(N-tert-butylacetyl)-β-phenyl isoserinyl)-baccatin III (12CA) as a white solid. Data for 12CA:

TLC: silica gel 60; 60-40 ethyl acetate-hexane; Rf: 0.70.

Mass Spec (FAB, m/z) (M+H) measured at 946.4618; theory for $C_{52}H_{68}N_1O_{15}$ is 946.4589; 946, 509, 378, 360, 280, 262, 234, 105, 99, 57, 43. $^1$H NMR (CDCl$_3$, TMS) δ 0.98 (s); 1.28 (s, 3H); 2.23 (s, 3H); 2.42 (s, 3H); 2.53 (m); 3.81 (d, 1H); 4.19 (d, 1H); 4.31 (d, 1H); 4.45 (m, 1H); 4.97 (d, 1H); 5.34 (d, 1H); 5.69 (d, 1H); 5.75 (m, 1H); 6.08 (d, 1H); 6.24 (m, 1H); 6.31 (s, 1H); 7.28–7.45 (m, 5H); 7.51 (t, 2H); 7.61 (t, 1H); 8.11 (d, 2H).

Data for 10HA:

TLC: silica gel 60; 60-40 ethyl acetate-hexane; Rf: 0.27

Mass Spec (FAB, m/z) (M+H) measured at 848.3863; theory for $C_{46}H_{58}N_1O_{14}$ is 848.3857; 848, 830, 788, 770, 569, 551, 509, 280, 262, 234, 182, 136, 115, 105, 99. 57, 43. $^1$H NMR (CDCl3, TMS) δ 0.97 (s); 1.26 (s, 3H); 2.24 (s, 3H); 2.33 (s, 3H); 2.52 (m, 2H); 3.60 (d, 1H); 3.78 (d, 1H); 4.18 (d, 1H); 4.29 (d, 1H); 4.39 (m, 1H); 4.65 (m, 1H); 4.93 (d, 1H); 5.55 (dd, 1H); 5.67 (d, 1H); 6.19 (t, 1H); 6.28 (s, 1H); 7.39 (m, 5H); 7.50 (t, 2H); 7.62 (t, 1H); 8.10 (d, 2H).

Preparation No. 36: Preparation of 13-(N-(pivaloyl)-β-phenyl isoserinyl)-baccatin III (10IA)

A 44 mg (0.06 mM) quantity of 13-(β-phenyl-isoserinyl)-baccatin III (Preparation No. 24; 11A) is stirred at 0° C. under nitrogen in 1 mL dry pyridine. To this is added over 5 min a solution of 8 mg (0.06 mM) trimethylacetyl chloride in 0.2 mL methylenechloride. After 30 minutes reaction, TLC shows most of the amine to have reacted.

The reaction is partitioned between 1N HCl-ethyl acetate. The organic layer is washed with brine, dried over sodium sulfate and evaporated under vacuum.

The crude product is chromatographed over 5 g silica gel, eluting with (65-35) EtOAc-hexane. Fractions of 2 mL are collected, analyzing them by TLC. The product is found in fractions 10–38, which upon combining and evaporating under vacuum yields the title compound.

Spectral data indicates the presence of a small amount of pivalic acid. Therefore, the product is dissolved in ethyl acetate, washed with 5% sodium bicarbonate, dried over sodium sulfate and evaporated under vacuum. This yields 10IA, as a white solid.

TLC: silica gel 60; 50-50 EtOAc-hexane; Rf: 0.29.

Mass Spec (FAB, m/z) (M+H) measured at 834.3712; theory for $C_{45}H_{56}N_1O_{14}$ is 834.3700; 834, 816, 774, 569, 551, 509, 387, 327, 266, 248, 220, 190, 105, 57. $^1$H NMR:(CDCl$_3$, TMS) δ 1.16 (s): 1.23 (s); 2.23 (s, 3H); 2.29 (d, 1H); 2.35 (s, 3H); 2.51 (m, 1H); 3.77 (d, 1H); 4.17 (d, 1H); 4.28 (d, 1H); 4.38 (m, 1H); 4.68 (d, 1H); 4.93 (d, 1H); 5.56 (dd, 1H); 5.66 (d, 1H); 6.17 (m, 1H); 6.28 (s, 1H); 6.54 (d, 1H); 7.35 (m, 5H); 7.49 (m, 2H); 7.60 (m, 1H); 8.10 (d, 2H).

Preparation No. 39 Preparation of 7-Fluoro-13-(N-Cbz-β-phenyl-isoserinyl)-baccatin III (18) from 7-Fluoro-13-(N-Cbz-β-phenyl-isoserinyl)-2'-troc-baccatin III (13BA)

A solution of 7-fluoro-13-(N-Cbz-β-phenyl-isoserinyl)-2'-troc-baccatin III (13BA. Example 3) (0.079 g) in 9:1 methanol/acetic acid (20 mL) and ethyl acetate (8 mL) is stirred with activated zinc (0.153 g) at room temperature for two hours. Following workup, the crude product is chromatographed over silica gel using 40% EtOAc-hexane for elution to give 7-fluoro-13-(N-Cbz-β-phenyl-isoserinyl)-baccatin III (18): mass spectrum, 886, 571, 511, 371, 347, 329, 316, 298, 105, 91 m/z.

Preparation No. 40: Preparation of 7-Fluoro-13-(β-phenyl isoserinyl)-baccatin III (19)

A 23.5 mg (0.027 mM) quantity 7-Fluoro-13-(N-Cbz-β-phenyl-isoserinyl)-baccatin III (Preparation No. 39, 18,) is dissolved in 3 mL absolute ethanol and the solution treated with 7 mg 10% Pd/C and hydrogenated at atmospheric pressure and room temperature for 4.5 hours. The disappearance of starting material is followed by TLC. The reaction is filtered through Celite, washing the Celite with ethyl acetate. The combined filtrate and wash are evaporated under vacuum. The residue is treated twice with ethyl acetate-hexane and evaporated under vacuum. This yields 7-Fluoro-13-(β-phenyl isoserinyl)-baccatin III (19) as a white solid.

TLC: silica gel 60; 50-50 ethyl acetate-hexane; Rf: 0.11.

$^1$H NMR (CDCl$_3$, TMS): δ 2.20 (s, 3H); 2.26 (s, 3H); 2.54 (m, 1H); 3.99 (d, 1H); 4.24 (d, 1H); 4.27–4.42 (m, 3H); 4.55 (dd, J=48 Hz, J=5 Hz, 1H); 4.99 (d, 1H); 5.72 (d, 1H); 6.11 (m, 1H); 6.55 (s, 1H); 7.27 (s, 1H); 7.39 (m, 4H); 7.51 (m, 2H); 7.64 (m, 1H); 8.08 (d, 2H).

Preparation No. 41: Preparation of 7-Fluoro-13-(N-Boc-β-phenyl isoserinyl)-baccatin III (20) and 7-Fluoro-2'-Boc-13-(N-Boc-β-phenyl isoserinyl)-baccatin III (13CA)

A 0.027 mM quantity 7-Fluoro-13-(β-phenyl isoserinyl)-baccatin III (Preparation No. 40; 19) is dissolved with stirring in 0.2 mL freshly distilled THF at room temperature and under nitrogen. Add 6 mg (0.027 mM) di-tert-butyl dicarbonate and 0.004 mL (0.029 mM) triethylamine. Left to react for 20 hours.

The reaction is partitioned between ethyl acetate-brine. The layers are separated and the aqueous layer reextracted with ethyl acetate. The organic layers are combined, dried over sodium sulfate and evaporated under vacuum.

The product mixture is chromatographed over 3 g silica gel, eluting with 30-70 ethyl acetate-hexane until the first product comes off and then switching to 50-50 ethyl acetate-hexane. Fractions of 1 mL are collected, analyzing them by TLC. The following fractions are combined and evaporated to leave white solids.

Fr. 16–30, 13CA
Fr. 32–46, 20

Data for 13CA:

TLC: silica gel 60; 50-50 ethyl acetate-hexane; Rf: 0.83

Mass Spec (FAB, m/z) 952 (M+H), 878, 822, 778, 571, 511, 389, 329, 106, 162, 105, 57. $^1$H NMR (CDCl$_3$, TMS): δ 1.17 (s, 3H); 1.24 (s, 3H); 1.25 (s, 9H); 1.90 (s, 9H); 2.08 (s, 3H); 2.22 (s, 3H); 2.0–2.7 (m, 4H); 4.02 (d, 1H); 4.24 (d, 1H); 4.36 (d, 1H); 4.59 (dd, J=48 Hz, J=5 Hz, 1H); 4.77 (bs, 1H); 5.02 (d, 1H); 5.22 (bs, 1H); 5.68 (m, 1H); 5.77 (d, 1H); 6.27 (m, 1H); 6.57 (s, 1H); 7.27–7.70 (m, 9H); 8.09 (d, 2H).

Data for 20:

TLC: silica gel 60; 50-50 ethyl acetate-hexane; Rf: 0.54

Mass Spec (FAB, m/z): (M+H) measured at 852.3638; theory for $C_{45}H_{55}F_1N_1O_{14}$ is 852.3606; 852, 796, 752, 692, 674, 571, 511, 389, 347, 329, 105, 57, 43. $^1$H NMR (CDCl$_3$, TMS): δ 1.17 (s, 3H); 1.23 (s, 3H); 1.34 (s, 9H); 2.22 (s, 3H); 2.39 (s, 3H); 2.0–2.7 (m, 4H); 3.36 (m, 1H); 4.04 (d, 1H); 4.28 (d, 1H); 4.37 (d, 1H); 4.48–4.68 (m, 2H); 5.01 (d, 1H); 5.30 (m, 1H); 5.45 (m, 1H); 5.76 (d, 1H); 6.21 (m, 1H); 6.56 (s, 1H); 7.30–7.70 (m, 9H); 8.13 (d, 2H).

Preparation No. 42 Preparation of 13-(N-Benzyloxycarbonyl-β-phenyl-isoserinyl)-7-deoxy-7β,8β-methanobaccatin III (21) from 13-(N-Benzyloxycarbonyl-β-phenyl-isoserinyl)-2'-troc-7-deoxy-7β,8β-methanobaccatin III (14BA)

A solution of 13-(N-benzyloxycarbonyl-β-phenyl-isoserinyl)-2'-troc-7-deoxy-7β,8β-methanobaccatin III (14BA, Example 3) (0.040 g) in 9:1 methanol/acetic acid (10 mL) is stirred at room temperature with activated zinc (0.144 g) for 3 hours. Following workup, the crude reaction product is chromatographed over silica gel using 40% EtOAc-hexane for elution to give 13-(N-benzoyloxycarbonyl-β-phenyl-isoserinyl)-7-deoxy-7β,8β-methanobaccatin III (21):

mass spectrum, found: 866.3423, $C_{48}H_{51}NO_{14}$+H requires 866.3388, 848, 806, 788, 551, 533, 491, 105, 91 m/z.

Preparation No. 43: Preparation of 13-(β-phenyl isoserinyl)-7-deoxy-7β,8β-methanobaccatin III (22)

A 14 mg (0.016 mM) quantity of 13-(N-benzylozycarbonyl-β-phenyl isoserinyl)-7-deoxy-7β,8β-methanobaccatin III Preparation No. 42, 21) is dissolved in 2 mL absolute ethanol. Add 5 mg 10% Pd/C and hydrogenate at room temperature and atmospheric pressure for 6 hours. The reaction is followed by TLC and upon completion is filtered through Celite, washing with ethyl acetate. The filtrate and wash is combined and evaporated under vacuum. Add ethyl acetate-hexane twice, reevaporating, to give 22 as a white solid. Stored in freezer overnight to be used as is in Preparation No. 44.

TLC: silica gel 60; 50-50 EtOAc-hexane; Rf: streak from origin partly up the plate.

$^1$H NMR (CDCl$_3$, TMS) δ 5.62 (d, 1H); 6.11 (t, 1H); 6.31 (s, 1H); 7.39 (m); 7.53 (m, 2H); 7.66 (m, 1H); 8.08 (d, 2H).

Preparation No. 44: Preparation of 13-(N-Boc-β-phenyl isoserinyl)-7-deoxy-7β,8β-methanobaccatin III (23) and 13-(N-Boc-2'-Boc-β-phenyl isoserinyl)-7-deoxy-7β,8β-methanobaccatin III (14CA)

A 0.016 mM quantity of 22 (Preparation No. 44) is dissolved with stirring under nitrogen in 0.12 mL dry THF. To this is added 3.5 mg (0.016 mM) di-t-butyl dicarbonate in 0.05 mL dry THF and 0.0025 mL (0.018 mM) triethyl amine in 0.015 mL dry THF. Left to react for 27 hours, when TLC shows the reaction to be fairly complete.

The reaction mixture is partitioned between ethyl acetate-brine. The layers are separated and the aqueous layer reextracted with ethyl acetate. The combined organic layers are dried over sodium sulfate and evaporated under vacuum.

The crude product mixture is chromatographed over 3 g silica gel. Eluted with a gradient of 30-70 to 50-50 EtOAc-hexane. Fractions of 1 mL are collected. analyzing them by TLC. The following fractions are combined and evaporated, giving white solids.

Fr. 16–30, 14CA
Fr. 33–53, 23

23 is not quite pure and is rechromatographed over 1 g silica gel, eluting with a gradient of 40-60 to 50-50 EtOAc-hexane. Fractions of 0.5 mL were collected and analyzed by TLC. Pure product is found in fractions 11–20, which upon combining and evaporating under vacuum leave the desired product as a white solid 4 mg.

Data for 14CA:

TLC: silica gel 60; 50-50 EtOAc-hexane; Rf: 0.87

Mass Spec (FAB, m/z) 858, 803, 798, 551, 491, 369, 327, 206, 105, 57. $^1$H NMR: (CDCl$_3$, TMS) δ 1.25 (s); 2.01 (s, 3H); 2.21 (s, 3H); 2.43 (m); 4.01 (d, 1H); 4.07 (d, 1H); 4.28 (d, 1H); 4.70 (m, 2H); 5.18 (bs, 1H); 5.64 (m, 2H); 6.25 (m, 1H); 6.33 (s, 1H); 7.39 (m, 5H); 7.51 (m, 2H); 7.64 (m, 1H); 8.09 (d, 2H).

Data for 23:

TLC: silica gel 60; 50-50 EtOAc-hexane; Rf: 0.77

Mass Spec (FAB, m/z) : (M+H) measured: 832.3588; theory for $C_{45}H_{54}N_1O_{14}$ is 832.3544; 832, 814, 776, 732, 714, 696, 672, 551, 491, 105, 57. $^1$H NMR: (CDCl$_3$, TMS) δ 1.28 (s); 1.37 (m); 1.68 (m); 1.85 (s); 2.10 (m); 2.21 (s, 3H); 2.26 (m); 2.39 (s, 3H); 2.47 (m); 3.30 (m, 1H); 4.06 (m, 2H); 4.31 (d, 1H); 4.63 (m, 1H); 4.74 (d, 1H); 5.30 (m, 1H); 5.36 (d, 1H); 5.66 (d, 1H); 6.28 (m, 1H); 6.33 (s, 1H); 7.37 (m, 5H); 7.51 (m, 2H); 7.61 (m, 1H); 8.15 (d, 2H).

Preparation No. 45: Preparation of 13-(N-phenyl urea-β-phenyl-isoserinyl)-baccatin III; 13-(β-phenyl-isoserinyl)-baccatin III N-phenyl urea (10JA)

A 48 mg (0.064 mM) quantity of 13-(β-phenyl-isoserinyl)-baccatin III (Preparation No. 24; 11A) is dissolved in 700 µL THF and 6.5 µL (0.060 mM) phenyl isocyanate added. TLC shows no amine remained. The solution is diluted with EtOAc and extracted with sat. CuSO$_4$. The organic layer is filtered through Na$_2$SO$_4$ and concentrated in vacuo and chromatographed over 5 gm of silica gel packed in 1:1 EtOAc:Hexane. The column is eluted with 20 mL 1:1 EtOAc:Hexane, 20 mL 3:2 EtOAc:Hexane, and 20 mL 2:1 EtOAc:Hexane collecting 3 mL fractions. The desired product is found in fractions 17–31.

Mass Spec (FAB-High Res.) Theory: 869.3496 Found: 869.3512 $^1$H NMR (CDCl$_3$; TMS): δ 1.13 (s,3H); 1.19 (s,3H); 1.81 (s,3H); 2.19 (s,3H); 2.27 (m); 2.37 (s,3H); 2.51 (m,1H); 2.66 (m,1H); 3.76 (d,1H); 4.18 (d,1H); 4.28 (d,1H): 4.37 (m,1H); 4.67 (m,1H); 4.93 (d,1H); 5.49 (dd,1H); 5.67

(d,1H); 6.21 (m,1H); 6.27 (s,1H); 6.93 (m,2H); 7.07 (m,2H); 7.19 (m,3H); 7.26–7.40 (m); 7.48 (m,1H); 7.60 (m,1H); 8.10 (d,2H)

Preparation No. 46: Preparation of N-debenzoyl-N-(t-butyl) aminocarbonyl-taxol; 13-β-phenyl-isoserinyl)-baccatin III N-t-butyl urea (10KA)

N-debenzoyl-N-(t-butyl)aminocarbonyl-taxol (51 mg, 0.07 mM; Preparation No. 24, 11A) is dissolved in 700 μL THF and 7 μL (0.061 mM) t-butyl isocyanate is added. TLC shows some amine remaining so another 3 μL is added. This is repeated twice more until TLC shows little amine left (3 μL and 4 μL). The solution is concentrated in vacuo and the residue chromatographed over 5 gm of silica gel packed in 1:1 EtOAc:hexane. The column is eluted with 50 mL 1:1 EtOAc:hexane, 25 mL 3:2 EtOAc:hexane, and 25 mL 2:1 EtOAc:hexane collecting 3 mL fractions. The desired product is found in fractions 21–40.

Mass Spec (FAB-High Res.) Theory: 849.3809 Found: 849.3809 $^1$H NMR (CDCl$_3$; TMS): δ 1.14 (s,3H); 1.22 (s); 1.24 (s); 1.83 (s,3H); 2.23 (s,3H); 2.44 (s,3H); 2.50 (m,1H); 3.77 (d,1H); 4.17 (d,1H); 4.29 (d,1H); 4.38 (m,1H); 4.61 (m,1H); 4.94 (d,1H); 5.29 (m,2H); 5.67 (d,1H); 6.18 (m,1H); 6.29 (s,1H); 7.33 (m,5H); 7.49 (m,1H); 7.61 (m,1H); 8.09 (d,2H)

Preparation No. 47: Preparation of 13-(N-1-methyl-1-cyclohexamide-β-phenyl-isoserinyl)-baccatin III; 13-(N-(1-methyl-1-cyclohexanoyl)-β-phenyl-isoserinyl)-baccatin III (10MA)

A 30 mg (0.04 mM) quantity of 13-(β-phenyl-isoserinyl)-baccatin III (Preparation No. 24; 11A) is dissolved in 400 μL pyridine and cooled to 0° C. Once cooled 20 μL of 300 mg per 1 ml of 1-methyl-1-cyclohexyl carbonyl chloride in CH$_2$Cl$_2$ (0.037 mM) is added. TLC showed some amine remained so another 10 μL added. TLC shows little amine left. The solution is diluted with EtOAc and extracted with sat. CuSO$_4$. The organic layer is filtered through Na$_2$SO$_4$ and concentrated in vacuo and chromatographed over 3 gm of silica gel packed in 1:1 EtOAc:Hexane. The column is eluted with 50 mL 1:1 EtOAc:Hexane and 20 mL 3:2 EtOAc:Hexane collecting 2 mL fractions. The desired product is found in fractions 11–28.

Mass Spec (FAB-High Res.) Theory: 874.4013 Found: 874.4011 $^1$H NMR (CDCl$_3$; TMS): δ 1.12 (s,3H); 1.15 (s,3H); 1.26 (s,3H); 1.81 (s,3H); 1.87 (m,3H); 2.24 (s,3H); 2.36 (s,3H); 2.54 (m,1H); 3.78 (d,1H); 4.18 (d,1H); 4.29 (d,1H); 4.40 (m,1H); 4.70 (d,1H); 4.94 (d,1H); 5.61 (dd,1H); 5.67 (d,1H); 6.19 (m,1H); 6.28 (s,1H); 6.51 (d,1H); 7.38 (m,5H); 7.50 (m,2H); 7.61 (m,1H); 8.11 (d,2H)

Preparation No. 48: Preparation of 13-(N-1-phenyl-1-cyclopentamide-β-phenyl-isoserinyl)-baccatin III; 13-(N-(1-phenyl-1-cyclopentanoyl)-β-phenyl-isoserinyl)-baccatin III (10NA)

A 26 mg (0.035 mM) quantity of 13-(β-phenyl-isoserinyl)-baccatin III (Preparation No. 24: 11A) is dissolved in 400 μL pyridine and cooled to 0° C. Once cooled 20 μL of 350 mg per 1 mL of 1-phenyl-1-cyclopentyl carbonyl chloride in CH$_2$Cl$_2$ (0.033 mM) was added. TLC showed some amine remained so another 20 μL added. TLC showed no amine. The solution is diluted with EtOAc and extracted with sat CuSO$_4$. The organic layer is filtered through Na$_2$SO$_4$ and concentrated in vacuo and chromatographed over 3 gm of silica gel packed in 1:1 EtOAc:Hexane. The column is eluted with 50 mL 1:1 EtOAc:Hexane and 25 mL 3:2 EtOAc:Hexane collecting 2 mL fractions. The desired product is found in fractions 12–29.

Mass Spec (FAB-High Res.) Theory: 922.4013 Found: 922.4022 $^1$H NMR (CDCl$_3$; TMS): δ 1.16 (s,3H); 1.27 (s,3H); 1.77 (s,3H); 1.60–2.10 (m); 2.25 (s,3H); 2.35 (s,3H); 2.25–2.65 (m); 3.75 (d,1H); 4.19 (d,1H); 4.28 (d,1H); 4.38 (m,1H); 4.59 (d,1H); 4.92 (d,1H); 5.49 (dd,1H); 5.66 (d,1H); 6.10 (m,2H); 6.26 (s,1H); 7.08 (m,2H); 7.29 (m); 7.53 (m,2H); 7.63 (m,1H); 8.12 (d,2H)

Preparation No. 49: Preparation of 13-(N-phthalimide-β-phenyl-isoserinyl)-baccatin III; 13-(β-phenyl-isoserinyl)-baccatin III N-phthalimide (10PA)

A 29 mg (0.04 mM) quantity of 13-(β-phenyl-isoserinyl)-baccatin III (Preparation No. 24; 11A) is dissolved in 400 μL pyridine and 15 mg (0.07 mM) carbethoxyphthalimide. The reaction is checked by TLC and after 72 hours no amine is seen. The solution is diluted with EtOAc and extracted with sat. CuSO$_4$. The organic layer is filtered through Na$_2$SO$_4$ and concentrated in vacuo and chromatographed over 4 gm of silica gel packed in 1:1 EtOAc:Hexane. The column is eluted with 20 mL 1:1 EtOAc:Hexane, 20 mL 3:2 EtOAc:Hexane, 20 mL 2:1 EtOAc:Hexane, and 20 mL 4:1 EtOAc:Hexane collecting 2 mL fractions. The desired product is found in fractions 16–28.

$^1$H NMR(CDCl$_3$; TMS): δ 1.09 (s,3H); 1.16 (s,3H); 1.81 (s,3H); 2.21 (s,3H); 2.44 (s,3H); 2.52 (m,2H); 3.76 (d,1H); 4.15 (d,1H); 4.28 (d,1H); 4.41 (m,2H); 4.96 (d,1H); 5.31 (m,1H); 5.61 (d,1H); 5.76 (d,1H); 6.08 (m,1H); 6.24 (s,1H); 7.23 (m,1H); 7.36 (m,2H); 7.52 (m,4H); 7.66 (m,1H); 7.80 (m,4H); 8.10 (d,2H)

Preparation No. 50: Preparation of N-debenzoyl-N-(t-butyl) aminothiocarbonyl-taxol (10LA)

A 24 mg (0.032 mM) quantity of 13-(β-phenyl-isoserinyl)-baccatin III (Preparation No. 24; 11A) is stirred at room temperature under nitrogen in 0.2 mL dry THF. A 4 uL quantity (0.032 mM) t-butyl-isothiocyanate is added. TLC after 5 hours shows the reaction to be incomplete. An additional 4 uL t-butyl-isothiocyanate is added and the reaction allowed to proceed overnight. The crude product is coated on 0.5 g silica gel and chromatographed over 3 g silica gel, eluting with 60-40 ethyl acetate-hexane. Fractions of 1 mL are collected, analyzing them by TLC. Fractions 7–20 contain the product and are combined and evaporated under vacuum to yield the desired product.

TLC: silica gel 60; 60-40 EtOAc-hexane; Rf: 0.40.

$^1$H NMR (CDCl$_3$, TMS) δ 1.14 (s, 3H); 1.40 (s, 9H); 1.80 (s, 3H); 2.25 (s, 3H); 2.40 (s, 3H); 3.50 (s, 1H); 3.80 (d, 1H); 4.23 (m, 2H); 4.40 (bs, 1H); 4.86 (s, 1H); 4.93 (d, 1H); 5.66 (d, 1H); 6.18 (s, 1H); 6.27 (s, 1H); 6.28–6.40 (m, 2H); 6.59 (d, 1H); 7.30–7.54 (m, 7H); 7.58 (t, 1H); 8.09 (d, 2H). Mass Spec (FAB, m/z) (M+H) measured at 865.3577; theory for C$_{45}$H$_{57}$N$_2$O$_{13}$S is 865.3581; 865, 569, 509, 297, 279, 251, 133, 105, 77, 57.

Preparation No. 51: Preparation of Taxotere (10BF) from 10-Acetyl Taxotere (10BA)

A 25 mg (0.029 mM) quantity of 10-acetyl Taxotere (Preparation No. 1, 10BA) is stirred at room temperature under nitrogen in 1.0 mL 95% ethanol. Add 2 drops anhydrous hydrazine and leave to react for 1.5 hours, when TLC showed the reaction to be mostly complete. The reaction is partitioned between water-methylene chloride. The aqueous layer is backextracted with methylene chloride. The organic layers are combined, dried over sodium sulfate and evaporated under vacuum.

The crude product is chromatographed over 3 g silica gel, eluting with 70-30 ethyl acetate-hexane. Fractions of 1 mL are collected, analyzing them by TLC. Fractions 14–28 contain the product and are combined and evaporated under vacuum.

TLC: silica gel 60; 70-30 EtOAc-hexane; Rf: 0.33.

$^1$H NMR (CDCl$_3$, TMS) δ 1.12 (s, 3H); 1.23 (s, 3H); 1.34 (s, 9H); 1.74 (s, 3H); 1.85 (s, 3H); 2.37 (s, 3H); 2.56 (m,

1H); 3.53 (bs, 1H); 3.90 (d, 1H); 4.18 (d, 1H); 4.21 (m, 1H); 4.30 (d, 1H); 4.32 (s, 1H); 4.62 (bs, 1H); 4.94 (d, 1H); 5.23 (s, 1H); 5.28 (bs, 1H); 5.52 (d, 1H ); 5.66 (d, 1H); 6.20 (t, 1H); 7.25–7.45 (m, 6H); 7.50 (t, 2H); 7.61 (t, 1H); 8.11 (d, 2H).

Preparation No. 52: Preparation of 13-(β-phenyl-isoserinyl)-baccatin III N-t-amylurethane (10RA)

Part A: Preparation of t-amyl 4-nitrophenyl carbonate

A solution of t-amyl alcohol (0.54 ml, 5.0 mM) in pyridine (1 mL) was treated at 0° C. with 4-nitrophenyl chloroformate (1.00 g, 4.97 mM). After adding 1.5 mL of methylene chloride, the reaction was stirred at room temperature overnight. The reaction was diluted with toluene and filtered. Impurities crystallized out from methylene chloride-hexane.

NMR δ 0.981 (t, 3H); 1.54 (s, 6H); 1.88 (q, 2H); 7.36 (d, 2H); 8.28 (d, 2H).

Part B:

A 29 mg (0.039 mM) quantity of 13-(β-phenyl-isoserinyl)-baccatin III (Preparation No. 24; 11A) and t-amyl 4-nitrophenyl carbonate (13 mg, 0.051 mM) in pyridine (0.10 mL) are stirred at room temperature 3 days. The reaction is diluted with ethyl acetate and washed with 5% aqueous sodium bisulfate. The ethyl acetate solution is dried over anhydrous sodium sulfate, evaporated, and chromatographed on a column of silica gel (3 g. 230–400 mesh). The column is eluted with ethyl acetate-hexane mixtures. The desired product is not completely pure, and is therefore rechromatographed in an acetone-hexane system.

NMR (CDCL$_3$, TMS): δ 0.86 (t, 3H); 1.15 (s, 3H); 1.27 (s,3H); 1.29 (s,3H); 1.30 (s,3H); 1.68 (s, 3H); 1.85 (s+m, 4H); 2.25 (s+m, 4H); 2.38 (s, 3H); 2.53 (m, 2H); 3.37 (d, 1H); 3.80 (d, 1H); 4.17 (d, 1H); 4.30 (d, 1H); 4.41 (m, 1H); 4.63 (m, 1H); 4.95 (d, 1H); 5.30 (m, 1H); 5.40 (m, 1H); 5.67 (d, 1H); 6.24 (m, 1H); 6.29 (s, 1H); 7.31–7.68 (m, 8H); 8.11 (d, 2H). $^{13}$C-NMR (CDCl$_3$, TMS): 8.16, 9.53, 14.85, 20.85, 21.86, 22.61, 25.25, 25.71, 25.91, 26.73, 33.22, 35.42, 35.56, 43.18, 45.59, 56.05, 58.53, 72.14, 72.36, 73.57, 74.94, 75.55, 76.44, 79.03, 79.28, 81.05, 82.68, 84.37, 126.67, 128.05, 128.68, 128.84, 128.91, 130.16, 132.95, 133.69, 138.28, 142.28, 155.25, 167.03, 170.16, 171.27, 172.92, 203.66.

MS (FAB): (m+H)$^+$=864. Major ions m/z 794, 569, 527, 509, 345, 327.

Preparation No. 53: Preparation of 13-(β-phenyl-isoserinyl)-baccatin III N-neopentylurethane (10UA)

Part A: Preparation of Neopentyl 4-Nitrophenyl Carbonate

A solution of neopentyl alcohol (0.54 ml, 5.01 mM), pyridine (1 mL), 4-nitrophenyl chloroformate (1.00 g, 5.0 mM), and distilled THF (2 mL) in a flame-dried flask is stirred at room temperature 40 h. The reaction is diluted with hexane, filtered and evaporated. The product is chromatographed on silica gel in ethyl acetate-hexane mixtures. The product which elutes from the column is further purified by recrystallization from methylene chloride-hexane.

NMR (CDCl$_3$, TMS): δ 1.02 (s, 9H); 3.99 (s, 2H); 7.39 (d, 2H); 8.29 (d, 2H).

Part B:

A 20 mg (0.027 mM) quantity of 13-(β-phenyl-isoserinyl)-baccatin III (Preparation No. 24; 11A) and neopentyl 4-nitrophenyl carbonate (7.4 mg, 0.031 mM) in pyridine (80 μl) is stirred at room temperature overnight. The reaction is diluted with ethyl acetate and washed 5% aqueous sodium bisulfate. The organic solution is dried over anhydrous sodium sulfate and concentrated. The crude product is chromatographed twice on silica gel, first in acetone-hexane. then in ethyl acetate-hexane mixtures to yield the desired product.

NMR (CDCL3, TMS): δ 0.82 (s, 9H); 1.15 (s, 3H); 1.26 (s, 3H); 1.68 (s, 3H); 1.84 (s+m, 4H); 2.25 (s+m, 4H); 2.38 (s, 3H); 2.52 (m, 2H); 3.40 (d, 1H); 3.61 (d, 1H); 3.72 (m, 1H); 3.79 (d, 1H); 4.18 (d, 1H); 4.29 (d, 1H); 4.41 (m, 1H); 4.66 (m, 1H); 4.94 (d, 1H); 5.33 (m, 1H); 5.59 (m, 1H); 5.66 (d, 1H); 6.28 (s+m, 2H); 7.30–7.70 (m, 8H); 8.12 (d, 2H). $^{13}$C-NMR (CDCl$_3$, TMS): 9.45, 14.74, 20.73, 21.79, 22.47, 26.09, 26.72, 31.32, 35.46, 43.05, 45.50, 56.38, 58.45, 72.03, 73.47, 74.57, 75.42, 76.36, 79.02, 81.00, 84.28, 126.61, 128.09, 128.58, 128.79, 128.96, 130.11, 132.97, 133.61, 138.10, 141.97, 156.30, 166.91, 170.23, 171.14, 172.47, 203.50. MS (FAB): (m+H)$^+$=864. Major ions m/z 569, 551, 509, 327, 296, 250.

Preparation No. 54: Preparation of 13-(β-phenyl-isoserinyl)-baccatin III N-(2-chloro-1,1-dimethylethyl)urethane (10SA)

Part A:

A solution of 1-chloro-2-methyl-2-propanol (0.51 mL, 5.0 mM), 4-nitrophenyl chloroformate (0.999 g, 5.00 mM), pyridine (400 μL, 5.0 mM), and THF (2 mL) in a dry flask is stirred at room temperature 40 h. The reaction is diluted with hexane and filtered. The filtrate is evaporated and recrystallized from methylene chloride-hexane to yield the desired product.

NMR (CDCl$_3$, TMS): δ 1.64 (s, 6H): 3.87 (s, 2H); 7.38 (d, 2H); 8.28 (d, 2H).

Part B:

A 28 mg (0.037 mM) quantity of 13-(β-phenyl-isoserinyl)-baccatin III (Preparation No. 24; 11A) and chloro-t-butyl 4-nitrophenyl carbonate (12.0 mg, 0.044 mM) in pyridine (0.10 ml) is stirred at room temperature overnight. The reaction is diluted with ethyl acetate and washed with 5% aqueous sodium bisulfate. The organic layer is dried over anhydrous sodium sulfate and evaporated. The crude product is purified by column chromatography on silica gel in acetone-hexane mixtures.

NMR (CDCL$_3$, TMS): δ 0.82 (s, 9H); 1.15 (s, 3H); 1.26 (s, 3H); 1.68 (s, 3H); 1.84 (s+m, 4H); 2.25 (s+m, 4H); 2.38 (s, 3H); 2.52 (m, 2H); 3.40 (d, 1H); 3.61 (d, 1H); 3.72 (m, 1H); 3.79 (d, 1H); 4.18 (d, 1H); 4.29 (d, 1H); 4.41 (m, 1H); 4.66 (m, 1H); 4.94 (d, 1H); 5.33 (m, 1H); 5.59 (m, 1H); 5.66 (d, 1H); 6.28 (s+m, 2H); 7.30–7.70 (m, 8H); 8.12 (d, 2H). $^{13}$C-NMR (CDCl$_3$, TMS): 9.45, 14.74, 20.73, 21.79, 22.47, 26.09, 26.72, 31.32, 35.46, 43.05, 45.50, 56.38, 58.45, 72.03, 73.47, 74.57, 75.42, 76.36, 79.02, 81.00, 84.28, 126.61, 128.09, 128.58, 128.79, 128.96, 130.11, 132.97, 133.61, 138.10, 141.97, 156.30, 166.91, 170.23, 171.14, 172.47, 203.50. MS (FAB): (m+H)$^+$=864. Major ions m/z 569, 551, 509, 327, 296, 250.

Preparation No. 55: Preparation of 13-(β-phenyl-isoserinyl)-baccatin III N-(3-Methyl-3-pentyl)urethane (10TA)

Part A: Preparation of 3-Methyl-3-pentyl 4-Nitrophenyl Carbonate

A mixture of 3-methyl-3-pentanol (0.62 mL, 5.0 mM), 4-nitrophenyl chloroformate (1.01 g, 5.0 mM), THF (2 mL), and pyridine (1 mL) is stirred at room temperature 40 h. Acetonitrile (2 mL) is added and stirring continued overnight. The reaction is diluted with methylene chloride and hexane, filtered and evaporated. The product is chromatographed on silica gel in ethyl acetate-hexane mixtures.

NMR (CDCl$_3$, TMS): δ 0.95(t, 6H);1.50 (s, 3H);1.90 (m, 4H); 7.35(d, 2H); 8.27 (d, 2H).

Part B:

A 32 mg (0.043 mM) quantity of 13-(β-phenyl-isoserinyl)-baccatin III (Preparation No. 24; 11A) and 3-methyl-3-pentyl 4-nitrophenyl carbonate (12.5 mg, 0.047 mM) in pyridine (0.15 mL) is stirred at room temperature 60 h. The reaction is diluted with ethyl acetate and washed with 5% aqueous sodium bisulfate, dried over anhydrous sodium sulfate and evaporated. The product is purified by column chromatography on silica gel in acetone-hexane mixtures.

NMR (CDCL$_3$, TMS): δ 0.76 (t, 6H); 1.15 (s, 3H); 1.24 (s,3H); 1.27 (s,3H); 1.50–1.98 (3 s+m, 12H); 2.25 (s+m, 5H); 2.38 (s, 3H); 2.53 (m, 2H); 3.37 (bs, 1H); 3.80 (d, 1H); 4.17 (d, 1H); 4.30 (d, 1H); 4.41 (m, 1H); 4.64 (m, 1H); 4.95 (d, 1H); 5.29 (m, 1H); 5.42 (m, 1H); 5.66 (d, 1H); 6.24 (m, 1H); 6.29 (s 1H); 7.30–7.70 (m, 8H); 8.11 (d, 2H). $^{13}$C-NMR (CDCl$_3$, TMS): 7.61, 9.27, 14.58, 20.58, 21.63, 22.35, 22.58, 26.46, 30.18, 30.26, 35.15, 35.29, 42.91, 45.31, 55.68, 58.26, 71.88, 72.13, 73.27, 74.71, 75.29, 76.31, 78.78, 80.79, 84.10, 84.95, 126.38, 127.77, 128.41, 128.58, 128.81, 129.90, 132.71, 133.41, 138.06, 142.03, 154.86, 166.70, 169.88, 171.00, 172.68, 203.40. MS (FAB): (m+H)$^+$=878. Major ions m/z 794, 569, 527, 509, 345, 327.

Preparation No. 56 Preparation of N-(t-butylaminocarbonyl)-β-phenyl isoserine methyl ester (3K)

(2R,3S)-β-phenyl-isoserine methyl ester (4.35 g, 22 mM) is dissolved in 100 mL dry THF and the flask cooled to 0° C. To the solution is added t-butyl isocyanate (2.8 mL, 25 mM). TLC after 15 minutes shows some starting material left so another 0.5 mL of the isocyanate is added. TLC after 1 hour shows no starting material so the solvent is concentrated in vacuo leaving N-(t-butylaminocarbonyl)-β-phenyl isoserine methyl ester (3K).

Proton NMR (CDCl$_3$, TMS): δ 1.27 (s,9H); 3.43 (d,1H); 3.81 (s,3H); 4.34 (br s,1H); 4.48 (m,1H); 5.27 (m,1H); 5.32 (m,1H); 7.29 (m,2H); 7.34 (m,3H) Mass spec (FAB-High Res.) Theory for C$_{15}$H$_{22}$N$_2$O$_4$+H: 295.1658 Found: 295.1663

Preparation No. 57 Preparation of (4S,5R)-N-(t-butylaminocarbonyl)2-(2,4-dimethoxyphenyl)-4-phenyl-5-oxazolidinecarboxylic acid methyl ester (5Ka & 5Kb)

N-(t-butylaminocarbonyl)-β-phenyl-isoserine methyl ester (68 mg, 0.23 mM; 3K, Preparation No. 56) is dissolved in 5 mL dry THF and the solution treated with 2,4-dimethoxy benzaldehyde dimethyl acetal (70 mg, 0.33 mM) and pyridinium p-toluenesulfonate (6 mg, 0.02 mM) and the solution warmed to reflux. Approximately 2 mL solvent is boiled away 3 times in a 45 minute period replenishing with 2 mL of fresh THF at which time TLC shows no starting material. The solvent is concentrated in vacuo and chromatographed over 7 gm of silica gel packed in 1:3 EtOAc:Hexane. The column is eluted with 80 mL 1:3 EtOAc:Hexane. 45 mL 1:2 EtOAc:Hexane, 30 mL 2:3 EtOAc:Hexane, and 30 mL 1:1 EtOAc:Hexane collecting 3 mL fractions.

A less polar isomer, (4S,5R)-N-(t-butylaminocarbonyl)-2-(2,4-dimethoxyphenyl)-4-phenyl-5-oxazolidinecarboxylic acid methyl ester (5Ka) is found in fractions 21–31.

Proton NMR (CDCl$_3$, TMS): δ 1.19 (s,9H); 3.82 (s,3H); 3.85 (s,3H); 3.89 (s,3H); 4.68 (br s,1H); 4.88 (d,1H); 5.52 (d,1H); 6.46 (m); 6.70 (s,1H); 7.25–7.50 (m)

Mass spec (FAB-High Res.): Theory for C$_{24}$H$_{31}$N$_2$O$_6$+H: 443.2182 Found: 443.2172

A more polar isomer, (4S,5R)-N-(t-butylaminocarbonyl) 2-(2,4-dimethoxyphenyl)-4-phenyl-5-oxazolidinecarboxylic acid methyl ester (5Kb) is found in fractions 33–42.

Proton NMR (CDCl$_3$, TMS): δ 0.99 (m,9H); 3.53 (m,3H); 3.81 (m,3H); 3.88 (m,3H); 4.05 (m,1H); 4.55 (m,1H); 5.45 (m,1H); 6.48 (m,2H); 6.79 (m,1H); 7.25–7.50 (m)

Mass spec(FAB-High Res.): Theory for C$_{24}$H$_{31}$N$_2$O$_6$+H: 443.2182 Found: 443.2180

Preparation No. 58 Preparation of (4S,5R)-N-(t-butylaminocarbonyl)-2-(2,4-dimethoxyphenyl)-4-phenyl-5-oxazolidinecarboxylic acid potassium salt (6Ka) and its free acid (7Ka)

A 100 mg (0.23 mM) quantity the less polar isomer of (4S,5R)-N-(t-butylaminocarbonyl)-2-(2,4-dimethoxyphenyl)-4-phenyl-5-oxazolidinecarboxylic acid methyl ester (Preparation 57, 5Ka) is stirred at room temperature under nitrogen in 3 mL MeOH. To this is added 0.1 mL water and 43 mg (0.31 mM) potassium carbonate. After 1 hour, TLC shows no starting material left. Store in freezer overnight. The next morning the solvent is evaporated to give (4S,5R)-N-(t-butylaminocarbonyl)-2-(2,4-dimethoxyphenyl)-4-phenyl-5-oxazolidinecarboxylic acid potassium salt (6Ka).

Proton NMR (d$_6$-DMSO): δ 1.20 (s, 9H): 3.51 (s, 1H); 3,76 (s, 3H); 3.96 (s, 3H); 4.32 (d, 2H); 4.80 (s, 1 H); 5.29 (d, 1H); 6.60–6.68 (m, 2H); 6.71 (d, 1H); 7.26 (d, 1H); 7.35 (5, 1H); 7.45 (t, 2H); 7.53 (d, 2H).

Preparation No. 59 Preparation of (4S,5R)-N-(t-butylaminocarbonyl)-2-(2,4-dimethoxyphenyl)-4-phenyl-5-oxazolidinecarboxylic acid (7Ka)

(4S,5R)-N-(t-butylaminocarbonyl)-2-(2,4-dimethoxyphenyl)-4-phenyl-5-oxazolidinecarboxylic acid potassium salt (6Ka, Preparation 58) is partitioned between methylene chloride and water containing 0.9 mL 1N HCl. The layers are separated and the aqueous layer reextracted with methylene chloride. The organic layers are combined, dried over sodium sulfate and evaporated. This leaves (4S, 5R)-N-(t-butylaminocarbonyl)-2-(2,4-dimethoxyphenyl)-4-phenyl-5-oxazolidinecarboxylic acid (7Ka) as a white solid.

Preparation No. 60: Preparation of 7-TES-baccatin III-13-(4S,5R)-N-(t-butylaminocarbonyl)-2-(2,4-dimethoxyphenyl)-4-phenyl-5-oxazolidinecarboxylic acid ester (9KaA)

(4S,5R)-N-(t-butylaminocarbonyl)-2-(2,4-dimethoxyphenyl)-4-phenyl-5-oxazolidinecarboxylic acid (1.07 mM, Preparation 59, 7Ka) is dissolved in 1.5 mL methylene chloride-3 mL toluene. To this is added 7-TES-baccatin III (500 mg, 0.71 mM, 8A), DMAP (45 mg, 0.36 mM) and DCC (240 mg, 1.15 mM). The reaction is stirred under nitrogen for one hour at RT. The resultant urea side product is removed by filtation and the filtrate is evaporated under vacuum. The residue is chromatographed over silica gel (80 g), eluting with 25-75 EtOAc-hexane (200 mL) and 33–67 EtOAc-hexane (1 L). Fractions of 20 mL are collected, analyzing them by TLC. Fractions 28–47 contain the desired product and are combined and evaporated, 7-TES -baccatin III-13-(4S,5R)-N-(t-butylaminocarbonyl)-2-(2,4-dimethoxyphenyl)-4-phenyl-5-oxazolidinecarboxylic acid ester (9KaA) is obtained as a white solid.

Mass Spec (FAB, M+H): Calc'd for C$_{60}$H$_{79}$N$_2$O$_{16}$Si 1111.5198: Found 1111.5189.

Preparation No. 61: Preparation of 13-(N-(t-butylaminocarbonyl)-β-phenyl isoserinyl)-baccatin III; N-debenzoyl-N-(t-butyl)aminocarbonyl-taxol; 13-β-phenyl-isoserinyl)-baccatin III N-t-butyl urea (10KA)

A 0.1 M HCl solution is prepared from 0.071 mL acetyl chloride and 9.929 mL of MeOH, leaving it sit for 30 minutes before using.

7-TES -baccatin III-13-(4S,5R)-N-(t-butylaminocarbonyl)-2-(2,4-dimethoxyphenyl)-4-phenyl-5-oxazolidinecarboxylic acid ester (100 mg, Preparation 60, 9KaA) is treated with the above methanolic HCl solution (0.5 mL) with stirring under nitrogen. The reaction is complete after 45 minutes as shown by TLC. The reaction mixture is partitioned between ethyl acetate-5% sodium bicarbonate. The layers are separated and the aqueous layer reextracted with ethyl acetate. The organic layers are combined, dried over sodium sulfate and evaporated under vacuum.

The crude product is chromatographed over silica gel(8 g), eluting with 33-67 acetone-hexane (70 mL) and 40-60 acetone-hexane (35 mL). Fractions of 2 mL are collected, analyzing them by TLC. Pure product is found in fractions 18–29, which which are combined and evaporated, 13-(N-(t-butylaminocarbonyl)-β-phenyl isoserinyl)-baccatin III (10KA) is obtained as a white solid. The physical data correspond to those obtained previously in Preparation No. 46.

Preparation 1A 2'-[{(2,2,2-Trichloroethyl)oxy}carbonyl]-taxol, 7-Methylxanthate

Methyl iodide (1.3 equivalents) is added to a stirred solution of 2'-[{(2,2,2-trichloroethyl)-oxy}carbonyl]taxol (1 equivalent) in carbon disulfide. Sodium hydride (2.1 equivalents) is added and the resulting mixture is stirred and checked by tlc for formation of the methyl xanthate. When reaction is complete, the excess carbon disulfide and methyl iodide are removed by evaporation. The residue is partitioned between water and ether, the layers are separated, the organic layer is dried, filtered, and concentrated to give the title compound.

Preparation 2A 2'-[{(2,2,2-Trichloroethyl)oxy}carbonyl]taxol. 7-Methanesulfonate Methanesulfonyl chloride (1.2 equivalents) is added dropwise to a solution of 2'-[{(2,2,2-trichloroethyl)oxy}carbonyl]taxol (1 equivalent) and pyridine (5 equivalents) in $CH_2Cl_2$ which is stirred at ice-bath temperature. The reaction mixture is allowed to warm and stirring is continued until tlc evidence indicates that reaction is complete. The reaction mixture is quenched with ice water and is extracted with $CH_2Cl_2$ and these extracts are washed successively with dilute aqueous acid, dilute aqueous $NaHCO_3$, and water and then are dried, filtered, and concentrated to give the crude reaction product. Chromatography of the crude product over silica gel gives pure title compound.

Preparation 3A 2'-[{(2,2,2-Trichloroethyl)oxy}carbonyl]taxol, 7-Trifluoromethylsulfonate Trifluoromethanesulfonic anhydride (1.3 equivalents) is added dropwise to a solution of 2'-[{(2,2,2-trichloroethyl)oxy}carbonyl]taxol (1 equivalent) in pyridine which is stirred and cooled to −30° C. The reaction mixture is allowed to warm and stirring is continued until tlc evidence indicates the reaction is complete. The reaction solution is quenched with ice water and is extracted with $CH_2Cl_2$. The $CH_2Cl_2$ extracts are washed successively with cold, dilute aqueous acid, dilute aqueous $NaHCO_3$, and water and then are dried, filtered, and concentrated to give the crude reaction product. Chromatography of the crude product over silica gel gives pure title compound.

Preparation 4A 2'-[{(2,2,2-Trichloroethyl)oxy}carbonyl]-7-deoxy-7-azidotaxol

A solution of 2'-[{(2,2,2-trichloroethyl)oxy}carbonyl]-taxol, 7-trifluoromethylsulfonate (1 equivalent) and 18-crown-6 (1 equivalent) N,N-dimethylpropylene urea is stirred with potassium azide (10 equivalents). The mixture is stirred and warmed until tlc evidence indicates the reaction is complete. The reaction mixture is quenched with cold water and the resulting solution is extracted with ether. The ether extract is washed thoroughly with water, dried, filtered, and concentrated to give the crude reaction product. Chromatography of the crude product over silica gel gives pure title compound.

Preparation 5A 2'-[{(2,2,2-Trichloroethyl)oxy}carbonyl]-7-deoxy-7-aminotaxol

A solution of 2'-[{(2,2,2-trichloroethyl)oxy}carbonyl]-7-deoxy-7-azidotaxol in ethanol is stirred with 10% palladium-on-carbon catalyst in a hydrogen atmosphere. Following reaction. the catalyst is removed by filtration and the filtrate is concentrated to give the crude reaction product. Chromatography of the crude product over silica gel gives pure title compound.

Preparation 6A Preparation of N-Desbenzoyl-N-benzyloxycarbonyl-2'-{[(2,2,2-trichloroethyl)oxy]carbonyl}-taxol, (({2aR-[2aα,4β,4aβ,6β,9α,(αR*,βS*), 11α,12α,12aα,12bα]}-β-(Benzyloxycarbonylamino)-α-{[(2,2,2-trichloroethoxy)-carbonyl]oxy}benzenepropionic Acid, 6,12b-Bis(acetyloxy)-12-(benzoyloxy)-2a,3,4,4a,5,6, 9,10,11,12,12a,12b-dodecahydro-4,11-dihydroxy-4a,8,13, 13-tetramethyl-5-oxo-7,11-methano-1H-cyclodeca[3,4] benz[1,2-b]-oxet-9-yl Ester)) (12BA); and N-Desbenzoyl-N-benzyloxycarbonyl-2',7-bis{[(2,2,2-trichloroethyl)oxy]carbonyl}-taxol, (({2aR-[2aα,4β,4aβ,6β, 9α,(αR*,βS*),11α,-12α,12aα,12bα]}-β-(Benzyloxycarbonylamino)-α-[{(2,2,2-trichloroethoxy)-carbonyl}oxy]benzenepropanoic acid, 6,12b-Bis(acetyloxy)-4-{[(trichloroethoxy)carbonyl]oxy}-2a,3,4,4a,5,6,9,10,11,12,12a,12b-dodecahydro-11-hydroxy-4a,8,13,13-tetramethyl-5-oxo-7, 11-methano-1H-cyclodeca[3,4]benz[1,2-b]-oxet-9-yl Ester)).

The procedure described for the preparation of 2'-troc-taxol [Magri et al., J. Org. Chem., 1986, 51, 797] is followed, using N-desbenzoyl-N-benzyloxycarbonyltaxol (0.290 g, 0.328 mmol) and 2,2,2-trichloroethyl chloroformate (59 μL, 0.091 g, 0.43 mmol) in $CH_2Cl_2$ (11 mL) containing pyridine (1.6 mL). Following workup, the crude product (0.340 g) is chromatographed over silica gel (40–63 μm, Merck size B column) using a $CH_2Cl_2$ solution for application of the material to the column and 40% EtOAc-hexane (90 fractions), 60% EtOAc-hexane (30 fractions), and EtOAc to elute the column (8 mL fractions are collected). N-Desbenzoyl-N-benzyloxycarbonyl-2',7-bistroc-taxol (0.053 g, 13%) is eluted in fractions 14–23. Starting material (0.014 g, 5%) is recovered in fractions 139–143. The desired N-desbenzoyl-N-benzyloxycarbonyl-2'-troc-taxol 12BA (0.248 g, 0.234 mmol, 71%) is eluted in fractions 49–80 and is characterized by the following spectral data:

$^1$H NMR (CDCl$_3$, TMS) δ 8.15 (d, 2H, aromatic), 7.62 (t, 1H, aromatic), 7.52 (t, 2H, aromatic), 7.30–7.50 (m, 5H, aromatic), 7.17 (m, 2H, aromatic), 6.26 (m, 1H, H$_{13}$), 6.25 (s, 1H, H$_{10}$), 5.71 (m, 1H, —NH—), 5.67 (d, 1H, H$_2$), 5.58 (m, 1H, H$_3$), 5.41 (d, 1H, H$_{2'}$), 5.08 (d, 1H, PhCH$_a$HO—), 4.96 (d, 1H, PhCH$_b$O—), 4.94 (m, 1H, H$_5$), 4.79 (d, 1H, —OCH$_a$HCCl$_3$), 4.68 (d, 1H, J=11.8 Hz, —OCH$_b$CCl$_3$), 4.42 (m, 1H, H$_7$), 4.31 (d, 1H, H$_{20a}$), 4.18 (d, 1H, H$_{20b}$), 3.78 (d, 1H, H$_3$), 2.55 (m, 1H, H$_{6a}$), 2.47 (m, 1H, H$_{14a}$), 2.45 (s, 3H, —CH$_3$), 2.31 (m, 1H, H$_{14b}$), 2.24 (s, 3H, —CH$_3$), 1.92 (m,1H, H$_{6b}$), 1.86 (s, 3H, —CH$_3$), 1.68 (s, 3H, —CH$_3$), 1.23 (s, 3H, —CH$_3$), 1.14 (s, 3H, —CH$_3$); mass spectrum 1058, 569, 551, 509, 105, 91 m/z.

Preparation 7A 10-Deacetyltaxol

A solution of taxol (0.026 g, 0.030 mmol) and 98% hydrazine (0.035 g, 1.1 mmol) in 95% ethanol (1.0 mL) is stirred at room temperature for 2 hr. The solution is poured into water and ether, the mixture is shaken well, and the layers separated. The aqueous layer is extracted with additional ether. The combined ether extracts are dried over Na$_2$SO$_4$, filtered and concentrated, giving 0.021 g of the title compound: $^1$H NMR spectrum in CDCl$_3$ is identical to the spectrum reported for 10-deacetyltaxol (Ringel, I.; Horwitz, S. B. *J. Pharmacol. Exp. Ther.* 1987, 242, 692) and is identical to the spectrum of an authentic sample.

Preparation 8A 10-Deacetylbaccatin III

A solution of baccatin III (0.024 g, 0.041 mmol) in 95% ethanol (1.0 mL) is prepared by warming the mixture. The solution is cooled to room temperature, 98% hydrazine (0.035 g, 1.1 mmol) is added and the solution is stirred at room temperature for 24 hr. The solution is poured into water/ether, shaken well, and the layers are separated. The ether layer is washed with water, dried (Na$_2$SO$_4$), filtered, and concentrated, giving 0.010 g of the title compound: $^1$H NMR spectrum in CDCl$_3$ (sparingly soluble) is identical to that of an authentic sample of 10-deacetylbaccatin III.

Preparation 10A N-Debenzoyl-N-{[(2,2,2-trichloroethyl)oxy]-carbonyl-2'-triethyl-silyltaxol N-Debenzoyl-N-{[(2,2,2-trichloroethyl)oxy]carbonyl}taxol ((13-[N-(2,2,2-trichloro-ethoxycarbonyl)-β-phenyl-isoserinyl]-baccatin III; 10DA, Preparation 28)) is selectively silylated by reaction with triethylsilyl chloride in pyridine containing a catalytic amount of 4-dimethylaminopyridine. The reaction is quenched by pouring into ice water and extracting with CH$_2$Cl$_2$. The extract is dried, filtered, concentrated and the crude product is purified by silica gel chromatography, giving the pure title compound.

Preparation 13A N-Debenzoyl-N-(t-butyl)oxycarbonyl-2'-{[(2,2,2-trichloromethyl)-oxy]carbonyl}-taxol A (Compound 12DA); (({2aR[2aα,4β,4aβ,6β,9α,(αR*,βS*)-,11α,12α,12aα,12bα]}-β-[(t-Butyl)oxycarbonylamino]-α-{[(2,2,2-trichloroethoxy)carbonyl]oxy}benzenepropionic Acid, 6,12b-Bis(acetyloxy)-12-(benzoyloxy)-2a,3,4,4a,5,6,9,-10,11,12,12a,12b-dodecahydro-4,11-dihydroxy-4a,8,13,13-tetramethyl-5-oxo-7,11-methane-1H-cyclodeca[3,4]benz[1,2-b]-oxet-9-yl Ester)); and N-Debenzoyl-N-(t-butyl)oxycarbonyl-2',7-bis{[(2,2,2-trichloro-ethyl)oxy]carbonyl}-taxol ((({2aR-[2aα,4β,4aβ,6β,9α,(αR*,βS*),11α,12α,12aα,12bα]}-β-[(t-Butyl)oxycarbonylamino]-α-[{(2,2,2-trichloroethoxy)carbonyl}oxy]benzenepropanoic acid, 6,12b-Bis(acetyloxy)-12-(benzoyloxy)-4-{[(trichloroethoxy)carbonyl]oxy}-2a,3,4,4a5,6,9,10,11,12,12a,12b-dodecahydro-11-hydroxy-4a,8,13,13-tetramethyl-5-oxo-7,11-methano-1H-cyclodeca[3,4]benz[1,2-b]oxet-9-yl Ester)).

Following the procedure for the preparation of 2'-troc-taxol (Magri et al., J. Org. Chem. 1986, 51, 797), but starting with N-debenzoyl-N-(t-butyl)oxycarbonyltaxol (Compound 10BA; 1.98 g. 2.33 mmol) and 2,2,2-trichloroethyl chloroformate (405 μL, 0.622 g, 2.94 mmol) in CH$_2$Cl$_2$ (80 mL) the product 12DA is prepared. Following workup, the crude product is chromatographed over silica gel (40–63 μm, 37×350 mm, 190 g) using a CH$_2$Cl$_2$ solution for application of the material to the column and 40% EtOAc-hexane (63 fractions) followed by 75% EtOAc-hexane to elute the column (45 mL fractions are collected). N-Debenzoyl-N-(t-butyl)oxycarbonyl-2',7-bistroc-taxol (0.140 g) is eluted in fraction 6. Starting material (0.192 g) is recovered in fractions 70–78. The desired N-debenzoyl-N-(t-butyl)oxycarbonyl-2'-troc-taxol (Compound 12DA) is eluted in fractions 18–38 and characterized by the following spectral data:

$^1$H NMR (CDCl$_3$, TMS) δ 8.12 (d, 2H, J=8.1 Hz), 7.62 (t, 1H, J=7.2 Hz), 7.51 (t, 2H, J=7.7 Hz), 7.30–7.44 (m, 5H), 6.30 (s, 1H, H$_{10}$) 6.30 (t, 1H, H$_{13}$), 5.68 (d, 1H, J=7.1 Hz, H$_2$), 5.48 (d, 1H, —NH— or H$_3$'), 5.44 (d, 1H, H$_3$' or —NH—), 5.36 (d, 1H, J=2.2 Hz, H$_2$'), 4.98 (d, 1H, J=9.3 Hz, H$_5$), 4.79 (d, 2H, J=11.9 Hz, 2'-troc-H$_a$), 4.70 (d, 2H, J=11.8 Hz, 2'-troc-H$_b$), 4.44 (m, 1H, H$_7$), 4.32 (d, 1H, J=8.4 Hz, H$_{20a}$), 4.18 (d, 1H, J=8.4 Hz, H$_{20b}$), 3.82 (d, 1H, J=6.8 Hz, H$_3$)

Preparation 14A 2'-Triethylsilyl-taxol, 7-methylxanthate

A 500 mg (0.52 mM) quantity of 2'-Triethylsilyl-taxol is dissolved in 5 mL of distilled THF. To the solution is added 50 μL (0.80 mM) methyl iodide and 155 μL (2.58 mM) carbon disulfide. A slurry of 40 mg (60% sodium hydride in oil) in distilled THF is made and approximately half added and the resulting mixture stirred and checked by tlc for formation of the methyl xanthate. After 0.5 hours the residue is partitioned between saturated NH$^4$Cl solution and EtOAc, the layers are separated, the organic layer is filtered through Na$_2$SO$_4$, and concentrated to give the title compound. The product is purified by column chromatography using 60 gm of silica gel in 1:4 EtOAc:hexane. The product is added using methylene chloride and the column eluted with 400 mL 1:4 400 mL 1:3 EtOAc:hexane, and 300 mL 1:2 EtOAc:hexane. The fractions containing product are found by TLC and are combined and evaporated giving the 2'-triethylsilyl-taxol, 7-methylxanthate as a white solid.

TLC: silica gel 60; 33% EtOAc-67% hexane; R$_f$: 0.40.

NMR (CDCl$_3$, TMS): δ 0.44 (m, 6H); 0.81 (m); 1.19 (s, 3H); 1.22 (s,3H); 2.16 (s, 3H); 2.48 (s, 3H); 2.58 (s, 3H); 2.94 (m, 1H); 4.03 (d, 1H); 4.25 (d, 1H); 4.37 (d, 1H); 4.70 (s, 1H); 5.00 (d, 1H); 5.73 (m,2H); 6.28 (m, 1H); 6.32 (s, 1H); 6.40 (m, 1H); 7.11 (d, 1H); 7.30–7.65 (m); 7.75 (d,2H); 8.15 (d, 2H).

Preparation 15A 2'-TES-Taxol 7-Triflate

A solution of 2'-triethylsilyltaxol [0.10 g; Chaudhary et al., *J. Org. Chem.* 1993, 58, 3798] and dry pyridine (0.29 mL) in CH$_2$Cl$_2$ (4 mL) is cooled to −20° C. and triflic anhydride (0.17 mL) is added. The solution is stirred and allowed to warm to about −10° C. After 3 hours, saturated NH$_4$Cl is added to the reaction and the mixture is extracted with EtOAc. The organic extract solution is washed with dilute aqueous NaHSO$_4$, with saturated NaHCO$_3$, is dried over Na$_2$SO$_4$, filtered and concentrated at room temperature. The crude reaction product is chromatograhed over silica gel (flash) using 30% EtOAc in hexane to elute the column and collecting fractions of 5 mL volume. The fractions (4–10) containing the desired product are combined and give the title compound (0.094 g).

Preparation 16A Baccatin III 7-O-triflate (24)

A solution of baccatin III (5.25 g, 8.93 mmoles) in CH$_2$Cl$_2$ (21 mL) and pyridine (18.1 mL) is cooled in a −30° C. bath. Trifluoromethanesulfonic anhydride (3.76 mL, 6.31 g, 22.3 mmoles) is added and the resulting mixture stirred and allowed to warm to room temperature over a period of an hour. The reaction is complete after 4 hrs; saturated aq NH$_4$Cl (50 mL) is added and the mixture extracted with CH$_2$Cl$_2$. The organic extract is washed successively with 1 M aq NaHSO$_4$ (50 mL), saturated aq NaHCO$_3$ (2×50 mL), saturated aq NaCl, and dried (Na$_2$SO$_4$), filtered, and concentrated under reduced pressure. Care is taken not to warm the solution greater than 40° C. during removal of the solvent. A pale yellow solid is obtained and which is flash chromatographed over silica gel (6" silica gel in a 75 mm column, 125 mL fractions). The material is applied to the column in a CH$_2$Cl$_2$ solution and the column eluted with 5% CH$_3$CN—CH$_2$Cl$_2$. Fractions 19–35 contain the desired baccatin-III-7-O-triflate (4.837 g, 6.71 mmoles, 75%) which is a white solid.

$^1$H NMR (CDCl$_3$, TMS) δ 8.10 (d, 2H, J=7.2 Hz), 7.63 (t, 1H, J=7.4 Hz), 7.49 (t, 2H, J=7.6 Hz), 6.63 (s, 1H, H$_{10}$), 5.68 (d, 1H, J=7.0 Hz, H$_2$), 5.52 (dd, 1H, J=7.5, 10.1 Hz, H$_7$), 4.94 (d, 1H, J=8.4 Hz, H$_5$), 4.86 (m, 1H, H$_{13}$), 4.35 (d, 1H, J=8.4 Hz, H$_{20a}$), 4.15 (d, 1H, J=8.4 Hz, H$_{20b}$), 4.01 (d, 1H, J=7.0 Hz, H$_3$), 2.87 (5 lines, H$_{14a}$) 2.30 (s, 3H, —CH$_3$), 2.20 (s, 3H, —CH$_3$), 2.10–2.30 (m, H$_{6a}$, H$_{6b}$, H$_{14b}$), 1.87 (s, 3H, —CH$_3$), 1.59 (s, 3H, —CH$_3$), 1.19 (s, 3H, —CH$_3$), 1.05 (s, 3H, —CH$_3$).

Preparation 18A 7-Deoxy-7β,8β-methano-baccatin III (26)

A solution of 7-trifluoromethanesulfonyl-baccatin III (24, 87 mg, 0.12 mM) in distilled dioxane (1.5 mL) is treated with an aqueous sodium azide solution (0.10 g, 1.5 mM NaN$_3$ in 0.30 mL water.) The reaction is refluxed under nitrogen one hour. The mixture is diluted with ethyl acetate and washed with water and brine, dried over andhydrous sodium sulfate, and evaporated. The product is purified by column chromatography on silica gel 60 in 25% ethyl acetate-methylene chloride giving a 56% yield (39 mg) of white crystalline 7-deoxy-7β,8β-methano-baccatin III.

NMR (CDCl$_3$, TMS): δ 1.10 (s, 3H); 1.22 (s, 3H); 1.35 (m, 1H); 1.64 (m, 1H); 1.78 (s, 1H); 2.03 (s+m, 4H); 2.21 (s, 3H); 2.26 (s, 3H); 2.20–2.55 (m, 5H); 4.04 (d, 1H, J=8.5 Hz); 4.18 (d, 1H, J=7.5 Hz); 4.30 (d, 1H, J=8.5 Hz); 4.74 (d, 1H); 4.83 (m, 1H); 5.63 (d, 1H, J=7.5 Hz); 6.35 (s, 1H); 7.49 (m, 2H); 7.62 (m, 1H); 8.13 (m, 2H). $^{13}$C-NMR (CDCl$_3$, TMS): 15.15, 15.28, 20.43, 20.82, 21.99, 25.90, 26.35, 31.63, 35.19, 38.57, 38.76, 42.20, 67.51, 75.30, 76.20, 76.49, 79.23, 79.91, 84.73, 128.50, 129.33, 129.99, 132.59, 133.54, 144.19, 167.20, 169.63, 170.00, 202.08.

Preparation 19A 7-deoxy-7α-azido-baccatin III (27)

A mixture of 7-trifluoromethanesulfonyl-baccatin III (24, 102 mg, 0.14 mM), sodium azide (13 mg, 0.20 mM), and 18-crown-6 (32 mg, 0.12 mM) in 1,3-dimethyl-3,4,5,6-tetrahydro-2(1H)-pyrimidinone (1.0 mL) is stirred at room temperature overnight under an inert atmosphere. The reaction is partitioned between ethyl acetate and water. The organic layer is dried over anhydrous sodium sulfate and evaporated. The crude product is purified by column chromatography on silica gel 60 in 15% ethyl acetate-methylene chloride. The product is further purified by crystallization from methylene chloride-hexane giving 37 mg of 7-deoxy-7α-azido-baccatin III.

NMR (DMSO-d$_6$, TMS): δ 0.96 (s, 6H); 1.59 (s, 3H); 1.91(s, 3H); 2.13 (s, 3H); 2.25 (s, 3H); 2.10–2.35 (m, 4 H); 2.47 (m, 1H); 3.80 (m, 2H); 4.07 (d, 1H, J=8.0 Hz); 4.33 (d, 1H, J=8.0 Hz); 4.60 (s+m, 2H); 4.99 (dd, 1H); 5.35 (d, 1H); 5.48 (d, 1H, J=7.2 Hz); 6.79 (s, 1H); 7.59 (m, 2H); 7.69 (m, 1H); 8.05 (m, 2H). $^{13}$C-NMR (DMSO-d$_6$, TMS): 15.40, 17.31, 20.67, 22.20, 25.93, 29.81, 39.22, 40.63, 41.73, 55.57, 64.28, 65.91, 75.33, 76.91, 77.33, 78.22, 80.44, 80.94, 128.77. 129.58, 129.98, 130.28, 133.33, 145.43, 165.30. 168.75, 169.09, 207.11.

The following Examples further illustrate the subject invention

EXAMPLE 1

Preparation of:

2'-{[(2,2,2-Trichloroethyl)-oxy]carbonyl}-7-deoxy-7-fluorotaxol (Compound 13AA;IIIa), (({2aR[2aα,4aβ,6β,9α,(αR*,βS*),11α,12α,-12aα,12bα]}-β-(Benzoylamino)-α-{[(2,2,2-trichloroethoxy)carbonyl]-oxy}benzenepropanoic acid, 6,12b-Bis(acetyloxy)-12-(benzoyloxy)-2a,3,4,4a,5,6, 9,10,11,-12,12a,12b-dodecahydro-4-fluoro-11-hydroxy-4a,8,13,13-tetramethyl-5-oxo-7,11-methano-1H-cyclodeca[3,4]benz[1,2-b]-oxet-9-yl Ester)); and 2'-{[(2,2,2-Trichloroethyl)oxy]carbonyl}-7-deoxy-7β,8β-methanotaxol (Compound 14AA), (({2aR-[2aα,4β,4aβ,6β,9α,(αR*,βS*),11α,12α,-12aα,12bα]}-β-(Benzoylamino)-α-{[(2,2,2-trichloroethoxy)-carbonyl]oxy}benzenepropanoic acid, 6,12b-Bis(acetyloxy)-12-(benzoyloxy)-2a,3,4,4a,5,6,9-,10,11,12,12a,12b-dodecahydro-11-hydroxy-8,13,13-trimethyl-5-oxo4,4a;7,11-bismethano-1H-cyclodeca[3,4]benz[1,2-b]-oxet-9-yl Ester))

Dimethylaminosulfur trifluoride (methylDAST) (250 μL, 0.340 g, 2.56 mmole) is added at once by syringe to a stirred and cooled (acetone-Dry Ice bath) solution of 2'-{[(2,2,2-trichloro-ethyl)oxy]carbonyl}taxol 12AA [Magri, N. F.; Kingston, D. G. I. *J. Org. Chem.*, 1986, 51, 797] (1.60 g, 1.55 mmole) in CH$_2$Cl$_2$ (180 mL). The cooling bath is removed and the reaction container is allowed to come to room temperature. The reaction is stirred and starting material is found to be completely consumed within 70 minutes judging from tlc evidence. The reaction is quenched by the addition of water and transferred to a separatory funnel with the aid of additional CH$_2$Cl$_2$. The layers are separated and the organic layer is washed once with water, dried (Na$_2$SO$_4$), filtered, and concentrated to give a white solid (1.65 g). The residue is chromatographed over silica gel (40–63 μm, 195 g in a 3.7×35 cm column; 40 mL fractions) using a CH$_2$Cl$_2$ solution for application on the column and 25% acetone in hexane for elution of the column.

Fractions 32–39 contain a mixture of at least two compounds.

Fractions 40–42 contain a mixture which may include some of compound 14AA.

Fractions 43–49 (0.391 g) contain primarily compound 14AA (R$_f$=0.22 in 30% acetone-hexane) together with two minor components.

Fractions 50–54 contain 0.162 g of a mixture of 14AA and 13AA. This mixture is rechromatographed over silica gel (Merck Lobar® size B column, 8 mL fractions) using CH$_2$Cl$_2$ for application to the column and 25% acetone-hexane for elution of the column. Fractions 58–70 contain 0.056 g of 14AA, which is combined (pool A) with the aforementioned 0.391 g from fractions 43–49 (total, 0.447 g), and fractions 76–92 contain 0.053 g of 13AA.

One of the two minor components of pool A is separated and is obtained as a pure compound by rechromatography of the mixture over silica gel (two Merck Lobar® size B columns, 9 mL fractions). The mixture is applied to the column in CH$_2$Cl$_2$ and the column is eluted with 25% EtOAc-hexane through fraction 72, 30% EtOAc-hexane through fraction 180, and with 40% EtOAc-hexane thereafter.

Fractions 195–215 (0.373 g) contain 14AA and the second minor component which is not separated until after removal of the troc protecting groups. Despite the presence of the minor component, compound 14AA forms beautiful crystals upon slow evaporation of the solvent and the following spectral data are recorded:

FAB mass spectrum gives peaks at 1012, 1010, 551, 533, 511, 491, 460, and 442 mass units;

$^1$H NMR (CDCl$_3$, TMS) δ 8.19 (d, 2H, J=7.1 Hz), 7.71 (d, 2H, J=7.2 Hz), 7.59 (t, 1H), 7.48 (m), 7.36 (m), 6.98 (d, 1H, —NH—), 6.57 (s, 1H, H$_{10}$), 6.28 (t, 1H, J=8.7 Hz, H$_{13}$), 6.08 (dd, 1H, J=9.5, 2.7 Hz, H$_3$'), 5.67 (d, 1H, J=7.6 Hz, H$_2$), 5.54 (d, 1H, J=2.8 Hz, H$_2$'), 4.77 (dd, 2H, 2'-troc —CH$_2$—), 4.74 (1H, H$_5$), 4.32 (d, 1H, J=8.6 Hz, H$_{20a}$), 4.09 (d, 1H, J=8.6 Hz, H$_{20b}$), 4.07 (1H, H$_3$), 2.47 (s, 3H, —CH$_3$), 2.23 (dd, 1H, J$_{H-7}$=9.9 Hz, J$_{H-19a}$=5.3 Hz, H$_{19b}$), 2.19 (s, 3H, —CH$_3$), 1.90 (d, 3H, J=1.3 Hz, —CH$_3$), 1.67 (dd, 1H, J$_{H-7}$=7.2, J$_{H-19a}$32 5.3 Hz, H$_{19b}$), 1.38 (m, 1H, H$_7$), 1.26 (s, 3H, —CH$_3$), and 1.21 (s, 3H, —CH$_3$); $^{13}$C NMR (CDCl$_3$, TMS) 201.88, 169.64, 169.59, 167.45, 167.03, 166.96, 153.24, 140.41, 136.43, 133.89, 133.61, 133.36, 132.05, 130.31, 129.25, 129.15, 129.07, 128.95, 128.75, 128.68, 128.59, 127.17, 126.49, 93.82, 84.83, 80.11, 79.56, 79.47, 77.78, 77.23, 75.66. 75.41, 72.17, 52.58, 42.85, 38.57. 35.93, 35.04, 32.26. 26.05, 22.30, 21.60, 20.83, 15.82. 14.56 ppm.

Fractions 55–65 (0.480 g) contain pure compound 13AA and when taken with the 13AA obtained from the above rechromatography of mixed fractions, give 13AA as a colorless crystalline solid:

$R_f$=0.19 in 30% acetone-hexane;

FAB mass spectrum gives peaks at 1034, 1032, 1030, 571, 511, 460, 442, 210, and 105 mass units;

$^1$H NMR (CDCl$_3$, TMS) δ8.18 (dd, 2H, J=7.0,1.5 Hz), 7.76 (dd, 2H, J=7.0, 1.5 Hz), 7.62 (t, 1H), 7.50 (m), 7.43 (m), 6.95 (d, 1H, —NH—), 6.57 (s, 1H, H$_{10}$), 6.27 (t, 1H, H$_{13}$), 6.08 (dd, 1H, J=9.5, 2.6 Hz, H$_3$), 5.78 (d, 1H, J=7.3 Hz, H$_2$), 5.55 (d, 1H, J=2.7 Hz, H$_2$), 5.05 (d, 1H, J=7.5 Hz, H$_5$), 4.78 (d, 1H, J=11.8 Hz, H$_{20a}$), 4.74 (d, 1H, J=11.8 Hz, H$_{20b}$), 4.48 (dd, 1H, J$_F$=48 Hz, H$_7$), 4.40 (d, 1H, J=8.4 Hz, H$_{20a}$), 4.31 (d, 1H, J=8.2 Hz, H$_{20b}$), 4.04 (d, 1H, 7.2 Hz, H$_3$), 2.63–2.45 (m), 2.49 (s, 3H), 2.27–2.10 (m), 2.20 (s, 3H), 1.91 (s, 3H), 1.74 (s, 3H), 1.20 (s, 3H), and 1.17 (s, 3H); $^{13}$C NMR (CDCl$_3$, TMS) 206.0, 169.9, 168.8, 167.2, 167.17, 153.2, 140.9, 136.4, 133.7, 133.5, 132.1. 130.3, 129.3, 129.2, 128.8, 128.7, 128.6, 127.2, 126.5, 96.2, 93.9, 81.9, 80.8, 78.8. 77.9, 77.8, 77.4, 77.2, 75.0, 72.1, 56.8 (d, J=18 Hz), 52.7, 42.7, 40.1, 35.7, 33.9, 33.6, 25.8, 22.6, 21.3, 20.8, 14.6, 14.4 ppm.

EXAMPLE 3

Preparation of:

N-Desbenzoyl-N-benzyloxycarbonyl-2'-{[(2,2,2-trichloroethyl)oxy]carbonyl}-7-deoxy-7-fluorotaxol (13BA), (({2aR-[2aα,4a,β,6β,9α,-(αR*,βS*),11α, 12α, 12aα,12bα]}-β-(Benzyloxycarbonylamino)-α-{[(2,2,2-trichloroethoxy)-carbonyl]oxy}benzenepropanoic acid, 6,12b-Bis(acetyloxy)-12-(benzoyloxy)-2a,3,4,4a,5,6,9,-10, 11,12,12a,12b-dodecahydro-4-fluoro-11-hydroxy-4a,8,13, 13-tetramethyl-5-oxo-7,11-methano-1H-cyclodeca[3,4]benz[1,2-b]-oxet-9-yl Ester)); and N-Desbenzoyl-N-benzyloxycarbonyl-2'-{[(2,2,2-trichloroethyl)oxy]carbonyl}-7-deoxy-7β,8β-methanotaxol (14BA), (({2aR-[2aα,4β,4aβ,6β, 9α(αR*,βS*)-11α,12α, 12aα,12bα]}-β-(Benzyloxy-carbonylamino)-α-{[(2,2,2-trichloroethoxy)carbonyl]oxy}benzenepropanoic acid, 6,12b-Bis(acetyloxy)-12-(benzoyloxy)-2a,3,4,4a,5,6,9,10, 11,-12,12a,12b-dodecahydro-11-hydroxy-8,13,13-trimethyl-5-oxo-4,4a;7,11-bismethano-1H-cyclodeca[3,4]benz[1,2-b]-oxet-9-yl Ester});

The procedure described for the treatment of 2'-troc-taxol with methylDAST is followed (Example 1), using N-desbenzoyl-N-benzyloxycarbonyl-2'-troc-taxol (12BA, Preparation 6A; 0.223 g, 0.21 mmol) and dimethylamino-sulfur trifluoride (methylDAST, 49 μL, 0.066 g, 0.50 mmol total, added in two portions) in CH$_2$Cl$_2$ (20 mL) under N$_2$ at −78° C. Following workup, the crude reaction product mixture (0.211 g, white solid) is chromatographed over silica gel (40–63 μm, two Merck size B columns) using a CH$_2$Cl$_2$ solution for application of the material to the column and 25% acetone-hexane for elution of the column. Fractions of 8 mL volume are collected. Fractions 107–118 contain a mixture of two components (0.065 g) which are separated in a second chromatography as described below. Fractions 128–140 contain compound 13BA (0.081 g, 0.076 mmol, 36%) which is characterized by the following spectral data:

$^1$H NMR (CDCl$_3$, TMS) δ 8.16 (d, 2H, J=7.2 Hz, aromatic), 7.63 (t, 1H, J=7.5 Hz, aromatic), 7.53 (t, 2H, J=7.6 Hz, aromatic), 7.30–7.45 (m, 5H, aromatic), 7.24 (m, aromatic), 7.12–7.19 (m, 2H, aromatic), 6.56(s, 1H, H$_{10}$), 6.24(t, 1H, H$_{13}$), 5.74 (d, 1H, J=7.4 Hz, H$_2$), 5.74 (1H, —NH—), 5.62 (d, 1H, H$_3$), 5.44 (d, 1H, H$_2$), 5.09 (d, 1H, J=12.5 Hz, PhCH$_a$HO—), 5.03 (d, 1H, H$_5$), 4.97 (d, 1H, PhCHH$_b$O—), 4.77 (d, 1H, J=11.9 Hz, —OCH$_a$HCCl$_3$), 4.68 (d, 1H, J=11.9 Hz, —OCHH$_b$CCl$_3$), 4.56 (dd, 1H, J$_F$=50 Hz, H$_7$), 4.37 (d, 1H, H$_{20a}$), 4.30 (d, 1H, H$_{20b}$), 4.00 (d, 1H, J=7.3 Hz, H$_3$), 2.57 (m, 1H, H$_{6a}$), 2.46 (s, 3H, —CH$_3$), 2.40 (m, 1H, H$_{14a}$), 2.21 (s, 3H, —CH$_3$), 2.15 (m, 1H, H$_{14b}$), 1.89 (s, 3H, —CH$_3$), 1.85 (m, 1H, H$_{6b}$), 1.74 (s, 3H, CH$_3$), 1.19 (s, 3H, —CH$_3$), 1.16 (s, 3H, —CH$_3$); mass spectrum (FAB) 1060.2466, C$_{51}$H$_{53}$Cl$_3$FNO$_{16}$+H requires 1060.2492, 571, 553, 511, 472, 389, 347, 329, 105, 91 m/z.

Pooled fractions 107–118 (0.065 g) from the preceding column are rechromatographed over silica gel (40–63 μm, one Merck size B column) using CH$_2$Cl$_2$ for application to the column and 10% MeCN—CH$_2$Cl$_2$ for elution of the column. Fractions of 8 mL volume are collected.

Fractions 96–120 contain 0.043 g (0.041 mmol, 20%) of compound 14BA:

$^1$H NMR (CDCl$_3$, TMS) δ 8.17 (d, 2H, J=7.1 Hz, aromatic), 7.59 (t, 1H, aromatic), 7.52 (t, 2H, aromatic), 7.31–7.46 (m, 5H, aromatic), 7.24 (m, aromatic), 7.09 (m, 2H, aromatic), 6.32 (s, 1H, H$_{10}$), 6.28 (t, 1H, J=8.6 Hz, H$_{13}$), 5.75 (d, 1H, J=10.0 Hz, —NH—), 5.64 (d, 1H, J=7.8 Hz, H$_2$), 5.59 (d, 1H, H$_3$), 5.41 (d, 1H, J=2.6 Hz, H$_2$), 5.00 (d, 1H, J=12.5 Hz, ArCH$_a$HO—), 4.91 (d, 1H, J=12.6 Hz, ArCHH$_b$O—), 4.76 (d, 1H, J=9.8 Hz, —OCH$_a$CCl$_3$), 4.73 (d, 1H, H$_5$), 4.68 (d, 1H, J=9.9 Hz, —OCHH$_b$CCl$_3$), 4.30 (d, 1H, J=8.6 Hz, H$_{20a}$), 4.07 (d, 1H, H$_3$), 4.05 (d, 1H, H$_{20b}$), 2.50 (m, 1H, H$_{14a}$), 2.43 (s, 3H, —CH$_3$), 2.36 (m, 1H, H$_{6a}$), 2.24 (m, 1H, H$_{19a}$), 2.20 (s, 3H, —CH$_3$), 2.10 (d, 1H, J=16.1 Hz, H$_{14b}$), 1.88 (s, 3H, —CH$_3$), 1.66 (m, 1H, H$_{19b}$) 1.38 (m, 1H, H$_7$), 1.26 (s, 3H, —CH$_3$), 1.21 (s, 3H, —CH$_3$); mass spectrum (FAB) 1040.2416, C$_{51}$H$_{52}$Cl$_3$NO$_{16}$+H requires 1040.2430, 980, 962, 551, 491, 369, 105, 91 m/z.

EXAMPLE 10

Preparation of [2aR-{2aα,4aβ,6β,9α,(αR*,βS*),11α,12α, 12aα,12bα}]-β-(Benzoylamino)-α-[{(2,2,2-trichloroethoxy)carbonyl}oxy]benzenepropanoic acid, 6,12b-Bis(acetyloxy)-12-(benzoyloxy)-2a,3,4,4a,5,6,9,10, 11,12,12a,12b-dodecahydro-4-fluoro-11-hydroxy-4a,8,13, 13-tetramethyl-5-oxo-7,11-methano-1H-cyclodeca[3,4]benz[1,2-b]-oxet-9-yl Ester; 2'-[{(2,2,2-Trichloroethyl)oxy}carbonyl]-7-deoxy-7-fluorotaxol (Compound 13AA, IIIa)

A solution of 2'-[{(2,2,2-trichloroethyl)oxy}carbonyl] taxol [Magri, N. F.; Kingston, D. G. I. J. Org. Chem., 1986, 51, 797] (0.021 g, 0.020 mmole) in CH$_2$Cl$_2$ (1.5 mL) is added by syringe over a period of 5 min to a stirred and cooled (acetone-Dry Ice bath) solution of dimethylamino-sulfur trifluoride (DAST) (2 μL, 0.014 mmole) in CH$_2$Cl$_2$ (0.5 mL) contained in a 3 mL Reacti-vial®. The cooling bath is removed after 15 min and the reaction container is allowed to come to room temperature. The reaction is stirred and the solution is again cooled in an acetone-Dry Ice bath and more DAST (4 μl, 0.028 mmole) in CH$_2$Cl$_2$ is added to the reaction. The cooling bath is removed after 15 min. and after 90 min. the reaction solution is diluted with additional CH$_2$Cl$_2$ and then is washed with water. The layers are separated and the organic layer is dried (Na$_2$SO$_4$), filtered, and concentrated to give a residue (0.017 g). The residue is chromatographed over silica gel (40–63 μm, 60 g) using a CH$_2$Cl$_2$ solution for application on the column and 30% acetone in hexane for elution of the column to give the desired title product having a $R_f$=0.19 (30% acetone-hexane):

FAB mass spectrum gives peaks at 1034, 1032, 1030, 571, 511, 460, 442, 210, and 105 mass units;

$^1$H NMR (CDCl$_3$, TMS) δ 8.18 (dd, 2H), 7.76 (dd, 2H), 7.62 (t, 1H), 7.50 (m), 7.43 (m), 6.95 (d, 1H), 6.57 (s, 1H), 6.27 (t, 1H), 6.08 (dd, 1H), 5.78 (d, 1H), 5.55 (d, 1H), 5.05 (d, 1H), 4.78 and 4.76 (d, 2H), 4.66 (d, 0.5H), 4.50 (d, 0.5H), 4.40 (d, 1H), 4.31 (d, 1H), 4.04 (d, 1H), 2.63–2.45 (m), 2.49 (s, 3H), 2.27–2.10 (m), 2.20 (s, 3H), 1.91 (s, 3H), 1.74 (s, 3H), 1.20 (s, 3H), and 1.17 (s, 3H); $^{13}$C NMR (CDCl$_3$, TMS) 206.0, 169.9, 168.8, 167.2, 167.17, 153.2, 140.9, 136.4, 133.7, 133.5, 132.1, 130.3. 129.3. 129.2, 128.8, 128.7, 128.6, 127.2, 126.5, 96.2, 93.9, 81.9, 80.8, 78.8, 77.9, 77.8, 77.4, 77.2, 75.0, 72.1, 56.8 d, J=18 Hz), 52.7, 42.7, 40.1, 35.7. 33.9, 33.6. 25.8, 22.6, 21.3, 20.8, 14.6, 14.4 ppm.

EXAMPLE 11

Preparation of [2aR-{2aα,4aβ,6β,9α,(αR*,βS*),11α,12α,12aα,12bα}]-β-(Benzoylamino)-α-hydroxybenzenepropanoic Acid, 6,12b-Bis(acetyloxy)-12-(benzoyloxy)-2a,3,4,4a,5,6,9,10,11,12,12a,12b-dodecahydro-4-fluoro-11-hydroxy-4a,8,13,13-tetramethyl-5-oxo-7,11-methano-1H-cyclodeca[3,4]benz[1,2-b]-oxet-9-yl Ester; 7-Deoxy-7-fluorotaxol (Compound IIIb)

A solution of 2'-[{(2,2,2-trichloroethyl)oxy}carbonyl]-7-deoxy-7-fluorotaxol (Compound 13AA, IIIa; 0.010 g, 0.0097 mmole) in 9:1 methanol/acetic acid (1.0 mL) is stirred with activated zinc metal (0.012 g) at room temperature. After 90 min, the reaction is worked up by removal of the zinc by filtration and concentration of the filtrate under reduced pressure. The residue is dissolved in CH$_2$Cl$_2$ and this solution is washed with 0.1N aq. HCl, with 5% aq. NaHCO$_3$, and with water. The aqueous layer is back extracted with CH$_2$Cl$_2$ and the combined organic extracts are dried (Na$_2$SO$_4$), filtered, and concentrated to give a residue (0.009 g). The residue is chromatographed over silica gel (40–63 μm, 8 mm×250 mm column) and is applied to the column in a CH$_2$Cl$_2$ solution. The column is eluted with 60 mL of 20% EtOAc in hexane and then is eluted with 40% EtOAc in hexane. The desired product (Compound IIIb) is obtained as a solid:

FAB mass spectrum 856, 571, 511, 286, 268, 240, 210, 105 mass units;

$^1$H NMR (CDCl$_3$, TMS) δ 8.15 (dd, 2H), 7.75 (dd, 2H), 7.63 (t, 1H), 7.50 (m), 7.38 (m), 7.06 (d, 1H), 6.53 (s, 1H), 6.18 (t, 1H), 5.83 (dd, 1H), 5.76 (d, 1H), 5.02 (d, 1H), 4.80 (t, 1H), 4.65 (d, 0.5H), 4.50 (d, 0.5H), 4.38 (d, 1H), 4.29 (d, 1H), 4.04 (d, 1H), 3.55 (d, 1H), 2.70–2.40 (m), 2.40 (s, 3H), 2.37–2.25 (m), 2.21 (s, 3H), 1.75 (3H), 1.62 (s, 3H), 1.20 (s, 3H), 1.18 (s, 3H); $^{13}$C NMR (CDCl$_3$, TMS) 205.7, 172.4, 169.5, 169.4, 167.1, 166.9, 140.4, 138.0, 133.8, 133.7, 132.4, 131.9, 130.2, 129.2, 129.0, 128.75, 128.71, 128.3, 127.02, 126.98, 81.9, 81.0, 78.6, 77.2, 74.8, 73.2, 72.1, 57.0 (J=17 Hz), 54.7, 42.6, 39.9, 35.8, 16.0, 22.5, 21.0, 20.8, 14.7, 14.2 ppm.

Following the procedure described by Magri and Kingston for the preparation of 2'-[{(2,2,2-trichloroethyl)oxy}carbonyl]taxol, the 2'-[{(2,2,2-trichloroethyl)oxy}carbonyl] derivative of 7-epitaxol (ref.: Ringel, I.; Horwitz, S. B. *J. Pharmacol. Exp. Ther.*, 1987, 242, 692; preferably Chaudhary et al., J. Org. Chem., 1993, 58, 3798) is prepared.

EXAMPLE 12

2'-[{(2,2,2-Trichloroethyl)oxy}carbonyl]-7-deoxy-7-epifluorotaxol

Following the procedure of Example 10, but substituting 2'-[{(2,2,2-trichloroethyl)-oxy}carbonyl]-7-epitaxol for 2'-[{(2,2,2-trichloroethyl)oxy}carbonyl]-7-taxol, the title compound is prepared. The term 7-deoxy-7-epifluorotaxol as used in the name of the title compound means only that the configuration of the fluorine substituent is epimeric to that of 2'-[{(2,2,2-Trichloroethyl)oxy}carbonyl]-7-deoxy-7-fluorotaxol (Compound 13AA, IIIa; Example 1) and does not imply a configuration analogous to that of 7-epitaxol.

EXAMPLE 13

7-Deoxy-7-epifluorotaxol

Following the procedure of Example 11, but substituting 2'-[{(2,2,2-trichloroethyl)oxy}carbonyl]-7-deoxy-7-epifluorotaxol for 2'-[{(2,2,2-trichloroethyl)oxy}carbonyl]-7-deoxy-7-fluorotaxol, the title compound is prepared. The term 7-deoxy-7-epifluorotaxol as used in the name of the title compound means only that the configuration of the fluorine substituent is epimeric to that of 7-deoxy-7-fluorotaxol (Compound IIIb, Example 11) and does not imply a configuration analogous to that of 7-epitaxol.

EXAMPLE 14

2'-[{(2,2,2-Trichloroethyl)oxy}carbonyl]taxol, 7-Methanesulfonate

Methanesulfonyl chloride (1.2 equivalents) is added dropwise to a solution of 2'[{(2,2,2-trichloroethyl)oxy}carbonyl] taxol (1 equiv.) and pyridine (5 equiv.) in CH$_2$Cl$_2$ which is stirred at ice bath temperature. The reaction mixture is allowed to warm and stirring is continued until tlc evidence indicates that reaction is complete. The reaction mixture is quenched with ice water and is extracted with CH$_2$Cl$_2$ and these extracts are washed successively with dilute aqueous acid, dilute aqueous NaHCO$_3$, and water and then are dried, filtered, and concentrated to give the crude reaction product. Chromatography of the crude product over silica gel gives pure title compound.

EXAMPLE 15

2'-[{(2,2,2-Trichloroethyl)oxy}carbonyl]-7-deoxy-7α-chlorotaxol

A solution of 2'-[{(2,2,2-trichloroethyl)oxy}carbonyl] taxol, 7-methanesulfonate (1 equiv.) in N,N-dimethylformamide (DMF) is stirred with potassium chloride (10 equiv.). A phase transfer catalyst is added and the reaction mixture is warmed to increase the rate of reaction. The course of the reaction is followed by tlc. The reaction mixture is worked up by the addition of water and extraction with CH$_2$Cl$_2$. The organic extracts are dried, filtered, and concentrated and the crude reaction product residue is chromatographed over silica gel, yielding the pure title compound.

EXAMPLE 16

7-Deoxy-7α-chlorotaxol

Following the procedure of Example 11, but substituting 2'-[{(2,2,2-trichloroethyl)oxy}carbonyl]-7-deoxy-7α-chlorotaxol for 2'-[{(2,2,2-trichloroethyl)oxy}carbonyl]-7-deoxy-7-fluorotaxol, the title compound is prepared.

EXAMPLE 17

7-Deoxy-7β-chlorotaxol

Following the procedures of Examples 14 and 15, but starting with 2'-[{(2,2,2-trichloro-ethyl)oxy}carbonyl]-7-epitaxol, the title compound is prepared.

Following the general procedures of Examples 15 and 11 but using appropriate metal salts, such as sodium or potassium bromide and sodium or potassium iodide, in the procedure of Example 15, the following compounds are prepared:

7-Deoxy-7α-bromotaxol;
7-Deoxy-7β-bromotaxol;
7-Deoxy-7α-iodotaxol; 7-Deoxy-7β-iodotaxol.

Compounds of Formula III wherein X=chlorine, bromine or iodine can also prepared by reaction of an appropriately protected precursor (e.g., I wherein $R_1$=—$C_6H_5$; $R_2$=—NHC(O)$C_6H_5$; $R_3$=H; $R_4$=—OTROC; $R_5$=H; $R_{10}$=—COCH$_3$; and X=OH) with $(C_6H_5)_3P/X_2$; $(C_6H_5)_3P/CX_4$; or $(C_6H_5O)_3P/X_2$) following, for example, the numerous examples and experimental conditions described in Castro. B. R., *Organic Reactions*, 1983, 29, pp 1–162.

Derivatives of the 7-deoxy-7-halotaxols in which the 2'-hydroxyl group is esterified are prepared directly from the desired 7-deoxy-7-halotaxol by methods which are given in: Mathew. A. E., et. al., *J. Med. Chem.*, 1992, 35, 145; U.S. Pat. Nos. 4,960,790; 4,942,184; 5,059,699.

Following the general procedures of Mathew et al. (see, e.g., U.S. Pat. Nos. 4,960,790, 4,924,184 and 5,059,699) but substituting the appropriate 7-deoxy-7-halotaxol analog, the following compounds are prepared:

2'-succinyl-7-deoxy-7-fluorotaxol;
2'-(β-alanyl)-7-deoxy-7-fluorotaxolformate;
2'-glutaryl-7-deoxy-7-fluorotaxol;
2'-[—C(O)(CH$_2$)$_3$C(O)NH(CH$_2$)$_3$N(CH$_3$)$_2$]-7-deoxy-7-fluorotaxol;
2'-(β-sulfopropionyl)-7-deoxy-7-fluorotaxol;
2'-(2-sulfoethylamido)succinyl-7-deoxy-7-fluorotaxol;
2'-(3-sulfopropylamido)succinyl-7-deoxy-7-fluorotaxol;
2'-(triethylsilyl)-7-deoxy-7-fluorotaxol;
2'-(t-butyldimethylsilyl)-7-deoxy-7-fluorotaxol;
2'-(N,N-diethylaminopropionyl)-7-deoxy-7-fluorotaxol;
2'-(N,N-dimethylglycyl)-7-deoxy-7-fluorotaxol;
2'-(glycyl)-7-deoxy-7-fluorotaxol;
2'-(L-alanyl)-7-deoxy-7-fluorotaxol;
2'-(L-leucyl)-7-deoxy-7-fluorotaxol;
2'-(L-isoleucyl)-7-deoxy-7-fluorotaxol;
2'-(L-valyl)-7-deoxy-7-fluorotaxol;
2'-(L-phenylalanyl)-7-deoxy-7-fluorotaxol;
2'-(L-prolyl)-7-deoxy-7-fluorotaxol;
2'-(L-lysyl)-7-deoxy-7-fluorotaxol;
2'-(L-glutamyl)-7-deoxy-7-fluorotaxol;
2'-(L-arginyl)-7-deoxy-7-fluorotaxol;
7-deoxy-7-fluorotaxotere;
2'-succinyl-7-deoxy-7-chlorotaxol;
2'-(β-alanyl)-7-deoxy-7-chlorotaxolformate;
2'-glutaryl-7-deoxy-7-chlorotaxol;
2'-[—C(O)(CH$_2$)$_3$C(O)NH(CH$_2$)$_3$N(CH$_3$)$_2$]-7-deoxy-7-chlorotaxol;
2'-(β-sulfopropionyl)-7-deoxy-7-chlorotaxol;
2'-(2-sulfoethylamido)succinyl-7-deoxy-7-chlorotaxol;
2'-(3-sulfopropylamido)succinyl-7-deoxy-7-chlorotaxol;
2'-(triethylsilyl)-7-deoxy-7-chlorotaxol;
2'-(t-butyldimethylsilyl)-7-deoxy-7-chlorotaxol;
2'-(N,N-diethylaminopropionyl)-7-deoxy-7-chlorotaxol;
2'-(N,N-dimethylglycyl)-7-deoxy-7-chlorotaxol;
2'-(glycyl)-7-deoxy-7-chlorotaxol;
2'-(L-alanyl)-7-deoxy-7-chlorotaxol;
2'-(L-leucyl)-7-deoxy-7-chlorotaxol;
2'-(L-isoleucyl)-7-deoxy-7-chlorotaxol;
2'-(L-valyl)-7-deoxy-7-chlorotaxol;
2'-(L-phenylalanyl)-7-deoxy-7-chlorotaxol;
2'-(L-prolyl)-7-deoxy-7-chlorotaxol;
2'-(L-lysyl)-7-deoxy-7-chlorotaxol;
2'-(L-glutamyl)-7-deoxy-7-chlorotaxol;
2'-(L-arginyl)-7-deoxy-7-chlorotaxol;
7-deoxy-7-chlorotaxotere;
2'-succinyl-7deoxy-7-bromotaxol;
2'-(β-alanyl)-7-deoxy-7-bromotaxolformate;
2'-glutaryl-7-deoxy-7-bromotaxol;
2'-[—C(O)(CH$_2$)$_3$C(O)NH(CH$_2$)$_3$N(CH$_3$)$_2$]-7-deoxy-7-bromotaxol;
2'-(β-sulfopropionyl)-7-deoxy-7-bromotaxol;
2'-(2-sulfoethylamido)succinyl-7-deoxy-7-bromotaxol;
2'-(3-sulfopropylamido)succinyl-7-deoxy-7-bromotaxol;
2'-(triethylsilyl)-7-deoxy-7-bromotaxol;
2'-(t-butyldimethylsilyl)-7-deoxy-7-bromotaxol;
2'-(N,N-diethylaminopropionyl)-7-deoxy-7-bromotaxol;
2'-(N,N-dimethylglycyl)-7-deoxy-7-bromotaxol;
2'-(glycyl)-7-deoxy-7-bromotaxol;
2'-(L-alanyl)-7-deoxy-7-bromotaxol;
2'-(L-leucyl)-7-deoxy-7-bromotaxol;
2'-(L-isoleucyl)-7-deoxy-7-bromotaxol;
2'-(L-valyl)-7-deoxy-7-bromotaxol;
2'-(L-phenylalanyl)-7-deoxy-7-bromotaxol;
2'-(L-prolyl)-7-deoxy-7-bromotaxol;
2'-(L-lysyl)-7-deoxy-7-bromotaxol;
2'-(L-glutamyl)-7-deoxy-7-bromotaxol;
2'-(L-arginyl)-7-deoxy-7-bromotaxol;
7-deoxy-7-bromotaxotere;
2'-succinyl-7-deoxy-7-iodotaxol;
2'-(β-alanyl)-7-deoxy-7-iodotaxolformate;
2'-glutaryl-7-deoxy-7-iodotaxol;
2'-[—C(O)(CH$_2$)$_3$C(O)NH(CH$_2$)$_3$N(CH$_3$)$_2$]-7-deoxy-7-iodotaxol;
2'-(β-sulfopropionyl)-7-deoxy-7-iodotaxol;
2'-(2-sulfoethylamido)succinyl-7-deoxy-7-iodotaxol;
2'-(3-sulfopropylamido)succinyl-7-deoxy-7-iodotaxol;
2'-(triethylsilyl)-7-deoxy-7-iodotaxol;
2'-(t-butyldimethylsilyl)-7-deoxy-7-iodotaxol;
2'-(N,N-diethylaminopropionyl)-7-deoxy-7-iodotaxol;
2'-(N,N-dimethylglycyl)-7-deoxy-7-iodotaxol;
2'-(glycyl)-7-deoxy-7-iodotaxol;
2'-(L-alanyl)-7-deoxy-7-iodotaxol;
2'-(L-leucyl)-7-deoxy-7-iodotaxol;
2'-(L-isoleucyl)-7-deoxy-7-iodotaxol;
2'-(L-valyl)-7-deoxy-7-iodotaxol;
2'-(L-phenylalanyl)-7-deoxy-7-iodotaxol;
2'-(L-prolyl)-7-deoxy-7-iodotaxol;
2'-(L-lysyl)-7-deoxy-7-iodotaxol;
2'-(L-glutamyl)-7-deoxy-7-iodotaxol;
2'-(L-arginyl)-7-deoxy-7-iodotaxol;
7-deoxy-7-iodotaxotere; and
pharmaceutically acceptable salts thereof when the compound contains either an acidic or basic functional group.

EXAMPLE 18

Preparation of {2aR-[2aα,4β,4aβ,6β,9α,(αR*,βS*),11α,12α,12aα,12bα]}-β-(Benzoylamino)-α-{[(2,2,2-trichloroethoxy)carbonyl]oxy}benzenepropionic acid, 6,12b-Bis(acetyloxy)-12-(benzoyloxy)-2a,3,4,4a,5,6,9,10,11,12,12a,12b-dodecahydro-11-hydroxy-8,13,13-trimethyl-5-oxo-4,4a;7,11-bismethano-1H-cyclodeca[3,4]benz[1,2-b]-oxet-9-yl Ester; 2'-{[(2,2,2-Trichloroethyl)oxy]carbonyl}-7-deoxy-7β,8β-methanotaxol (Compound 14AA; IIa)

A solution of 2'-{[(2,2,2-trichloroethyl)oxy]carbonyl}taxol [Magri, N. F.; Kingston, D. G. I. *J. Org. Chem.*, 1986, 51, 797] (0.021 g, 0.020 mmole) in CH$_2$Cl$_2$ (1.5 mL) was added by syringe over a period of 5 min to a stirred and cooled (acetone-Dry Ice bath) solution of dimethylaminosulfur trifluoride (DAST) (2 μL, 0.014 mole in CH$_2$Cl$_2$ (0.5 mL) contained in a 3 mL Reacti-vial®. The cooling bath was removed after 15 min and the reaction container was allowed to come to room temperature. The reaction was stirred and the solution was again cooled in an acetone-Dry Ice bath and more DAST (4 μL, 0.028 mmole)

in CH$_2$Cl$_2$ was added to the reaction. The cooling bath was removed after 15 min and after 90 min the reaction solution was diluted with additional CH$_2$Cl$_2$ and then was washed with water. The layers were separated and the organic layer was dried (Na$_2$SO$_4$), filtered, and concentrated to give a residue (0.017 g). The residue was chromatographed over silica gel (40–63 μm, 60 g) using a CH$_2$Cl$_2$ solution for application to the column and 30% acetone in hexane for elution of the column. The desired title compound has R$_f$=0.22 (30% acetone-hexane) and crystallizes from acetone-hexane as colorless needles:

FAB mass spectrum gives peaks at 1012, 1010, 551, 533, 511, 491, 460, and 442 mass units; $^1$H NMR (CDCl$_3$, TMS) δ 8.19 (d, 2H), 7.71 (d, 2H), 7.59 (t, 1H), 7.48 (m), 7.36 (m), 6.98 (d, 1H), 6.57 (s, 1H), 6.28 (t, 1H), 6.08 (dd, 1H), 5.67 (d, 1H), 5.54 (d, 1H), 4.77 (dd, 2H), 4.74, 4.32 (d, 1H), 4.09 (d, 1H), 4.07, 2.47 (s, 3H), 2.19 (s, 3H), 1.90 (s, 3H), 1.67 (dd, 1H), 1.38 (m, 1H), 1.26 (s, 3H), and 1.21 (s, 3H); $^{13}$C NMR (CDCl$_3$, TMS) 201.88, 169.64, 169.59, 167.45, 167.03, 166.96, 153.24, 140.41, 136.43, 133.89, 133.61, 133.36, 132.05, 130.31, 129.25, 129.15, 129.07, 128.95, 128.75, 128.68, 128.59, 127.17, 126.49, 93.82, 84.83, 80.11, 79.56, 79.47, 77.78, 77.23, 75.66, 75.41, 72.17, 52.58, 42.85, 38.57, 35.93, 35.04. 32.26, 26.05, 22.30, 21.60, 20.83, 15.82, 14.56 ppm.

EXAMPLE 19

Preparation of {2aR-[2aα,4β,4aβ,6β,9α,(αR*,βS*),11α, 12α,12aα,12bα]}-β-(Benzoylamino)-α-hydroxybenzenepropanoic Acid, 6,12b-Bis(acetyloxy)-12-(benzoyloxy)-2a,3,4,4a,5,6,9,10,11,12,12a,12b-dodecahydro-11-hydroxy-8,13,13-trimethyl-5-oxo4,4a;7,11-bismethano-1H-cyclodeca[3,4]benz[1,2-b]-oxet-9-yl Ester, 7-Deoxy-7β,8β-methanotaxol (Compound IIb)

A solution of 2'-{[(2,2,2-trichloroethyl)oxy]carbonyl}-7-deoxy-7β,8β-methanotaxol (Compound 14AA, IIa; 0.008 g, 0.0079 mmole) in 9:1 methanol/acetic acid (1.0 mL) was stirred with activated zinc metal (0.010 g) at room temperature. After 60 min, additional zinc (0.010 g) was added and stirring was continued for 30 min. Solids were removed from the reaction mixture by filtration and the filtrate was concentrated under reduced pressure. The residue so obtained was dissolved in CH$_2$Cl$_2$ and the solution was washed successively with aqueous 0.1 N HCl, with aqueous 5% NaHCO$_3$, and with water. The organic layer was dried (Na$_2$SO$_4$), filtered, and concentrated and the residue was chromatographed over silica gel (40–63 μm, 8×250 mm column, applied in CH$_2$Cl$_2$ solution and eluted with 40% ethyl acetate in hexane). The title compound is a colorless solid:

FAB mass spectrum gives peaks at 836, 776, 758, 551, 533, 491, 286, 240, and 105 mass units; $^1$H NMR (CDCl$_3$, TMS) δ 8.19 (d, 2H), 7.69 (d, 2H), 7.60 (t, 1H), 7.60–7.35 (m), 6.95 (d, 1H), 6.31 (s, 1H), 6.25 (t, 1H), 5.82 (d, 1H), 5.66 (d, 1H), 4.78 (dd, 1H), 4.72 (d, 1H), 4.31 (d, 1H), 4.07 (d, 1H), 4.06 (m, 1H), 2.40 (s, 3H), 2.20 (s, 3H), 1.60 (s, 3H), 1.38 (m, 1H), 1.26 (s, 3H), and 1.22 (s, 3H); $^{13}$C NMR (CDCl$_3$, TMS) 204.45, 201.81, 172.74, 169.87, 169.56, 167.41, 166.96, 140.12, 138.04, 134.07, 133.53, 131.93, 130.33, 129.28, 129.04, 128.74, 128.55, 128.32, 127.04, 126.86, 84.86, 80.03, 79.57, 79.40, 77.21, 75.66, 75.46, 73.22, 72.28, 54.79, 42.86, 38.54, 36.07, 35.09, 32.15, 26.11, 22.27, 21.49, 20.88, 15.77, and 14.59 ppm.

EXAMPLE 20

Preparation of 2'-[{(2,2,2-trichloroethyl)oxy}carbonyl]-7-deoxy-7β,8β-methano-taxol (14AA; IIa) from 2'-[{(2,2,2-Trichloroethyl)-oxy}carbonyl]-7-deoxy-7-aminotaxol An ice-cold solution of sodium nitrite (1.5 equivalents) is added in portions to a vigorously stirred, ice-cold two phase mixture of a solution of 2'-[{(2,2,2-Trichloromethyl)-oxy}carbonyl]-7-deoxy-7-aminotaxol (1 equivalent) in ether and a solution of sulfuric acid in water. The mixture is stirred at ice-bath temperature for several hours following the addition. Then, excess nitrous acid is quenched by the addition of an aqueous solution of urea. The aqueous phase of the mixture is brought to near neutral pH by the careful addition of sodium carbonate, the layers are separated, and the aqueous phase is further extracted with additional ether. The combined ether extracts are dried, filtered, and concentrated to give the crude reaction product. Chromatography of the crude product over silica gel gives pure compound 14AA.

EXAMPLE 21

Preparation of 2'-[{(2,2,2-trichloroethyl)oxy}carbonyl]-7-deoxy-7β,8β-methano-taxol (14AA, IIa) from 2'-[{(2,2,2-Trichloroethyl)-oxy}carbonyl]taxol 7-Trifluoromethyl-sulfonate A solution of 2'-[[(2,2,2-Trichloroethyl)-oxy]carbonyl] taxol 7-Trifluoromethylsulfonate in 80% ethanol-water is warmed and the reaction is followed by tlc techniques. When complete, the reaction solution is neutralized with sodium bicarbonate, excess ethanol is removed under reduced pressure, and the aqueous phase is extracted with methylene chloride. The extracts are dried, filtered, and concentrated to give the crude reaction product. The crude product is chromatographed over silica gel to give pure compound 14AA.

EXAMPLE 22

N-Debenzoyl-N-benzyloxycarbonyl-7-deoxy-7-fluorotaxol (Compound 18): (({2aR-[2aα,4aβ,6β,9α,(αR*,βS*),11α, 12α,12aα,12bα]}-β-(Benzyloxycarbonylamino)-α-hydroxybenzene-propanoic acid, 6,12b-Bis(acetyloxy)-12-(benzoyloxyl)-2a,3,4,4a,5,6,9,10,11,12,12a,12b-dodecahydro-4-fluoro-11-hydroxy-4a,8,13,13-tetramethyl-5-oxo-7,11-methano-1H-cyclodeca[3,4]benz[1,2-b]-oxet-9-yl Ester))

Following the general procedure of Example No. 11 [reaction of 2'-troc-7-deoxy-7-fluorotaxol with activated zinc], but using N-debenzoyl-N-benzyloxycarbonyl-2'-{[(2, 2,2-trichloroethyl)oxy]carbonyl}-7-deoxy-7-fluorotaxol (Example 3, Compound 13BA; 0.079 g, 0.074 mmol) and activated zinc metal (0.153 g) in CH$_3$OH-HOAc (9:1, 16 mL) and EtOAc (8 mL) the desired product 18 is prepared. Following workup (two hrs reaction time) and chromatography (silica gel, 40% EtOAc-hexane, 8 mL fractions) of the crude product is obtained and the desired product 18 is eluted in fractions 59–76 as a solid and characterized on the basis of the following analytical data:

$^1$H NMR (CDCl$_3$, TMS) δ 8.14 (d, 2H, J=7.4 Hz), 7.62 (t, 1H, J=7.4 Hz), 7.52 (t, 2H, J=7.75, 7.30 Hz), 7.30–7.42 (m, 5H), 7.17 (m, 2H), 6.53 (s, 1H, H$_{10}$), 6.18 (t, 1H, H$_{13}$), 5.75 (d, 1H, —NH—), 5.73 (d, 1H, J=7.2 Hz, H$_2$), 5.38 (d, 1H, H$_3$.), 5.09 (d, 1H, J=12.5 Hz, —OCH$_a$HPh), 4.99 (d, 1H, H$_5$), 4.96 (d, 1H, J=12.3 Hz, —OCHH$_b$Ph), 4.66 (d, 1H, H$_2$.), 4.57 (dd, 1H, J$_F$=54 Hz, H$_7$), 4.36 (d, 1H, J=8.4 Hz, H$_{20a}$), 4.29 (d, 1H, H$_{20b}$), 3.41 (d, 1H, J=7.3 Hz, H$_3$), 2.63–2.46 (7 lines, 1H), 2.38 (s, 3H, —CH$_3$), 2.43–2.30 (m, 1H), 2.28–2.10 (m, 1H), 2.22 (s, 3H, —CH$_3$), 2.01 (m, 1H), 1.77 (s, 3H, —CH$_3$), 1.73 (s, 3H, —CH$_3$), 1.19 (s, 3H, —$CH_3$), 1.16 (s, 3H, —$CH_3$); $^{13}C$ NMR ($CDCl_3$, TMS), 206, 172, 169.5, 169.3, 166.9, 156, 140.5, 138, 137, 133.7, 132, 130.2, 129.3, 128.8, 128.7, 128.4, 128.0. 127.6, 126.7, 96, 93, 81.9, 80.9, 78.6, 78, 74.8, 73.6, 71.8, 66.8, 57, 56, 42.5, 39.9, 35.9, 34, 34, 25.9, 22.4, 21.0, 20.8, 14.5, 14 ppm; mass spectrum 886, 571, 511, 371, 347, 329, 316, 298, 105, 91 m/z.

EXAMPLE 23

N-Debenzoyl-N-benzyloxycarbonyl-7-deoxy-7β,8β-methanotaxol (Compound 21); ((({2aR-[2aα,4β,4aβ,6β,9α,(αR*,βS*),11α,12α,12aα,12bα]}-β-(Benzyloxycarbonylamino)-α-hydroxybenzenepropanoic acid, 6,12b-Bis(acetyloxy)-12-(benzoyloxy)-2a,3,4,4a,5,6,9,10,11,12,12a,12b-dodecahydro-11-hydroxy-8,13,13-trimethyl-5-oxo-4,4a;7,11-bismethano-1H-cyclodeca[3,4]benz[1,2-b]-oxet-9-yl Ester))

Following the general procedure of Example 11 [reaction of 2'-troc-7-deoxy-7-fluorotaxol with activated zinc], but using N-debenzoyl-N-benzyloxycarbonyl-2'-{[(2,2,2-trichloroethyl)oxy]carbonyl}-7-deoxy-7β,8β-methanotaxol (14BA; 0.040 g, 0.038 mmol) and activated zinc metal (0.072 g followed by an additional 0.072 g) in $CH_3OH$-HOAc (9:1, 10 mL) the desired product 21 is prepared. Following workup after 3 hrs reaction time and chromatography (silica gel, 40% EtOAc-hexane, 8 mL fractions) of the crude product, starting material (0.007 g) is recovered in fractions 30–37 and the desired product (21, 0.020 g, 0.023 mmol, 61%) is eluted in fractions 75–100 and obtained as a solid and characterized on the basis of the following analytical data:

$^1H$ NMR ($CDCl_3$, TMS) δ 8.17 (d, 2H, J=7.3 Hz), 7.58 (m, 1H), 7.50 (t, 2H), 7.42–7.30 (m, 5H), 7.24 (m), 7.08 (m, 2H), 6.31 (s, 1H, $H_{10}$), 6.26 (t, 1H, J=8.6 Hz, $H_{13}$), 5.70 (d, 1H, J=9.6 Hz, —NH—), 5.64 (d, 1H, J=7.7 Hz, $H_2$), 5.38 (d, 1H, J=8.1 Hz, $H_3$·), 4.98 (d, 1H, J=12.5 Hz, —$OCH_aHPh$), 4.88 (d, 1H, J=12.5 Hz, —$OCHH_bPh$), 4.71 (d, 1H, J=3.7 Hz, $H_5$), 4.65 (s, 1 H, $H_2$·), 4.28 (d, 1H, J=8.6 Hz, $H_{20a}$), 4.07 (d, 1H, $H_3$), 4.05 (d, 1H, $H_{20b}$), 2.49–2.34 (m, 1H), 2.38 (s, 3H, —$CH_3$), 2.23 (m), 2.21 (s, 3H, —$CH_3$), 2.08 (m), 1.94 (m), 1.82 (s, 3H, —$CH_3$), 1.37 (m, 1H, $H_7$), 1.25 (s, 3H, —$CH_3$), 1.21 (s, 3H, —$CH_3$); $^{13}C$ NMR ($CDCl_3$, TMS) 202, 172.5, 169.2, 169.1, 167, 155.5, 149.5, 138, 136, 133.5, 133, 130.0, 128.6, 128.4, 128.1, 127.7, 127.2, 126.3, 84.5, 79.9, 79.2, 79.0, 75.3, 75.2, 73, 71.7, 66.5, 56, 42.5, 38.2, 36, 34.7, 32, 25.7, 21.5, 21, 20.5, 15.5, 14.2 ppm; mass spectrum: 866.3423, $C_{48}H_{51}NO_{14}$+H requires 866.3388, 848, 806, 788, 551, 533, 491, 105, 91 m/z.

EXAMPLE 24

N-Debenzoyl-N-(t-butyl)oxycarbonyl-2'-{[(2,2,2-trichloroethyl)oxy]carbonyl}-7-deoxy-7-fluorotaxol (Compound 13DA); ((({2aR-[2aα,4aβ,6β,9α,(αR*,βS*),11α,12α,12aα,12bα]}-β-[(t-Butyl)oxycarbonylamino]-α-{[(2,2,2-trichloroethoxy)carbonyl]oxy}benzenepropanoic acid, 6,12b-Bis(acetyloxy)-12-(benzoyloxy)-2a,3,4,4a,5,6,9,10,11,12,12a,12b-dodecahydro-4-fluoro-11-hydroxy-4a,8,13,13-tetramethyl-5-oxo-7,11-methano-1H-cyclodeca[3,4]benz[1,2-b]-oxet-9-yl Ester)); and N-Debenzoyl-N-(t-butyl)oxycarbonyl-2'-{[(2,2,2-trichloroethyl)oxy]carbonyl}-7-deoxy-7β,8β-methanotaxol (Compound 14DA), ((({2aR-[2aα,4β,4aβ,6β,9α(αR*,βS*),11α,12α,12aα,12bα]}-β-[(t-Butyl)oxycarbonylamino]-α-{[(2,2,2-trichloroethoxy)carbonyl]oxy}benzenepropanoic acid, 6,12b-Bis(acetyloxy)-12-(benzoyloxy)-2a,3,4,4a,5,6,9,10,11,12,12a,12b-dodecahydro-11-hydroxy-8,13,13-trimethyl-5-oxo-4,4a;7,11-bismethano-1H-cyclodeca[3,4]benz[1,2-b]-oxet-9-yl Ester));

The general procedure of Example 10 [reaction of 2'-troctaxol with methylDAST] is followed, using N-debenzoyl-N-(t-butyl)oxycarbonyl-2'-troc-taxol (Compound 12DA; 1.800 g, 1.75 mmoles) and dimethylaminosulfur trifluoride (methylDAST, 286 μL, 0.390 g, 2.93 mmoles) in $CH_2Cl_2$ (120 mL) under $N_2$ at −78° C. Following workup, the crude product mixture (1.77 g) is chromatographed over silica gel (40–63 μm, 191 g in a 37×350 mm column, 45 mL fractions) using a $CH_2Cl_2$ solution for application of the material to the column and 20% acetone-hexane (1.5 L) followed by 25 % acetone-hexane to elute the column. A mixture containing 14DA (0.511 g) is eluted in fractions 41–46. Fractions 47–48 (0.085 g) contain a mixture of products. Fractions 49–61 (0.814 g) contain pure 13DA. Rechromatography of the mixed fractions 47–48 provides additional amounts of a mixture containing 14DA and of pure 13DA.

Pure 13DA is obtained as a solid and characterized on the basis of the following analytical data:

$^1H$ NMR ($CDCl_3$, TMS) δ 8.15 (d, 2H, J=7.2 Hz), 7.62 (t, 1H, J=7.2 Hz), 7.51 (t, 2H, J=7.7 Hz), 7.25–7.44 (m, 5H), 6.58 (s, 1H, $H_{10}$), 6.28 (t, 1H, J=8.7 Hz, $H_{13}$), 5.77 (d, 1H, J=7.2 Hz, $H_2$), 5.51 (d, 1H, —NH—), 5.48 (d, 1H, J=10.0 Hz, $H_3$·), 5.40 (d, 1H, J=2.0 Hz, $H_2$·), 5.05 (d, 1H, J=8.1 Hz, $H_5$), 4.77 (d, 1H, J=11.8 Hz, troc-$H_a$), 4.68 (d, 1H, J=11.8 Hz, troc-$H_b$), 4.58 (dd, 1H, J=4.6, 46.9 Hz, $H_7$), 4.39 (d, 1H, J=8.4 Hz, $H_{20a}$), 4.27 (d, 1H, J=8.4 Hz, $H_{20b}$), 4.04 (d, 1H, J=7.1 Hz, $H_3$), 2.57 (m, 1H, $H_{6a}$), 2.48 (s, 3H, —$CH_3$), 2.21 (s, 3H, —$CH_3$), 1.91 (s, 3H, —$CH_3$), 1.73 (s, 3H, —$CH_3$), 1.34 (s, 9H, $Me_3C$—), 1.23 (s, 3H, —$CH_3$), 1.17 (s, 3H, —$CH_3$); mass spectrum, found: 1026.2660, $C_{48}H_{55}Cl_3FNO_{16}$+H requires 1026.2648, 970, 571, 511, 407, 389, 347, 329, 105, 57 m/z.

All fractions containing a mixture of 14DA are combined and rechromatographed over silica gel (two size B Merck Lobar columns, 9 mL fractions) by applying the material to the column in a $CH_2Cl_2$ solution and eluting the column with 10% $CH_3CN$—$CH_2Cl_2$ (68 fractions) followed by 15% $CH_3CN$—$CH_2Cl_2$, The pure compound 14DA is eluted in fractions 100–131 as a solid and characterized on the basis of the following analytical data:

$^1H$ NMR ($CDCl_3$, TMS) δ 8.15 (d, 2H, J=7.1 Hz), 7.61 (t, 1H, J=7.3 Hz), 7.51 (t, 2H, J=7.5 Hz), 7.30–7.44 (m, 5H), 6.34 (s, 1H, $H_{10}$), 6.30 (t, 1H, J=8.6 Hz, $H_{13}$), 5.67 (d, 1H, J=7.6 Hz, $H_2$), 5.54 (d, 1H, —NH—), 5.45 (d, 1H, J=10.1 Hz, $H_3$·), 5.38 (d, 1H, J=2.3 Hz, $H_2$·), 4.76 (d, 1H, J=11.8 Hz, troc-$H_a$), 4.76 (1H, $H_5$), 4.69 (d, 1H, J=11.8 Hz, troc-$H_b$), 4.33 (d, 1H, J=8.6 Hz, $H_{20a}$), 4.09 (d, 1H, J=7.5 Hz, $H_3$), 4.04 (d, 1H, J=8.7 Hz, $H_{20b}$), 2.48 (m, 1H, $H_{14a}$), 2.44 (s, 3H, —$CH_3$), 2.37 (m, 1H, $H_{6a}$), 2.24 (m, 1H, $H_{19a}$), 2.20 (s, 3H, —$CH_3$), 2.11 (d, 1H, J=16.0 Hz, $H_{14b}$), 1.90 (s, 3H, —$CH_3$), 1.66 (m, 1H, $H_{19b}$), 1.37 (m, 1H, $H_7$), 1.28 (s, 9H, $Me_3C$—), 1.27 (s, 3H, —$CH_3$), 1.25 (s, 3H, —$CH_3$); mass spectrum, found: 1006.2560, $C_{48}H_{54}Cl_3NO_{16}$+H requires 1006.2486, 950, 551, 533, 491, 369, 327, 105, 57 m/e.

EXAMPLE 25

N-Debenzoyl-N-(t-butyl)oxycarbonyl-7-deoxy-7-fluorotaxol (Compound 20), ((({2aR-[2aα,4aβ,6β,9α,(αR*,βS*),11α,12α,12aα,12bα]}-β-(t-Butyl)oxycarbonylamino]-α-hydroxybenzene-propanoic acid, 6,12b-Bis(acetyloxy)-12-(benzoyloxy)-2a,3,4,4a,5,6,9,10,11,12,12a,12b-dodecahydro-4-fluoro-11-hydroxy-4a,8,13,13-tetramethyl-5-oxo-7,11-methano-1H-cyclodeca[3,4]benz[1.2-b]-oxet-9-yl Ester)), The general procedure of Example 11 [reaction of 2'-troc-7-deoxy-7-fluorotaxol with activated zinc] is followed, using N-debenzoyl-N-(t-butyl)oxycarbonyl-2'-{[(2,2,2- trichloroethyl)oxy]carbonyl}-7-deoxy-7-fluorotaxol (13DA, 0.100 g, 0.097 mmol) and activated zinc metal (0.183 g followed by an additional 0.050 g) in CH$_3$OH-HOAc (9:1, 10 mL). After 1 hr of reaction time, the reaction mixture is stored overnight at −33° C., then worked up and the crude product chromatographed (silica gel, 40% EtOAc-hexane, 8 mL fractions) to give the desired product 20 in fractions 53–76 as a solid and characterized on the basis of the following analytical data:

$^1$H NMR (CDCl$_3$, TMS) δ 8.13 (d, 2H, J=7.2 Hz), 7.62 (t, 1H, J=7.4 Hz), 7.51 (t, 2H, J=7.5 Hz), 7.30–7.42 (m, 5H), 6.56 (s, 1H, H$_{10}$), 6.21 (t, 1H, H$_{13}$), 5.76 (d, 1H, J=7.2 Hz, H$_2$), 5.42 (d, 1H, J=9.7 Hz, —NH—), 5.29 (d, 1H, H$_3$), 5.01 (d, 1H, J=7.5 Hz, H$_5$), 4.63 (m, 1H, H$_{2'}$), 4.57 (dd, 1H, J=4.3, 46.8 Hz, H$_7$), 4.37 (d, 1H, J=8.4 Hz, H$_{20a}$), 4.27 (d, 1H, J=8.4 Hz. H$_{20b}$), 4.04 (d, 1H, J=7.1 Hz, H$_3$), 2.56 (seven lines, 1H, H$_{6a}$), 2.39 (s, 3H, —CH$_3$), 2.31 (m, 1H), 2.25 (m, 1H), 2.22 (s, 3H, —CH$_3$), 2.14 (dd, 1H), 1.81 (s, 3H, —CH$_3$), 1.73 (s, 3H, —CH$_3$), 1.34 (s, 9H, Me$_3$C—), 1.23 (s, 3H, —CH$_3$), 1.18 (s, 3H, —CH$_{13}$);

EXAMPLE 26

N-Debenzoyl-N-(t-butyl)oxycarbonyl-7-deoxy-7β,8β-methanotaxol (Compound 23), (({2aR-[2aα,4β,4aβ,6β,9α(αR*,βS*),11α,12α,12aα,12bα]}-β-[(t-Butyl)oxycarbonylamino]-α-hydroxybenzenepropanoic acid, 6,12b-Bis(acetyloxy)-12-(benzoyloxy)-2a,3,4,4a,5,6,9,10,11,12,12a,12b-dodecahydro-11-hydroxy-8,13,13-trimethyl-5-oxo-4,4a;7,11-bismethano-1H-cyclodeca[3,4]benz[1,2-b]-oxet-9-yl Ester))

The general procedure of Example 11 [reaction of 2'-troc-7-deoxy-7-fluorotaxol with activated zinc] is followed, using N-debenzoyl-N-(t-butyl)oxycarbonyl-2'-{[(2,2,2-trichloroethyl)oxy]carbonyl}-7-deoxy-7β,8β-methanotaxol (14DA, 0.100 g, 0.099 mmol) and activated zinc metal (0.200 g followed by an additional 0.050 g) in CH$_3$OH-HOAc (9:1, 10 mL). Following workup after 3 hrs reaction time and chromatography (silica gel, 40% EtOAc-hexane, 8 mL fractions) of the crude product there is obtained, the desired product 23 which is eluted in fractions 58–86 a solid and is characterized on the basis of the following analytical data:

$^1$H NMR (CDCl$_3$, TMS) δ 8.15 (d, 2H, J=7.2 Hz), 7.61 (t, 1H, J=7.3 Hz), 7.51 (t, 2H, J=7.7 Hz), 7.28–7.45 (m, 5H), 6.33 (s, 1H, H$_{10}$), 6.27 (t, 1H, H$_{13}$), 5.67 (d, 1H, J=7.6 Hz, H$_2$), 5.36 (d, 1H, J=9.5 Hz, H$_3$), 5.30 (m, 1H, —NH—). 4.73 (d, 1H, J=3.7 Hz, H$_{2'}$), 4.62 (m, 1H, H$_5$), 4.31 (d, 1H, J=8.6 Hz, H$_{20a}$), 4.09 (d, 1H, J=7.5 Hz, H$_3$), 4.04 (d, 1H, J=8.7 Hz, H$_{20b}$), 2.46 (d of t, 1H, J=4.3. 16.1 Hz, H$_{6a}$), 2.38 (s, 3H, —CH$_3$), 2.24 (m , 1H), 2.21 (s, 3H, —CH$_3$), 2.10 (d, 1H, J=16.0 Hz), 1.85 (s, 3H, —CH$_3$), 1.67 (dd, 1H, J=7.1, 5.2 Hz), 1.36 (m, 1H, H$_7$), 1.28 (s, 12H, Me$_3$C—, CH$_3$—), 1.25 (s, 3H, —CH$_3$);

EXAMPLE 29

2'-TES-7-deoxy-7α-chlorotaxol

A solution of 2'-TES-taxol 7-triflate (Preparation 15A; 1 equiv.) in N,N-dimethylformamide (DMF) is stirred with potassium chloride (10 equiv.). A phase transfer catalyst is added and the reaction mixture is warmed to increase the rate of reaction. The course of the reaction is followed by tlc. The reaction mixture is worked up by the addition of water and extraction with CH$_2$Cl$_2$. The organic extracts are dried, filtered, and concentrated and the crude reaction product residue is chromatographed over silica gel, yielding the pure title compound.

EXAMPLE 30

7-Deoxy-7α-chlorotaxol

Following the procedures of Preparation 12A, but starting with 2'-TES-7-deoxy-7α-chlorotaxol, the title compound is prepared.

Following the general procedures of Example 29 and 30 but using appropriate metal salts, such as sodium or potassium bromide and sodium or potassium iodide, in the procedure of Example 29, the following compounds are prepared:

7-Deoxy-7α-bromotaxol;
7-Deoxy-7β-bromotaxol;
7-Deoxy-7α-iodotaxol;
7-Deoxy-7β-iodotaxol.

EXAMPLE 31

Preparation of N-debenzoyl-N-(t-butyl)aminocarbonyl-7-deoxy-7-fluoro-taxol; Compound 28

N-Debenzoyl-N-Cbz-7-deoxy-7-fluoro-taxol 18 (60 mg, 0.07 mM; Preparation 39) is dissolved in 3 mL absolute ethanol and 20 mg 10% Pd on carbon is added. This is hydrogenated at atmospheric pressure for 6 hrs. TLC shows no starting material left so reaction is filtered through Celite and concentrated in vacuo. The residue, which is 13-(β-phenyl-isoserinyl)-7-fluoro-baccatin III, (19, 52 mg, 0.07 mM; Preparation 40) is dissolved in 700 μL THF and cooled to 0° C. and 7 μL (0.061 mM) t-butyl isocyanate added. TLC shows some amine remaining so another 7 μL is added. After 20 hrs the solution is concentrated in vacuo and chromatographed over 6 gm of silica gel packed in 1:2 EtOAc:hexane. The column is eluted with 30 mL 1:2 EtOAc:Hexane, 60 mL 2:3 EtOAc:hexane, 50 mL 1:1 EtOAc:hexane, and 20 mL 2:1 EtOAc:hexane collecting 3 mL fractions. The desired N-debenzoyl-N-(t-butyl)aminocarbonyl-7-deoxy-7-fluoro-taxol is found in fractions 35–52.

Mass Spec (FAB-High Res.) Theory: 851.3766 Found: 851.3792 $^1$H NMR (CDCl$_3$; TMS): δ 1.16 (s,3H); 1.20 (s); 1.72 (s,3H); 1.80 (s,3H); 2.15–2.60 (m); 2.19 (s,3H); 2.52 (s,3H); 4.02 (d,1H); 4.28 (d,1H); 4.35 (d,1H); 4.55 (dd,1H); 4.59 (d,1H); 4.88 (br s,1H); 4.99 (d,1H); 5.34 (m,2H); 5.76 (d,1H); 6.13 (m,1H); 6.55 (s,1H); 7.32 (m); 7.49 (m,2H); 7.61 (m,1H); 8.11 (d,2H)

EXAMPLE 32

Preparation of N-debenzoyl-N-(t-butyl)aminocarbonyl-7-deoxy-7β,8β-methano-taxol; Compound 29

N-Debenzoyl-N-Cbz-7-deoxy-7β,8β-methano-taxol 21 (60 mg, 0.07 mM; Preparation 42) is dissolved in 3 mL absolute ethanol and 20 mg 10% Pd on carbon is added. This is hydrogenated at atmospheric pressure for 5.5 hrs. TLC shows no starting material left so reaction is filtered through Celite and concentrated in vacuo.

The residue, which is 13-(β-phenyl-isoserinyl)-7-deoxy-7β,8β-methano-baccatin III, (22, 52 mg, 0.07 mM; Preparation 43) is dissolved in 1 mL THF and 8 mL (0.07 mM) t-butyl isocyanate added. TLC shows some amine remains so the reaction is cooled to 0° C. and 7 mL t-butyl isocyanate added. Amine still remains so another 7 mL and 3×5 mL is added checking the reaction by TLC between each addition. To the reaction is added water to quench and the solution is partitioned between acidic brine and EtOAc. The layers are separated and the organic layer is filtered through Na$_2$SO$_4$ and concentrated in vacuo and chromatographed over 6 gm of silica gel packed in 1:2 EtOAc:hexane. The column is eluted with 30 mL 1:2 EtOAc:hexane, 50 mL 2:3 EtOAc:hexane, and 80 mL 1:1 EtOAc:hexane collecting 3 mL fractions. The desired N-debenzoyl-N-(t-butyl) aminocarbonyl-7-deoxy-7β,8β-methano-taxol is found in fractions 2948.

Mass Spec (FAB-High Res.) Theory: 831.3704 Found: 831.3717 $^1$H NMR (CDCl$_3$; TMS): δ 1.18 (s); 1.23 (s,3H); 1.26 (s,3H); 1.66 (m); 1.82 (s,3H); 1.98–2.48 (m); 2.20 (s,3H); 2.38 (s,3H); 4.05 (m,2H); 4.30 (d,1H); 4.50 (m,1H); 4.60 (d,1H); 4.73 (m,1H); 5.33 (m,1H); 5.66 (d,1H); 6.19 (m,1H); 6.31 (s,1H); 7.32 (m); 7.51 (m,2H); 7.61 (m,1H); 8.13 (d,2H)

Derivatives of the 7-deoxy-7β,8β-methano-taxols in which the 2'-hydroxyl group is esterified are prepared directly from the desired 7-deoxy-7β,7β-methano-taxol by methods which are given in: Mathew, A. E., et.al., *J. Med. Chem.*, 1992, 35, 145; U.S. Pat. Nos. 4,960,790; 4,942,184; 5,059,699.

Following the general procedures of Mathew et al. (see, e.g., U.S. Pat. Nos. 4,960,790, 4,924,184 and 5,059,699) but substituting the appropriate 7-deoxy-7β,8β-methano-taxol analog, the following compounds are prepared:

2'-succinyl-7-deoxy-7β,8β-methano-taxol;
2'-(β-alanyl)-7-deoxy-7β,8β-methano-taxolformate;
2'-glutaryl-7-deoxy-7β,8β-methano-taxol;
2'- [—C(O)(CH$_2$)$_3$C(O)NH(CH$_2$)$_3$N(CH$_3$)$_2$]-7-deoxy-7β,8β-methano-taxol;
2'-(β-sulfopionyl)-7-deoxy-7β,8β-methano-taxol;
2'-(2-sulfoethylamido)succinyl-7-deoxy-7β,8β-methano-taxol;
2'-(3-sulfopropylamido)succinyl-7-deoxy-7β,8β-methano-taxol;
2'-(triethylsilyl)-7-deoxy-7β,8β-methano-taxol;
2'-(t-butyldimethylsilyl)-7-deoxy-7β,8β-methano-taxol;
2'-(N,N-diethylaminopropionyl)-7-deoxy-7β,8β-methano-taxol;
2'-(N,N-dimethylglycyl)-7-deoxy-7β,8β-methano-taxol;
2'-(glycyl)-7-deoxy-7β,8β-methano-taxol;
2'-(L-alanyl)-7-deoxy-7β,8β-methano-taxol;
2'-(L-leucyl)-7-deoxy-7β,8β-methano-taxol;
2'-(L-isoleucyl)-7-deoxy-7β,8β-methano-taxol;
2'-(L-valyl)-7-deoxy-7β,8β-methano-taxol;
2'-(L-phenylalanyl)-7-deoxy-7β,8β1-methano-taxol;
2'-(L-prolyl)-7-deoxy-7β,8β-methano-taxol;
2'-(L-lysyl)-7-deoxy-7β,8β-methano-taxol;
2'-(L-glutamyl)-7-deoxy-7β,8β-methano-taxol;
2'-(L-arginyl)-7-deoxy-7β,8β-methano-taxol:
7-deoxy-7β,8β-methano-taxotere; and pharmaceutically acceptable salts thereof when the compound contains either an acidic or basic functional group.

Taxol and the other starting taxol analogs are known or can be readily prepared by known methods. See The Chemistry of Taxol, Pharmac. Ther., Vol 52, pp 1–34, 1991 as well as:

U.S. Pat. Nos. 4,814,470; 4,857,653; 4,942,184; 4,924,011; 4,924,012; 4,960,790; 5,015,744; 5,059,699; 5,136,060; 5,157,049; 4,876,399; 5,227,400 as well as PCT Publication No. WO 92/09589, European Patent Application 90305845.1 (Publication No. A2 0 400 971). 89400935.6 (Publication No. A1 0 366 841) and 90402333.0 (Publication No. 0 414 610 A1). 87401669.4 (A1 0 253 739), 92308608.6 (A1 0 534 708). 92308609.4 (A1 534 709), and PCT Publication Nos. WO 91/17977, WO 91/17976, WO 91/13066, WO 91/13053 all of which are incorporated herein by reference.

The compounds of the invention can be formulated per se in pharmaceutical preparations or formulated in the form of pharmaceutically acceptable salts thereof, particularly as nontoxic pharmaceutically acceptable addition salts or acceptable basic salts. These salts can be prepared from those compounds of the invention which contain acidic or basic groups according to conventional chemical methods.

Normally, the salts are prepared by reacting the free base or acid with stoichiometric amounts or with an excess thereof of the desired salt forming inorganic or organic acid in a suitable solvent or various combination of solvents. As an example, the free base can be dissolved in an aqueous solution of the appropriate acid and the salt recovered by standard techniques, for example, by evaporation of the solution. Alternatively, the free base can be dissolved in an organic solvent such as a lower alkanoyl, an ether, an alkyl ester, or mixtures thereof, for example, methanol, ethanol, ether, ethylacetate, an ethylacetate-ether solution, and the like, whereafter it is treated with the appropriate acid to form the corresponding salt. The salt is recovered by standard recovery techniques. for example, by filtration of the desired salt on spontaneous separation from the solution or it can be precipitated by the addition of a solvent in which the salt is insoluble and recovered therefrom.

The taxol derivatives of the invention can be utilized in the treatment of cancers, due to their cytotoxic, antitumor activity. The new compounds are administrable in the form of tablets, pills, powder mixtures, capsules, injectables, solutions, suppositories, emulsions, dispersions, food premix, and in other suitable form. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50–500 mg. Typical of pharmaceutically acceptable carriers are, for example, mannitol, urea, dextrans, lactose, potato and maize starches, magnesium stearate, talc, vegetable oils, polyalkylene glycols, ethyl cellulose, poly (vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

Exemplary of a typical method for preparing a tablet containing the active agents is to first mix the agent with a nontoxic binder such as gelatin, acacia mucilage, ethyl cellulose, or the like. The mixing is suitably carried out in a standard V-blender and usually under anhydrous conditions. Next, the just prepared mixture can be slugged through conventional tablet machines and the slugs fabricated into tablets. The freshly prepared tablets can be coated, or they can be left uncoated. Representative of suitable coatings are the nontoxic coatings including shellac, methylcellulose, carnauba wax, styrene-maleic acid copolymers, and the like. For oral administration, compressed tablets containing 0.01 milligram, 5 milligrams, 25 milligrams, 50 milligrams, 500 milligrams, etc., up to 2500 milligrams are manufactured in the light of the above disclosure and by art known fabrication techniques well known to the art and set forth in Remington's Pharmaceutical Science, Chapter 39, Mack Publishing Co., 1965.

To formulate the tablet, the active compound, cornstarch, lactose, dicalcium phosphate and calcium carbonate are uniformly blended under dry conditions in a conventional V-blender until all the ingredients are uniformly mixed together. Next, the cornstarch paste is prepared as a 10% paste and it is blended with the just prepared mixture until a uniform mixture is obtained. The mixture is then passed through a standard light mesh screen, dried in an anhydrous atmosphere and then blended with calcium stearate, and compressed into tablets, and coated if desired. Other tablets containing 10, 50, 100, 150 mgs, etc., are prepared in a like fashion.

The following Formulation 1 is an example of a tablet formulation comprising a compound of the invention.

FORMULATION I

| Ingredients: | Per tablet, mg. |
| --- | --- |
| Active compound | 50.0 |
| Cornstarch | 15.0 |
| Cornstarch paste | 4.5 |
| Calcium carbonate | 15.0 |
| Lactose | 67.0 |
| Calcium stearate | 2.0 |
| Dicalcium phosphate | 50.0 |

The manufacture of capsules containing 10 milligrams to 2500 milligrams for oral use consists essentially of mixing the active compound with a nontoxic carrier and enclosing the mixture in a polymeric sheath, usually gelatin or the like. The capsules can be in the art known soft form of a capsule made by enclosing the compound in intimate dispersion within an edible, compatible carrier, or the capsule can be a hard capsule consisting essentially of the novel compound mixed with a nontoxic solid such as talc, calcium stearate, calcium carbonate, or the like. Capsules containing 25 mg, 75 mg, 125 mg, and the like, of the novel compound, singularly or mixtures of two or more of the novel compounds are prepared, for example, as follows:

FORMULATION II

| Ingredients | Per Capsule, mg. |
| --- | --- |
| Active compound | 50.0 |
| Calcium carbonate | 100.0 |
| Lactose. U.S.P. | 200.0 |
| Starch | 130.0 |
| Magnesium stearate | 4.5 |

The above ingredients are blended together in a standard blender and then discharged into commercially available capsules. When higher concentrations of the active agent is used, a corresponding reduction is made in the amount of lactose.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The dose administered, whether a single dose, multiple dose, or a daily dose, will of course, vary with the particular compound of the invention employed because of the varying potency of the compound, the chosen route of administration, the size of the recipient and the nature of the patient's condition. The dosage administered is not subject to definite bounds, but it will usually be an effective amount, or the equivalent on a molar basis of the pharmacologically active free form produced from a dosage formulation upon the metabolic release of the active drug to achieve its desired pharmacological and physiological effects.

Typically the compounds of the invention can be administered by intravenous injection at doses of 1–500 mg per patient per course of treatment, preferable with doses of 2–100 mg, the exact dosage being dependent on the age, weight, and condition of the patient. An example of a suitable formulation for injection is using a solution of the compound of the invention in a mixture of polysorbate alcohol and dehydrated alcohol (e.g., 1:1) followed by dilution with 5% dextrose in water prior to infusion or injection.

The compounds of Formula 1 (including II and III) are useful for the same cancers for which taxol has been shown active, including human ovarian tumors, mammary rumors, and malignant melanoma, lung tumors, gastric tumors, colon tumors, head and neck tumors, and leukemia See, e.g., the clinical pharmacology of taxol is reviewed by Eric K. Rowinsky and Ross C. Donehower, The Clinical Pharmacology and Use of Antimicrotubule Agents in Cancer Chemotherapeutics, Pharmac. Ther., Vol 52, pp 35–84, 1991. Clinical and preclinical studies with taxol are reviewed by William J. Slichenmyer and Daniel D. Von Hoff, Taxol: A New and Effective And-cancer Drug, Anti-Cancer Drugs, Vol. 2, pp 519–530, 1991.

The biological activity of the 7-deoxy-7$\beta$,8$\beta$-methanotaxol compounds (Formula II) of the invention has been confirmed using well known procedures. For example, comparison of the cytotoxicity of 7-deoxy-7$\beta$,8$\beta$-methanotaxol (Compound IIb; product of example 19) with taxol itself in L1210 mouse leukemia carcinoma cells in culture indicated that the IC$_{90}$ (90% growth inhibitory concentration) for 7-deoxy-7$\beta$,8$\beta$-methanotaxol was 0.025 micrograms/ml and for taxol was 0.06 micrograms/ml. In an in vitro tubulin polymerization assay, conducted after the manner of F. Gaskin, et al., *J. Mol. Biol.*, 89:737, 1974, 7-deoxy-7$\beta$,8$\beta$-methano-taxol was able to induce tubulin polymerization in vitro at 20° C. in a manner very similar to taxol.

The biological activity of the 7-deoxy-7-halotaxol compounds (Formula III) of the invention has been confirmed using well known procedures. For example, comparison of the cytotoxicity of 7-deoxy-7-fluorotaxol (Compound IIIb: product of example 11) with taxol itself in A2780 (human ovarian carcinoma) cells in culture indicated that the IC$_{90}$ (90% growth inhibitory concentration) for 7-deoxy-7-fluorotaxol was 0.016 micrograms/ml and for taxol was 0.007 micrograms/ml. In an in vitro tubulin polymerization assay, conducted after the manner of F. Gaskin, et al.,*J. Mol. Biol.*, 89:737, 1974, 7-deoxy-7-fluorotaxol was able to induce tubulin polymerization in vitro at 20° C. in a manner very similar to taxol. In this assay, 7-deoxy-7-fluoro taxol was approximately half as potent as taxol.

The biological activity of the compounds of this invention has been further confirmed using well known procedures against L1210 leukemia and the results set forth in Table I. The results were obtained using standard well known procedure (Li, L. H.; Kuentzel, S. L.; Murch, L. L.; Pschigoga, L. M.; and W. C. Krueger, "Comparative biological and biochemical effects of nogalamycin and its analogs on L1210 leukemia," Cancer Res. 39:4816–4822 (1979)). The results are expressed as an IC$_{50}$ which is the drug concentration required to inhibit cell proliferation to 50% of that of untreated control cells. Lower numbers indicated greater activity.

TABLE 1
| Compound No. | L1210 (IC$_{50}$ μg/ml) |
| --- | --- |
| 13AA | 0.054 |
| 14AA | >0.1 |
| IIIb | 0.010 |
| IIb | 0.012 |
| 13DA | 0.015 |
| 14DA | 0.012 |
| 20 | 0.0038 |
| 23 | 0.0046 |
| 28 | 0.0055 |
| 29 | 0.006 |
| Taxol | 0.015 |
| Taxotere | 0.004 |
CHART A-I
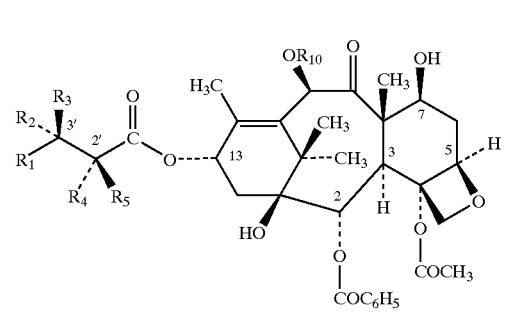
A-1
CHART A-II
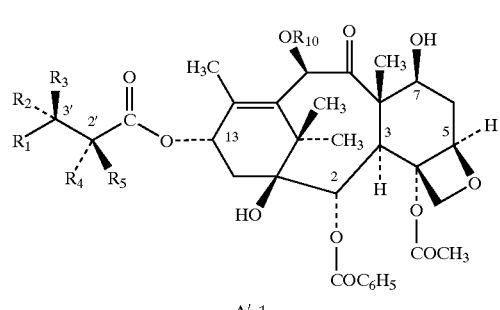
A'-1
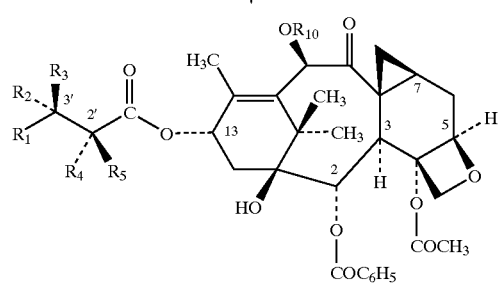
A'-2
-continued
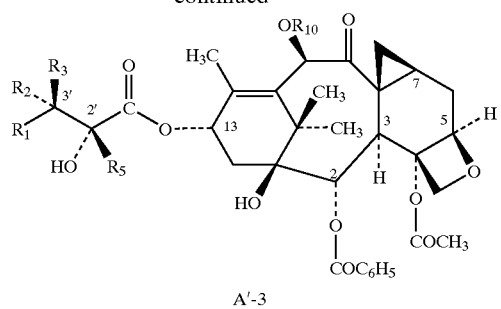
A'-3
CHART A-III
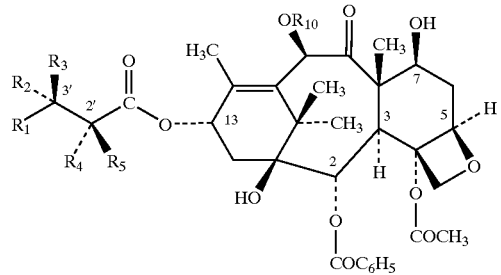
A''-1
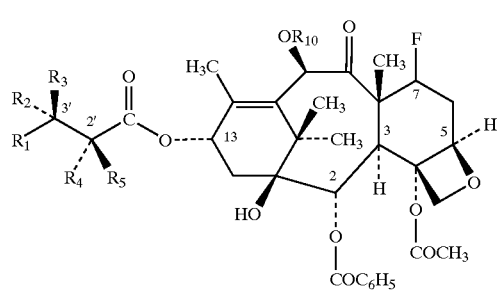
A''-2
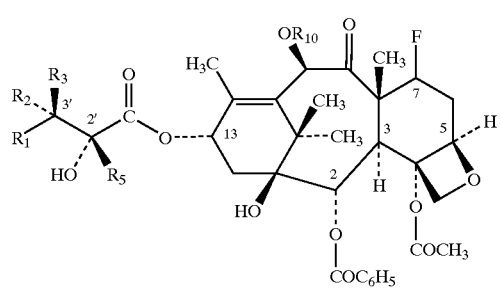
A''-3

CHART A
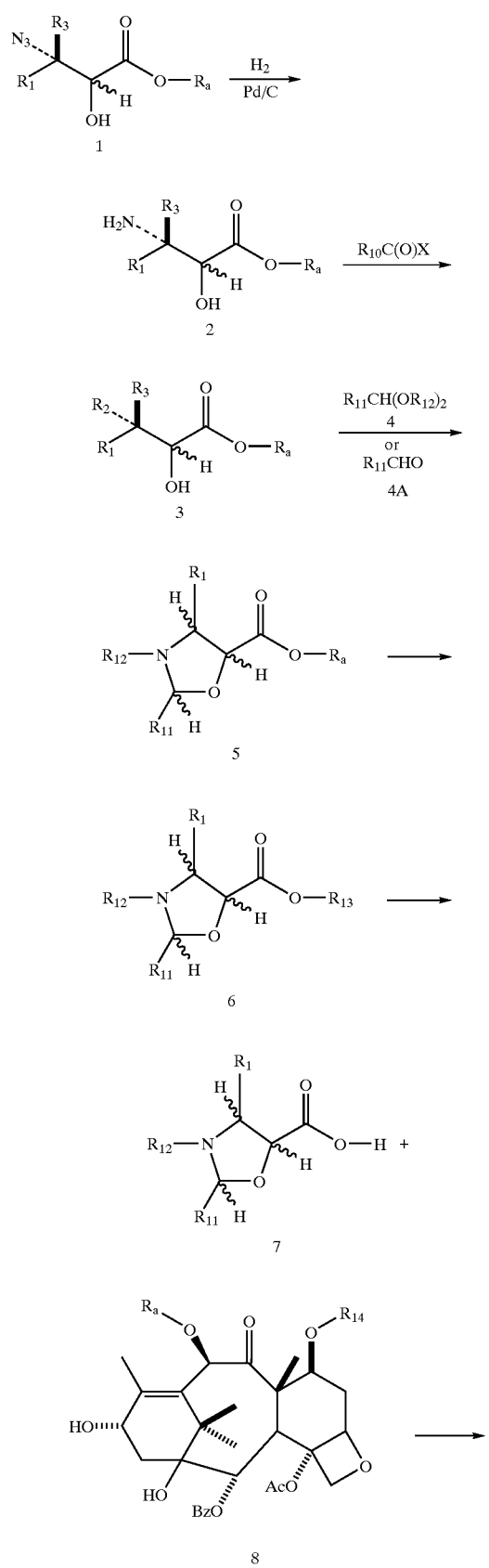
CHART B
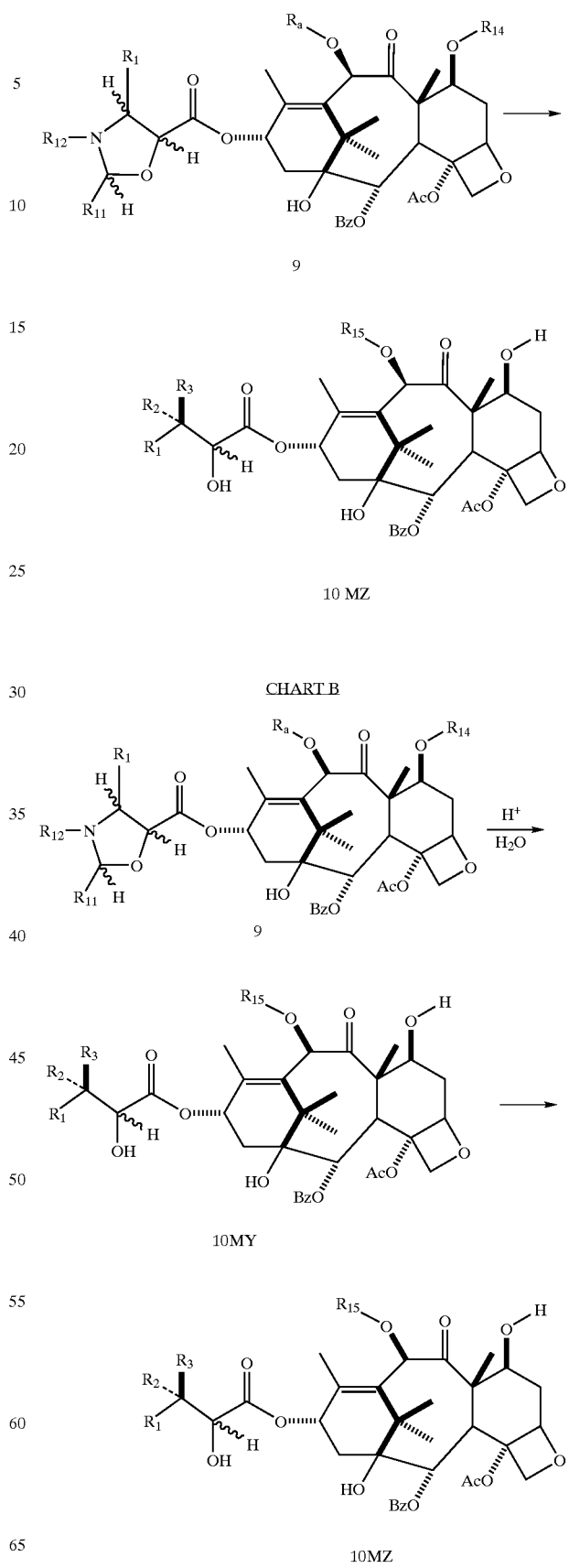

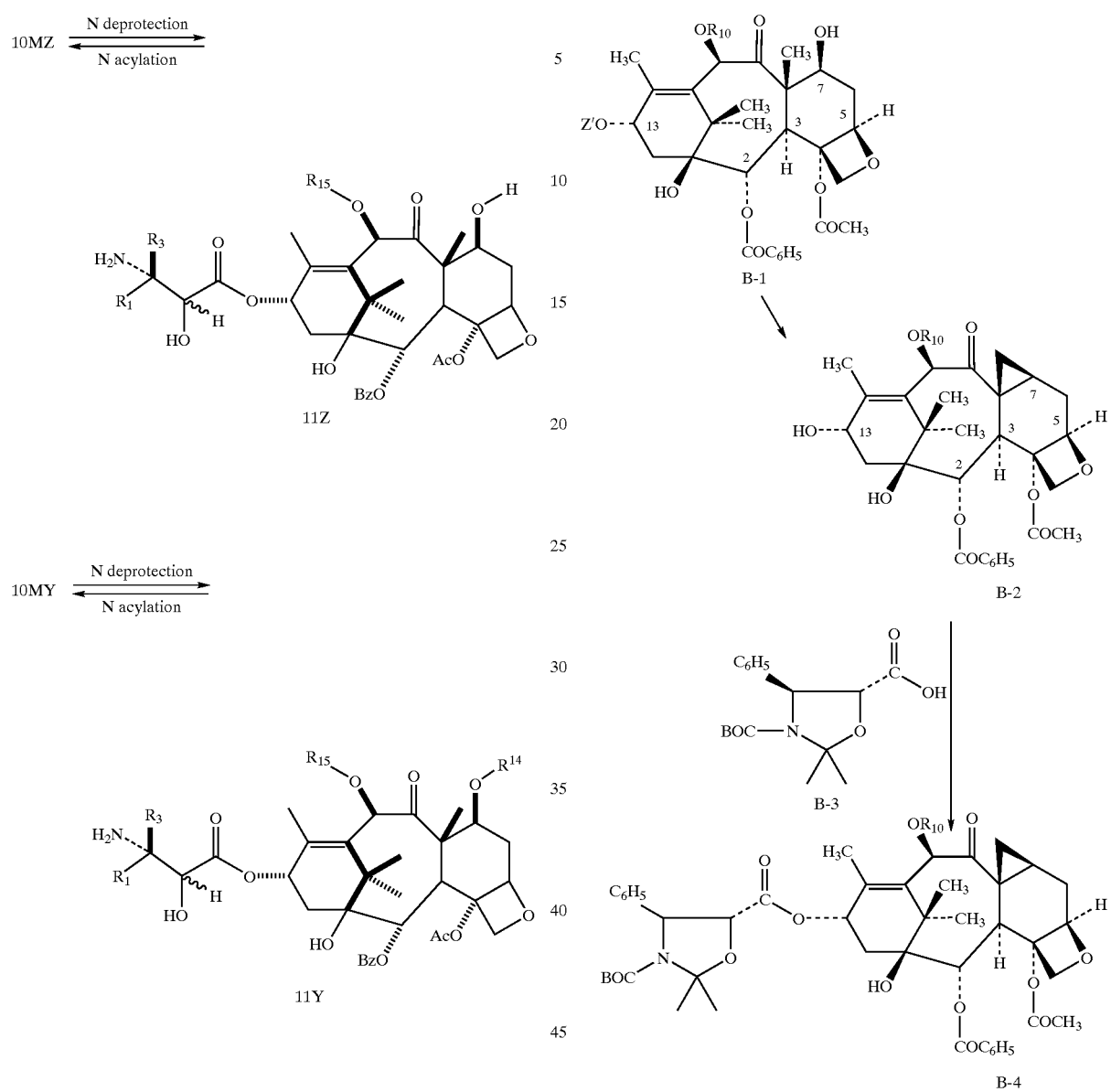
CHART B-II
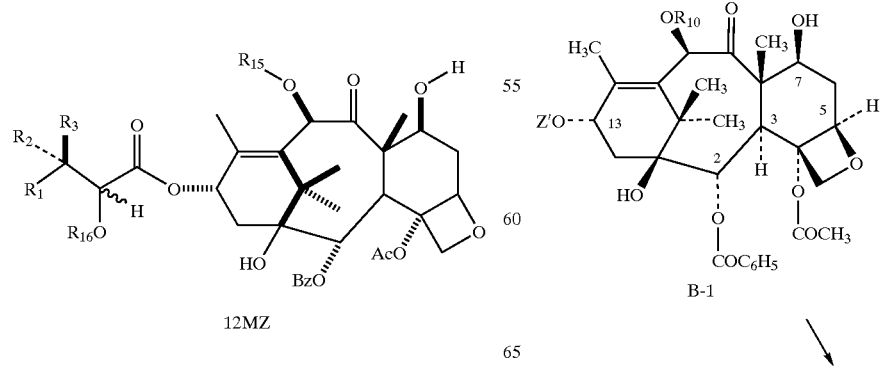
CHART B-III

FORMULA CHART
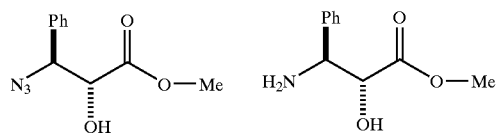
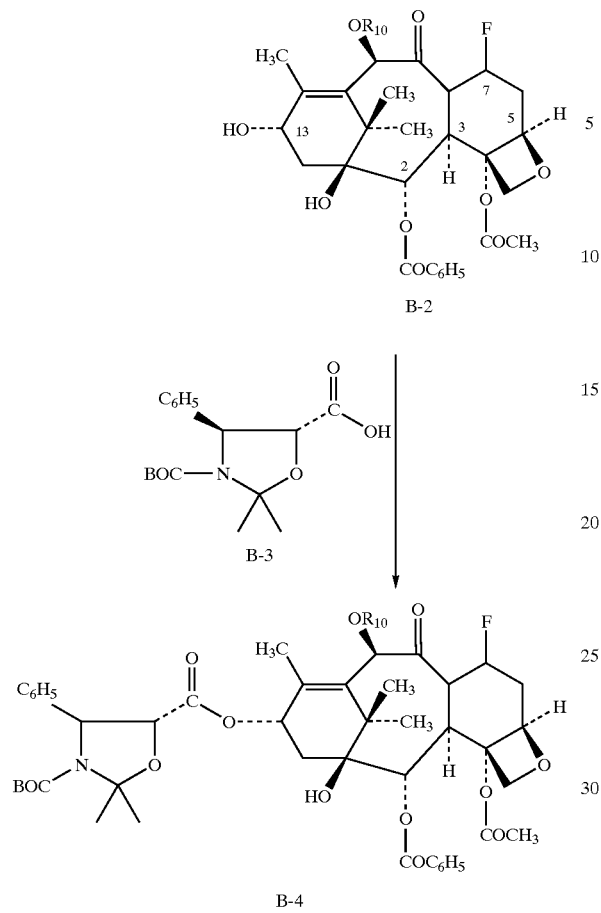
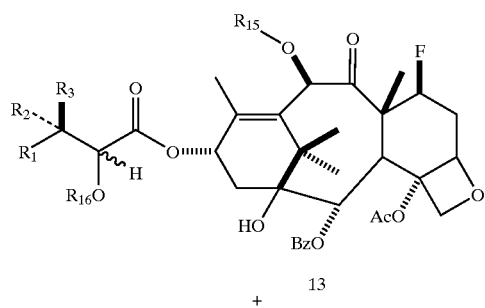
CHART C
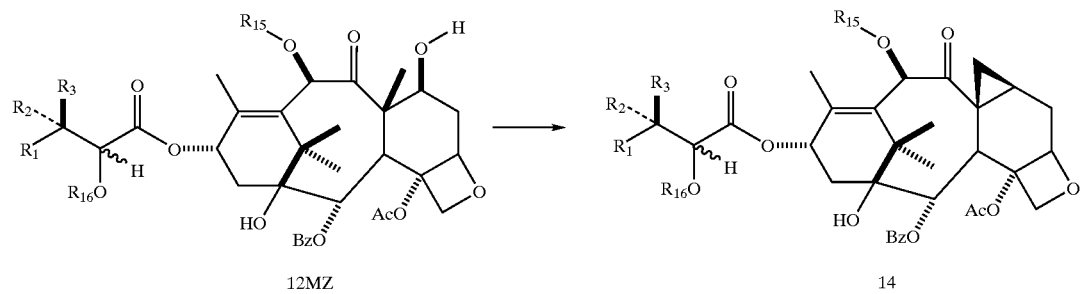

73
-continued
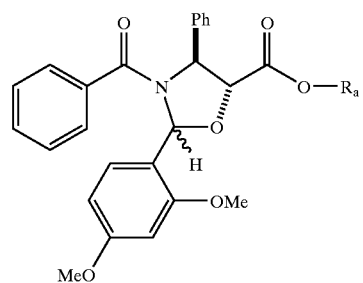
5Aa, 5Ab $R_a$ = Me
6Aa, 6Ab $R_a$ = K
7Aa, 7Ab $R_a$ = H
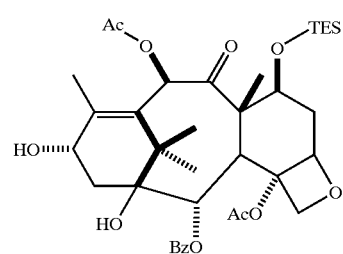
8A
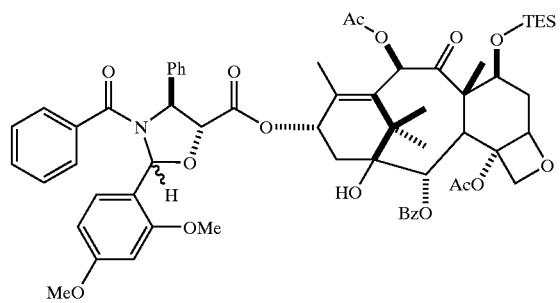
9AaA, 9AbA
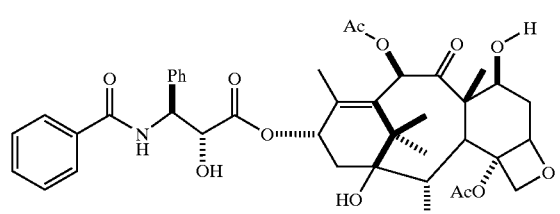
10AA
taxol
TES = Si(Et$_3$)
Ph = phenyl
Ac = C(O)CH$_3$
Bz = C(O)Ph
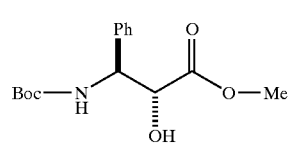
3B
74
-continued
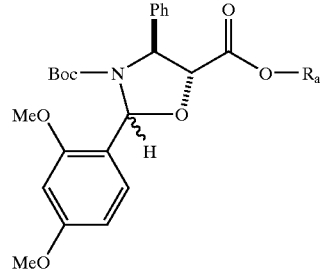
5Ba, 5Bb $R_a$ = Me
6Ba, 6Bb $R_a$ = K
7Ba, 7Bb $R_a$ = H
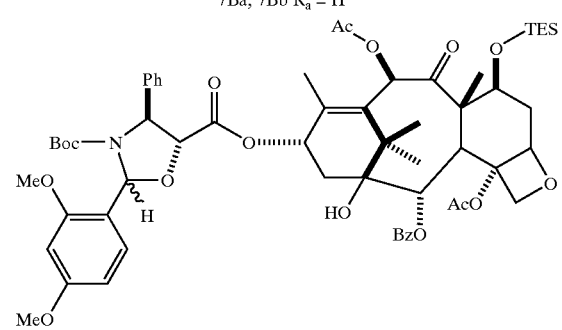
9BaA, 9BbA
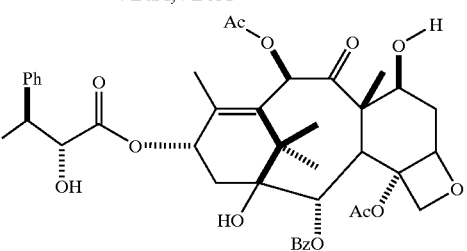
10BA
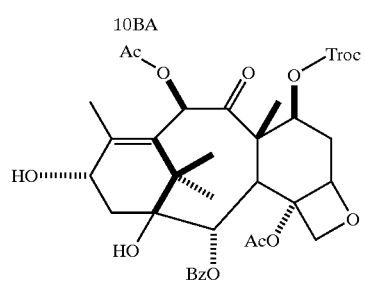
8B
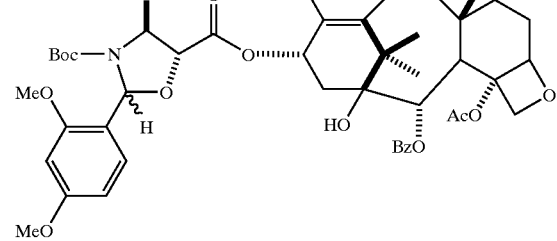
9BaB, 9BbB

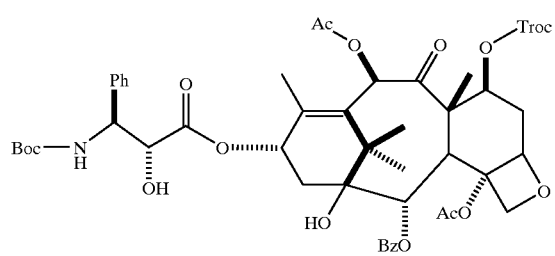
10BB
Troc = C(O)OCH$_2$CCl$_3$
Boc = C(O)O-t-Bu
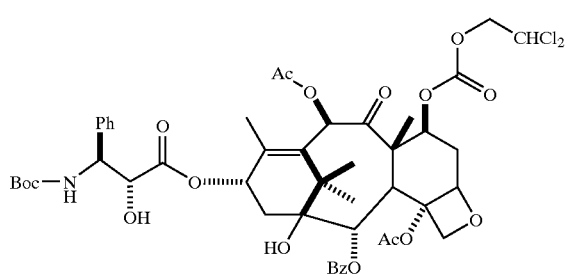
10BG
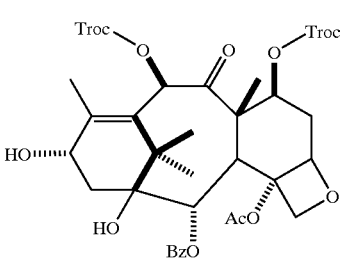
8C
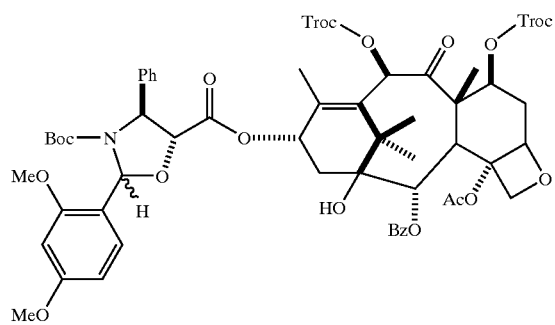
9BaC, 9BbC
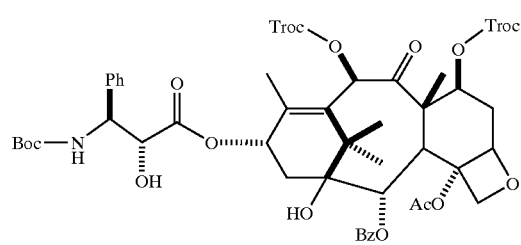
10BC
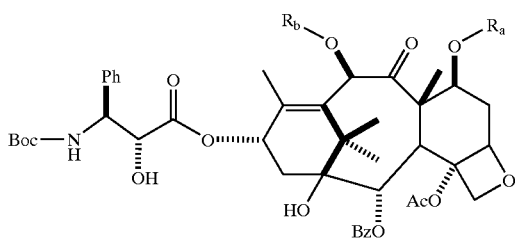
10
BD R$_b$ = H, R$_a$ = C(O)OCH$_2$CHCl$_2$
BE R$_b$ = C(O)OCH$_2$CHCl$_2$, R$_a$ = H
BF R$_b$ = H, R$_a$ = H Taxotere
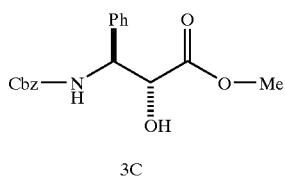
3C
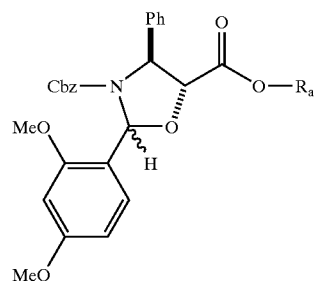
5Ca, 5Cb R$_a$ = Me
6Ca, 6Cb R$_a$ = K
7Ca, 7Cb R$_a$ = H
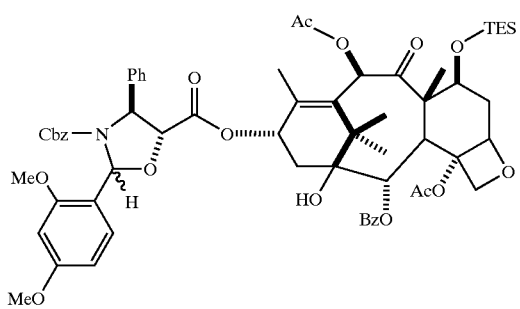
9CaA, 9CbA
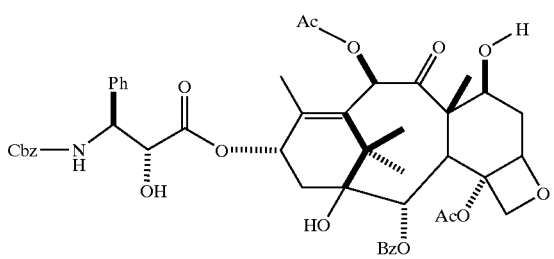
10CA
Cbz = C(O)OCH$_2$C$_6$H$_5$ -continued
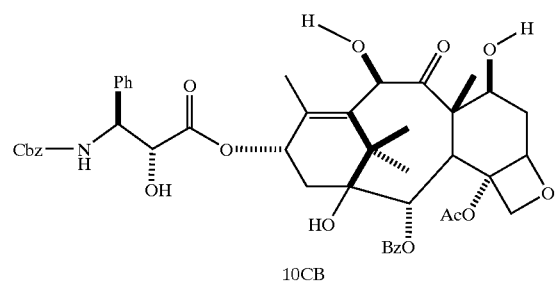
10CB
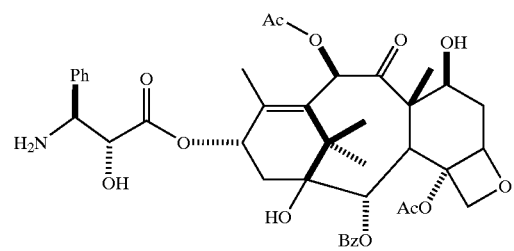
11A
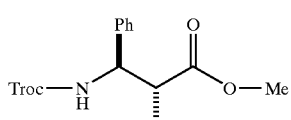
3D
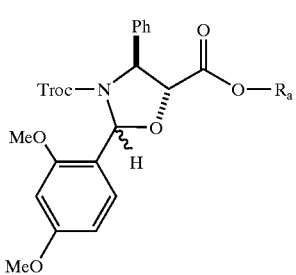
5Da, 5Db Rₐ = Me
6Da, 6Db Rₐ = K
7Da, 7Db Rₐ = H
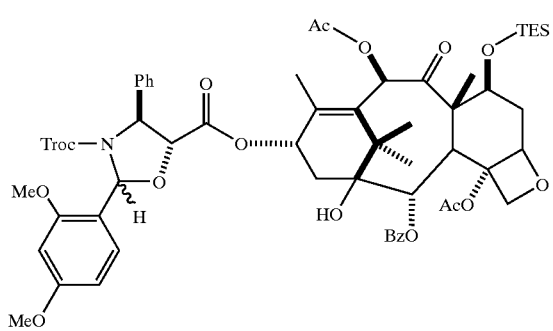
9DaA, 9DbA
-continued
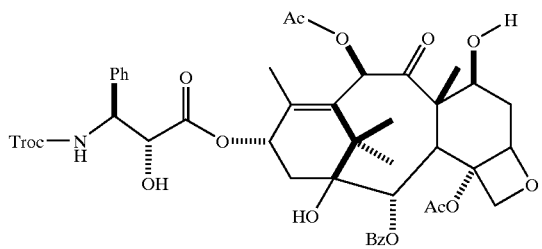
10DA
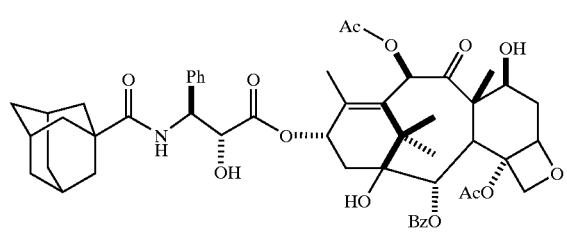
10EA
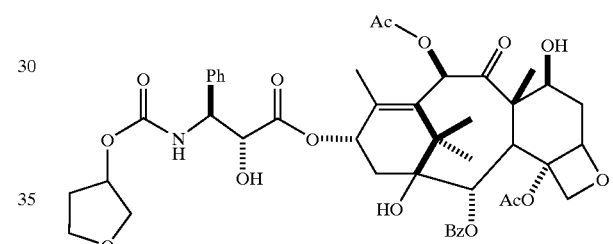
10FA
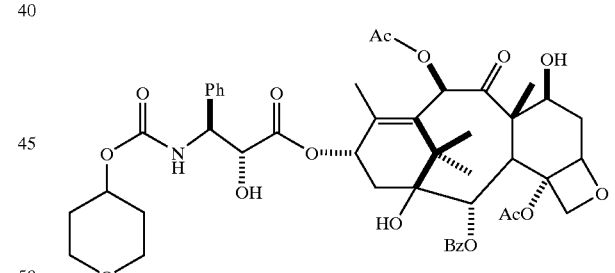
10GA
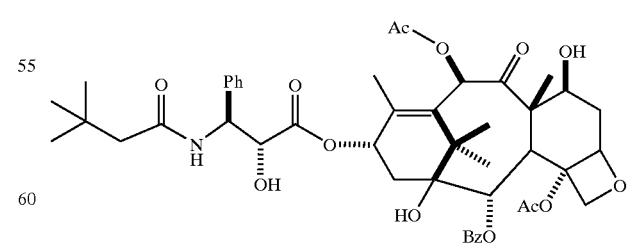
10HA

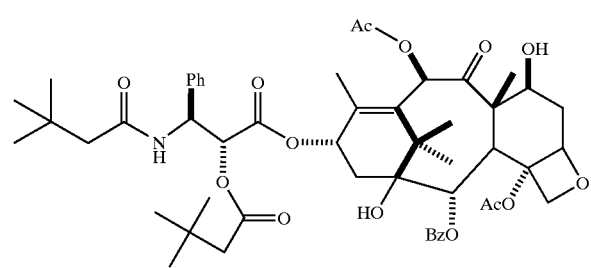
12CA
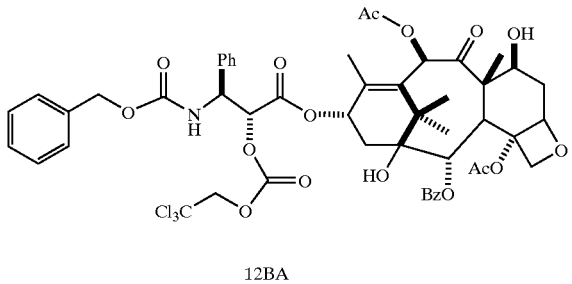
12BA
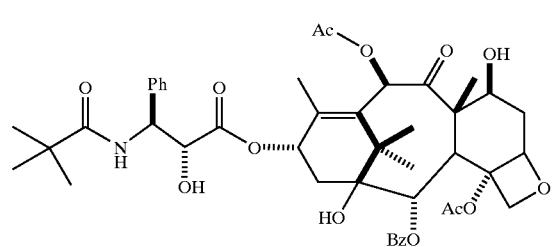
10lA
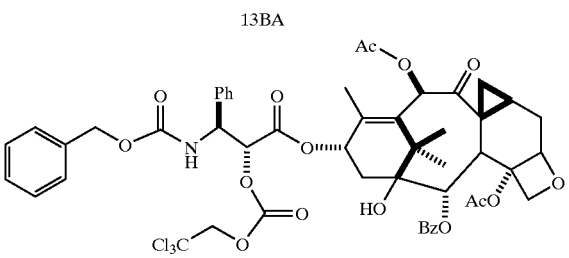
13BA
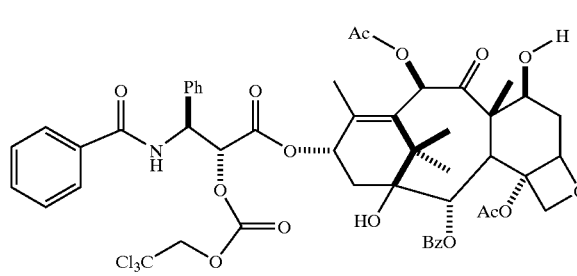
12AA
14BA
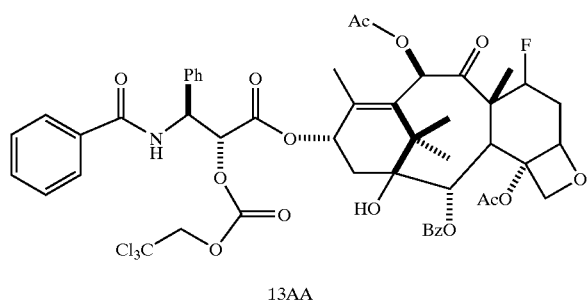
13AA
12DA
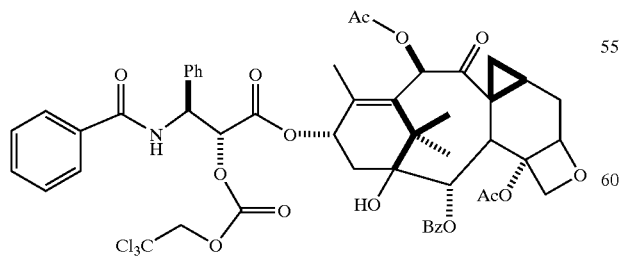
14AA
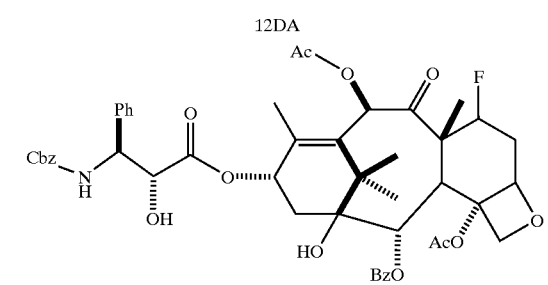
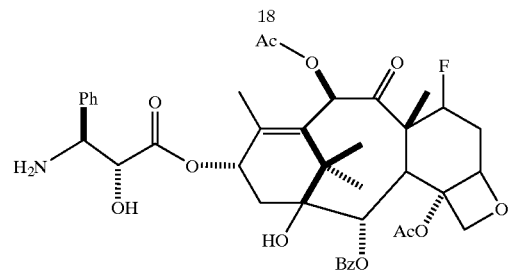
19

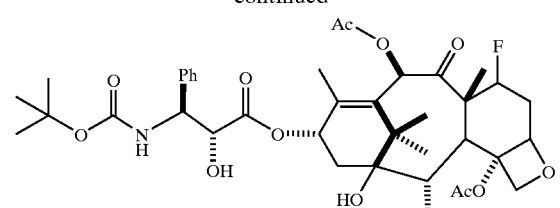
20
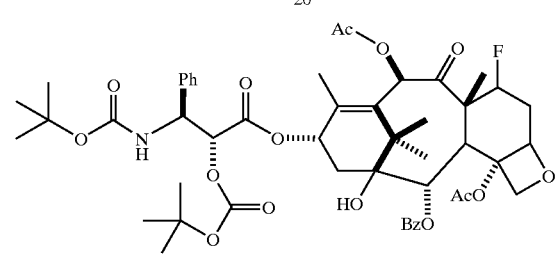
13CA
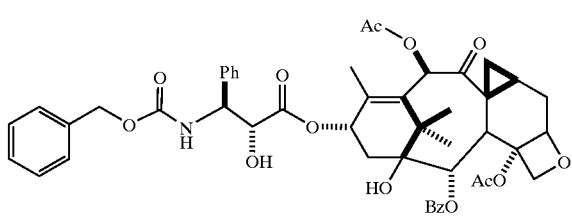
21
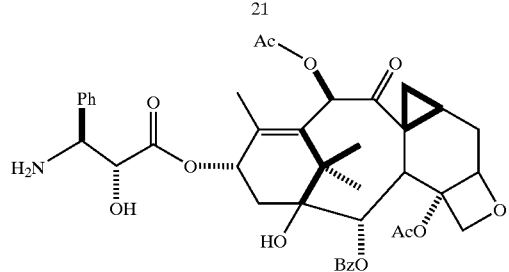
22
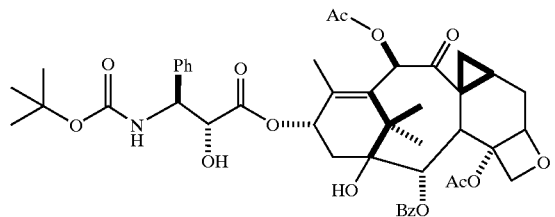
23
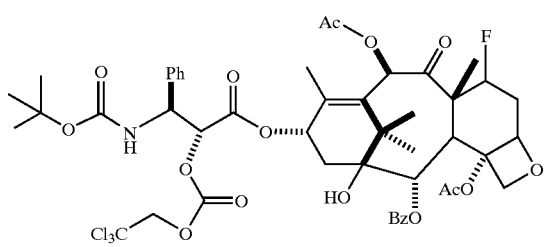
13DA
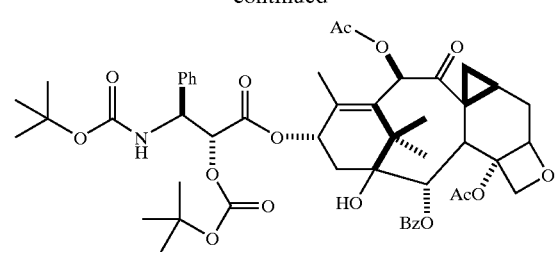
14CA
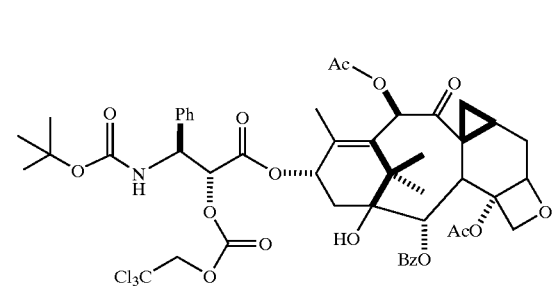
14DA
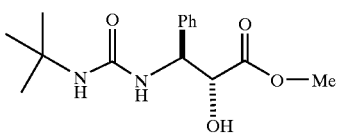
3K
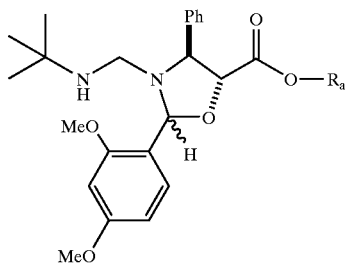
5Ka, 5Kb R$_a$ = Me
6Ka, 6Kb R$_a$ = K
7Ka, 7Kb R$_a$ = H
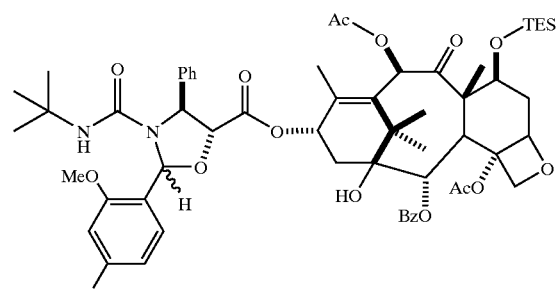
9KaA, 9KbA

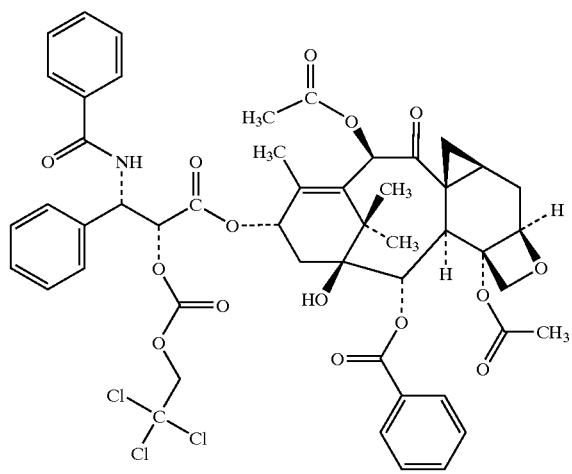
Compound IIa
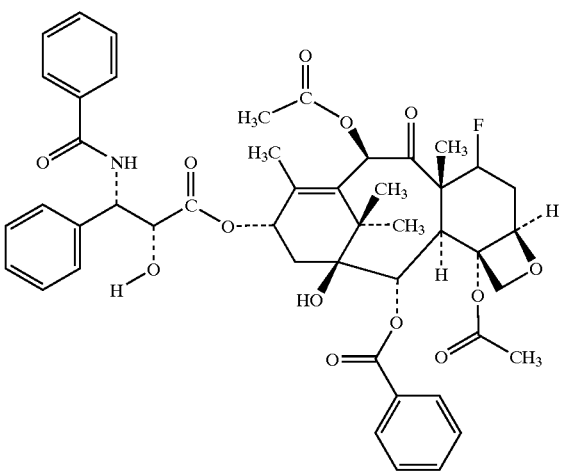
Compound IIIb
Compound IIb
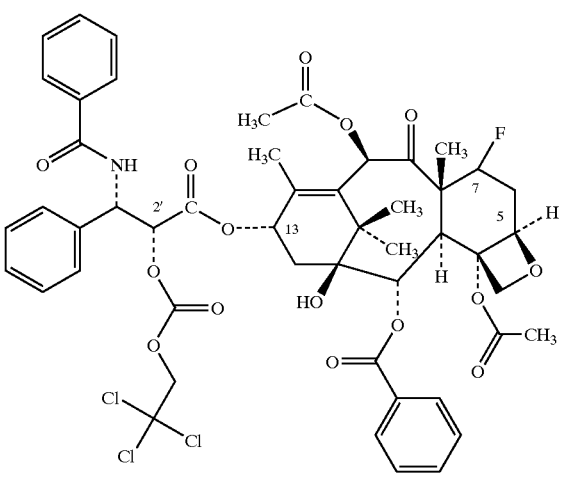
Compound IIIaα
Compound IIIa
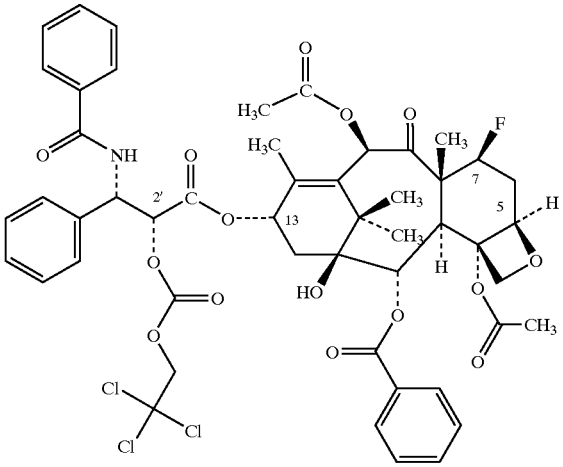
Compound IIIaβ

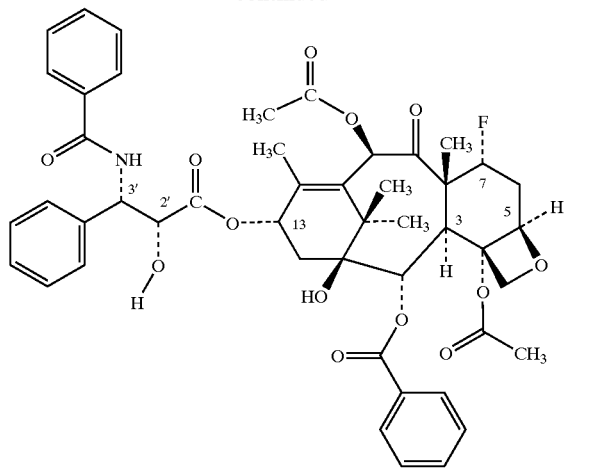
Compound IIIbα
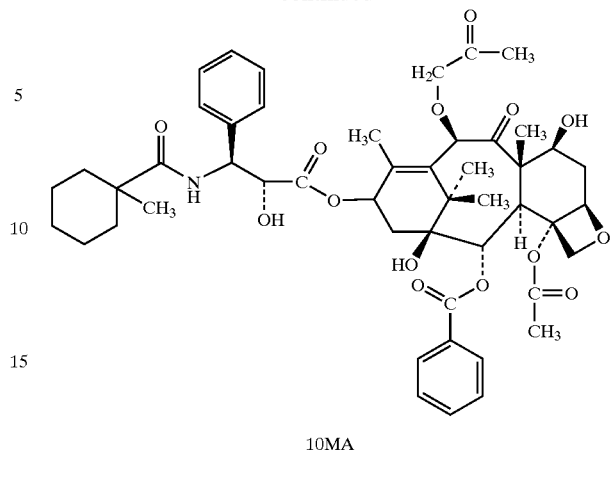
10MA
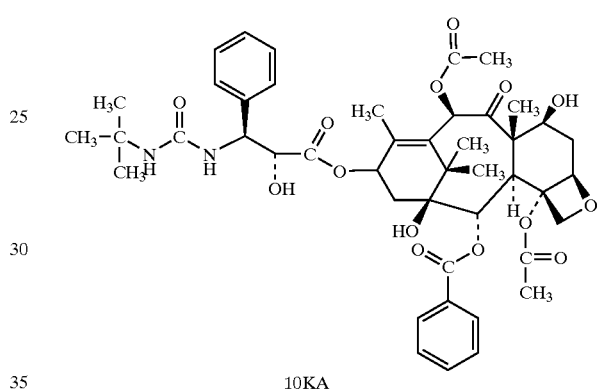
10KA
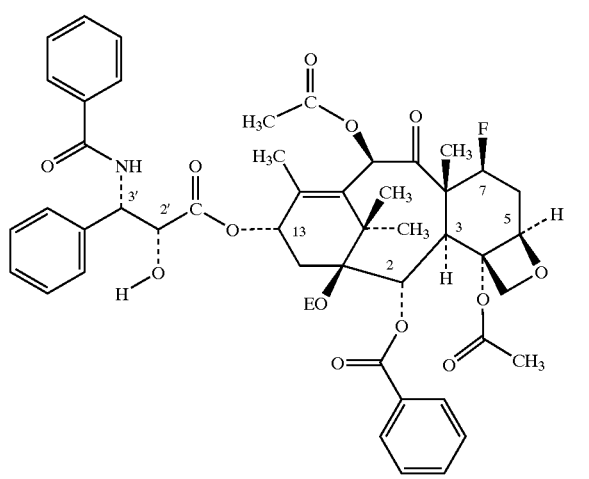
Compound IIIbβ
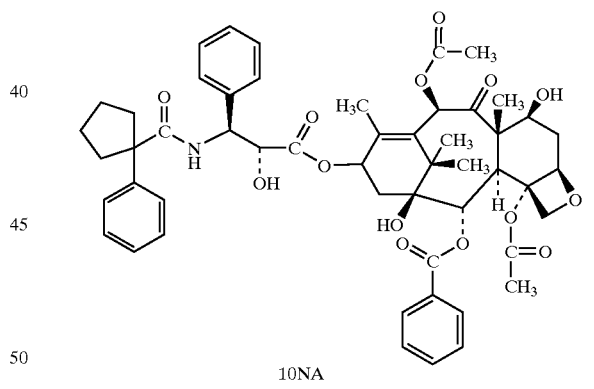
10NA
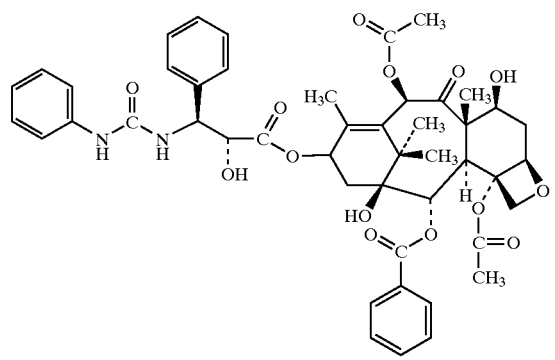
10JA
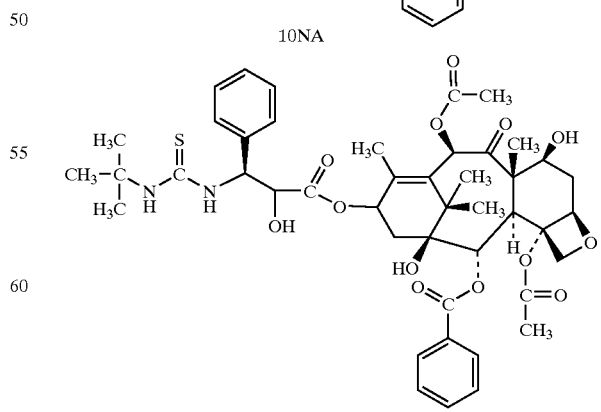
10LA 87
-continued
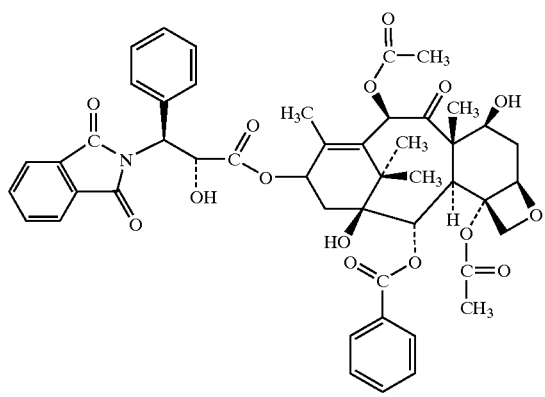
10PA
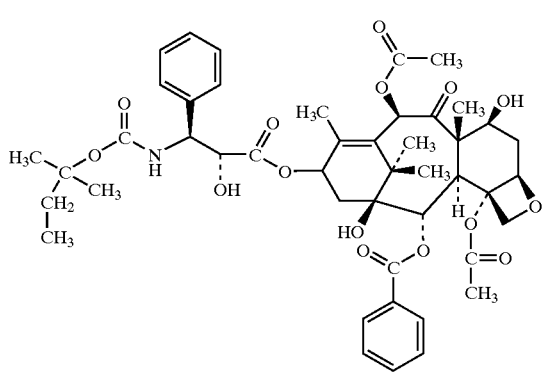
10RA
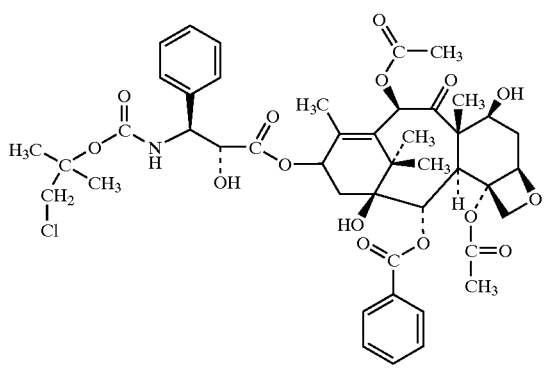
10SA
88
-continued
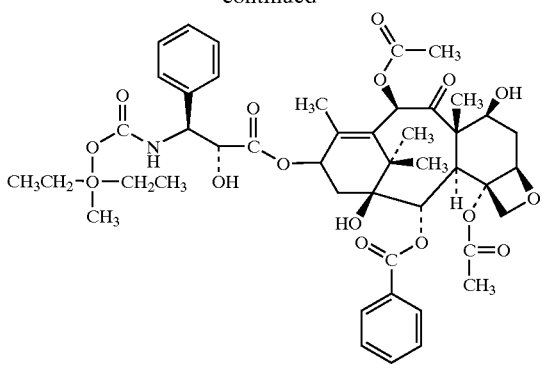
10TA
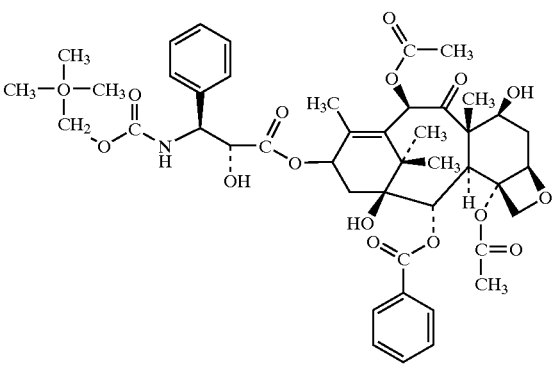
10UA
What is claimed is:
1. A process of preparing a compound of formula:
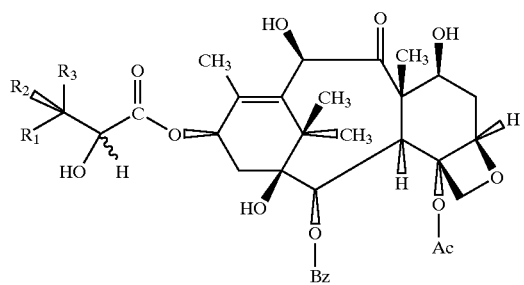
wherein
$R_1$ is selected from the group consisting of
—$CH_3$, —C$_6$H$_5$ or phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, and -2-furyl, 2-thienyl, 1-naphthyl, 2-naphthyl or 3,4-methylenedioxyphenyl;

R$_2$ is selected from the group consisting of —H, —NHC(O)H, —NHC(O)C$_1$–C$_{10}$alkyl, —NHC(O)phenyl, —NHC(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, —NHC(O)(CH$_3$)=CHCH$_3$, —NHC(O)OC(CH$_3$)$_3$, —NHC(O)OCH$_2$phenyl, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$), —NHC(O)OC$_1$–C$_{10}$alkyl, —NHC(O)NHC$_1$–C$_{10}$alkyl, —NHC(O)NHPh, —NHC(O)NHPh substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —NHC(O)C$_3$–C$_8$cycloalkyl, —NHC(O)C(CH$_2$CH$_3$)$_2$CH$_3$, —NHC(O)C(CH$_3$)$_2$CH$_2$Cl, —NHC(O)C(CH$_3$)$_2$CH$_2$CH$_3$, phthalimido, —NHC(O)-1-phenyl-1-cyclopentyl, —NHC(O)-1-methyl-1-cyclohexyl, —NHC(S)NHC(CH$_3$)$_3$, —NHC(O)NHCC(CH$_3$)$_3$ and —NHC(O)NHPh;

R$_3$ is selected from the group consisting of —H, —NHC(O)phenyl and —NHC(O)OC(CH$_3$)$_3$, with the overall proviso that one of R$_2$ and R$_3$ is —H but R$_2$ and R$_3$ are not both —H;

Bz is —C(O)phenyl; and

Ac is C(O)CH$_3$;

which comprises reacting a compound of formula:

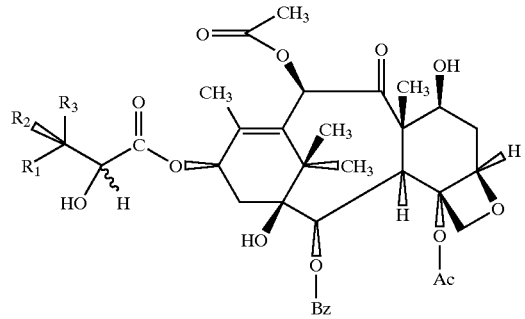

wherein R$_1$, R$_2$, R$_3$ Bz and Ac are as defined above;

with hydrazine.

* * * * *